United States Patent [19]

Takagaki et al.

[11] Patent Number: 5,942,521

[45] Date of Patent: Aug. 24, 1999

[54] QUINOLINONE DERIVATIVE AND ANTI-ALLERGIC AGENT WITH SAID QUINOLINONE DERIVATIVE AS THE ACTIVE INGREDIENT

[75] Inventors: Hidetsugu Takagaki, Sakura; Masayoshi Abe, Chiba; Mitsuru Sakai, Sakura; Yasuo Aoki, Yotsukaido; Shigenori Nakanishi; Nobuyuki Kimura, both of Sakura; Akihide Koda, Gifu, all of Japan

[73] Assignee: Dainippon Ink and Chemicals, Inc., Tokyo, Japan

[21] Appl. No.: 08/784,915

[22] Filed: Jan. 16, 1997

[30] Foreign Application Priority Data

Jan. 17, 1996 [JP] Japan .................................. 8-005449
Oct. 14, 1996 [JP] Japan .................................. 8-270866

[51] Int. Cl.[6] ........................ A61K 31/47; C07D 215/22; C07D 215/38
[52] U.S. Cl. ................................. 514/312; 546/155
[58] Field of Search .............................. 546/155; 514/312

[56] References Cited

U.S. PATENT DOCUMENTS

| 4,190,659 | 2/1980 | Hardtmann | 424/258 |
|---|---|---|---|
| 4,192,876 | 3/1980 | Hardtmann | 424/258 |
| 5,179,107 | 1/1993 | Afonso | 514/312 |

FOREIGN PATENT DOCUMENTS 0 101 330  2/1984  European Pat. Off. .
0 577 325  1/1994  European Pat. Off. .

*Primary Examiner*—Evelyn Mei Huang
*Attorney, Agent, or Firm*—Armstrong, Westerman, Hattori, McLeland & Naughton

[57] ABSTRACT

The present invention offers 7-aminoquinolinone derivatives, physiologically acceptable salts thereof, anti-allergic agents having as an active ingredient a 7-aminoquinolinone derivative or physiologically acceptable salt thereof, and 7-nitroquinolinone derivatives, wherein the 7-aminoquinolinone derivative is expressed by the following general formula (I):

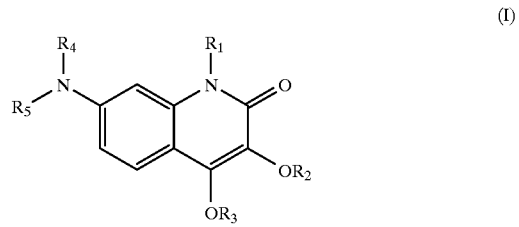

(I)

wherein $R_1$ is a hydrogen atom or an alkyl group;

$R_2$ and $R_3$ are mutually different groups, each of which is selected from among hydrogen atoms, acyl groups, alkyl groups or alkenyl groups; and $R_4$ and $R_5$ are mutually different or identical groups, each of which is selected from among hydrogen atoms, acyl groups, alkyl groups, alkenyl groups or aralkyl groups; and physiologically acceptable salts thereof.

34 Claims, No Drawings

5,942,521

QUINOLINONE DERIVATIVE AND ANTI-ALLERGIC AGENT WITH SAID QUINOLINONE DERIVATIVE AS THE ACTIVE INGREDIENT

BACKGROUND OF THE INVENTION

1. Technical Field of the Invention

The present invention relates to new 7-aminoquinolinone derivatives and physiologically acceptable salts thereof which are effective as treating agents or supressants for allergic disease, to 7-nitroquinolinone derivatives which are synthetic intermediates of said 7-aminoquinolinones, and to anti-allergic agents containing said 7-aminoquinolinone derivatives and physiologically acceptable salts thereof as the active ingredients.

2. Background Art

With regard to quinolinone derivatives wherein oxygen atoms are directly bonded at the 3- and 4-positions as with the present invention, several compounds are disclosed in the publications listed below.

First, as quinolinone compounds having substituent groups at the 3- and 4-positions of the nitrogen-containing ring of quinolinone while lacking substituent groups on the aromatic group ring, *Monatsh.Chem.*, 98(1), pp. 100–104, 1967 discloses infrared absorption spectrum data for 3-methoxy-4-hydroxy-2(1H)-quinolinone, 3-ethoxy-4-hydroxy-2(1H)-quinolinone, and 3,4-dimethoxy-2(1H)-quinolinone.

*Monatsh.Chem.*, 99(6), pp. 2157–2166, 1968 also discloses a method for producing 3,4-dihydroxy-2(1H)-quinolinone and 3,4-dihydroxy-1-phenyl-2(1H)-quinolinone.

Additionally, *Liebigs Ann. Chem.*, 9, pp. 1545–1551, 1973 discloses a method for producing 3,4-dihydroxy-1-phenyl-2(1H)-quinolinone and 3,4-diacetoxy-1-phenyl-2(1H)-quinolinone.

Furthermore, *Chem. Ber.* 106, pp. 1537–1548, 1973 discloses a method for producing 3,4-dihydroxy-1-methyl-2(1H)-quinolinone, and *Z. Naturforsch., B; Anorg. Chem., Org. Chem.*, 33B (4) pp. 429–432, 1978 discloses a method for producing 3,4-dihydroxy-1-phenyl-2(1H)-quinolinone.

*Monatsh.Chem.*, 115(2), pp. 231–242, 1984 discloses a method for producing 3,4-dihydroxy- 2(1H)-quinolinone, 3-methoxy-4-hydroxy-2(1H)-quinolinone, 3-ethoxy-4-hydroxy-2(1H)-quinolinone, 3-propoxy-4-hydroxy-2(1H)-quinolinone, 3-trifluoroacetoxy-4-hydroxy-2(1H)-quinolinone, 3-acetoxy-4-hydroxy-2(1H)-quinolinone, 3-acetoxy-4-hydroxy-1-methyl-2(1H)-quinolinone, and 3-methoxy-4-hydroxy-1-methyl-2(1H)-quinolinone.

*Phosphorus and Sulfur*, 21(1), pp. 47–52, 1984 discloses 3,4-dihydroxy-2(1H)-quinolinone 3-dimethylphosphate, 3-hydroxy-4-methoxy-2(1H)-quinolinone 3-dimethylphosphate, 3,4-dihydroxy-2(1H)-quinolinone 3-diethylphosphate, 3,4-dihydroxy-2(1H)-quinolinone 3-diisopropylphosphate, and N-methyls of these compounds.

*FEBS Lett.*, 246(1–2), pp. 113–116, 1989 discloses a method for producing 3,4-dihydroxy-2(1H)-quinolinone.

*Phytochemistry*, 28(5), p. 1517–1519, 1989 discloses 3,4-dimethoxy-2(1H)-quinolinone and 3,4-dimethoxy-1-methyl-2(1H)-quinolinone as extracts of *Clausena anisata*.

As compounds having substituent groups on the aromatic ring of a quinolinone, *Indian J Chem., Sect. B*, 15B(5), pp. 440–444, 1977 discloses 3,4-dimethoxy-2(1H)-quinolinone, 8-methoxy-3-methoxy-4-hydroxy-1-methyl-2(1H)-quinolinone, and a methyl ether thereof, 8-methoxy-3,4-dimethoxy-1-methyl-2(1H)-quinolinone as compounds obtained from the bark of *Chloroxylon swietenia* DC.

Additionally, *Indian J Chem., Sect. B*, 22B(12), pp. 1254–1256, 1983 discloses a method for producing 8-methoxy-3-methoxy-4-hydroxy-2(1H)-quinolinone and 8-methoxy-3,4-dimethoxy-1-methyl-2(1H)-quinolinone.

Additionally, *J Heterocyclic Chem.*, 22, pp.1087–1088, 1985 discloses a method for producing 3-methoxy-4-hydroxy-1-methyl-2(1H)-quinolinone and 8-methoxy-3-methoxy-4-hydroxy-1-methyl-2(1H)-quinolinone.

*Journal of Natural Products*, 58(4), pp. 574–576, 1995 discloses 8-methoxy-3,4-dihydroxy-2(1H)-quinolinone as a component obtained from *Eriostemon gardneri* However, as described above, only methoxy groups are known as substituent groups for the aromatic group rings of quinolinone derivatives.

Additionally, U.S. Pat. No. 5,378,694 (corresponding to WO 92/04,328 and Japanese Patent Application, Second Publication No. Hei 6-502,845) describes quinolinone derivatives having a carbonyl group as the 3-position substituent group and a hydroxyl group or an alkoxy group as the 4-position substituent group, and the anti-viral activities and anti-hypertension activities of these compounds.

Additionally, U.S. Pat. No. 5,412,104 (corresponding to WO 92/04327 and Japanese Patent Application, Second Publication No. Hei 7-110,853) describes quinolinone derivatives having a substituent group containing a carbonyl group as the 3-position substituent group and an alkoxy group, a carbonyloxy group or an amino group as the 4-position substituent group, and the anti-viral activities of these compounds; European Patent No. 459,561 A2 discloses 2,4-dioxotetrahydroquinoline derivatives wherein the 3-position substituent group is a substituent group containing a carbonyl group and the 4-position group is a variable 4-ketone.

European Patent Application, Publication No. 481,676 Al discloses a quinolinone derivative having an aromatic group with a substituent group as the 3-position substituent group and a hydroxyl group as the 4-position substituent group; U.S. Pat. No. 4,124,587 discloses a quinolinone derivative having a sulfinyl group as the 3-position substituent group and a hydroxyl group as the 4-position substituent group; and U.S. Pat. No. 4,127,574 discloses a quinolinone derivative having a sulfonyl group as the 3-position substituent group and a hydroxyl group as the 4-position substituent group.

European Patent Application, Publication No. 685,466 Al discloses a quinolinone derivative having a sulfide group as the 3-position substituent group and a hydroxyl group as the 4-position substituent group, and WO 96/04288 discloses 5,7-dimethyl-4-hydroxy-2(1H)-quinolinone and 5,7-dichloro-4-hydroxy-2(1H)-quinolinone.

Furthermore, U.S. Pat. No. 5,179,107 and U.S. Pat. No. 5,190,956 abstractly describe an extremely wide range of quinolinone derivatives having substituent groups on the aromatic group ring and having oxygens directly bonded to the 3- and 4-positions. However, the U. S. patents do not disclose quinolinone derivatives having a substituent group, such as an amino group or a nitro group, bonded to the 7-position which the present invention provides.

These US patent publications disclose quinolinone derivatives having the characteristic that the substituent groups at the 3- and 4-positions are identical substituent groups, and disclose that these have anti-viral activity.

However, the U.S. patents disclose neither quinolinone derivatives having an amino group bonded to the 7-position nor their anti-allergic activities which are the objects of the present invention.

On the other hand, while numerous anti-allergic agents effective against only immediate type allergies (i.e. I-type allergies) are known, there are almost no reports of anti-allergic agents effective against delayed type allergies. However, of the various types of allergic diseases, the delayed type allergies contribute to the intractable allergic diseases, so that steroids which are effective against delayed type allergies are used clinically.

Although steroids offer strong treatment effects, they also have serious side effects such as digestive ulcers, susceptibility to infections, psychological disturbances, steroidal glycosuria, hirsutism, moonface, osteoporosis wherein the bones become brittle, and obesity. For this reason, the clinical use of steroids must be tightly restricted, and requires the close supervision of physicians.

Thus, steroids are largely used as external medications primarily for light allergic skin diseases, but while their effectiveness against generalized allergic diseases, especially delayed type allergies, is acknowledged, their use is currently tightly restricted, so that the development of a medication which is effective against both immediate type and delayed type allergies while having few side effects has been desired.

As described above, quinolinone derivatives having a derivative of an amino group as a substitutent at the 7-position and 7-nitroquinolinone derivatives which are synthetic intermediates of the former have not been known. Furthermore, the facts that 7-aminoquinolinone derivatives and physiologically acceptable salts thereof offer anti-allergic agents which are effective against immediate type allergic diseases and delayed type allergic diseases while having few side effects have not been known.

SUMMARY OF THE INVENTION

The object of the present invention is to offer new nitroquinolinone derivatives, aminoquinolinone derivatives synthesized from these nitroquinolinone derivatives, and physiologically acceptable salts thereof, as well as to offer an extremely safe medication having these aminoquinolinone derivatives and physiological acceptable salts thereof as active ingredients, especially anti-allergic agents which are effective against immediate type allergic diseases and delayed type allergic diseases. Furthermore, the present invention also has an object of offering a method for treating allergic diseases of mammals, the method comprising the step of administrating a pathologically effective amount of the medication described above.

In order to achieve the above-mentioned object, the present inventors synthesized numerous compounds, then evaluated their medical effectiveness and safety. As a result, they succeeded in synthesizing a 7-nitroquinolinone derivative having a nitro group as a substituent group on the aromatic group ring, then further succeeded in synthesizing from this compound a 7-aminoquinolinone derivative having an amino group, and discovered that the 7-aminoquinolinone derivative is extremely effective as an anti-allergic agent to complete the present invention.

The present invention offers 7-aminoquinolinone derivatives, physiologically acceptable salts thereof, anti-allergic agents having as an active ingredient a 7-aminoquinolinone derivative or physiologically acceptable salt thereof, and 7-nitroquinolinone derivatives described in more detail as follows.

(1) A 7-aminoquinolinone derivative expressed by the following general formula (I):

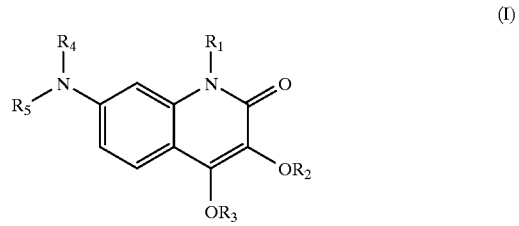

wherein
$R_1$ is a hydrogen atom or an alkyl group;
$R_2$ and $R_3$ are mutually different groups, each of which is selected from among hydrogen atoms, acyl groups, alkyl groups or alkenyl groups; and
$R_4$ and $R_5$ are mutually different or identical groups, each of which is selected from among hydrogen atoms, acyl groups, alkyl groups, alkenyl groups or aralkyl groups; and physiologically acceptable salts thereof.

(2) A 7-aminoquinolinone derivative in accordance with above description (1), wherein $R_1$ is a hydrogen atom or a straight-chain or branched-chain alkyl group having 1~10 carbon atoms; and physiologically acceptable salts thereof (3) A 7-aminoquinolinone derivative in accordance with above description (1), wherein $R_2$ and $R_3$ are each a hydrogen atom, an acyl group, a straight-chain or branched-chain alkyl group having 1~10 carbon atoms, or a straight-chain or branched-chain alkenyl group having 2~10 carbon atoms; and physiologically acceptable salts thereof (4) A 7-aminoquinolinone derivative in accordance with above description (1), wherein $R_4$ and $R_5$ are identical or different, and each is a hydrogen atom, an acyl group, a straight-chain or branched-chain alkyl group having 1~10 carbon atoms, a straight-chain or branched-chain alkenyl group having 2~10 carbon atoms, or an aralkyl group; and physiologically acceptable salts thereof (5) A 7-aminoquinolinone derivative in accordance with any one of above description (1) through (4), wherein $R_1$ is a hydrogen atom or a straight-chain or branched-chain alkyl group having 1~10 carbon atoms; $R_2$ and $R_3$ are each a hydrogen atom, an acyl group, a straight-chain or branched-chain alkyl group having 1~10 carbon atoms, or a straight-chain or branched-chain alkenyl group having 2~10 carbon atoms; and $R_4$ and $R_5$ are identical or different, and each is a hydrogen atom, an acyl group, a straight-chain or branched-chain alkyl group having 1~10 carbon atoms, a straight-chain or branched-chain alkenyl group having 2~10 carbon atoms, or an aralkyl group; and physiologically acceptable salts thereof (6) A 7-aminoquinolinone derivative in accordance with above description (5), wherein $R_2$ is a hydrogen atom; and $R_3$ is a straight-chain or branched-chain alkyl group having 1~10 carbon atoms, or a straight-chain or branched-chain alkenyl group having 2~10 carbon atoms; and physiologically acceptable salts thereof (7) A 7-aminoquinolinone derivative in accordance with above description (5), wherein $R_2$ is an acyl group; and $R_3$ is a hydrogen atom; and physiologically acceptable salts thereof (8) A 7-aminoquinolinone derivative in accordance with above description (5), wherein $R_2$ is an acyl group; and $R_3$ is a straight-chain or branched-chain alkyl group having 1~10 carbon atoms, or a straight-chain or branched-chain alkenyl group having 2~10 carbon atoms; and physiologically acceptable salts thereof (9) A 7-aminoquinolinone derivative in accordance with above description (5), wherein $R_2$ is a straight-chain or branched-chain alkyl group having 1~10 carbon atoms, or a straight-chain or branched-chain alkenyl group having 2~10 carbon atoms; and $R_3$ is a hydrogen atom; and physiologically acceptable salts thereof.

(10) A 7-aminoquinolinone derivative in accordance with above description (5), wherein $R_2$ is a straight-chain or branched-chain alkyl group having 1~10 carbon atoms, or a straight-chain or branched-chain alkenyl group having 2~10 carbon atoms; and $R_3$ is an acyl group; and physiologically acceptable salts thereof

(11) A 7-aminoquinolinone derivative in accordance with above description (5), wherein $R_2$ and $R_3$ are mutually different straight-chain or branched-chain alkyl groups having 1~10 carbon atoms, or straight-chain or branched-chain alkenyl groups having 2~10 carbon atoms; and physiologically acceptable salts thereof

(12) A 7-aminoquinolinone derivative in accordance with any one of above description (6) through (11), wherein $R_4$ is a hydrogen atom; and $R_5$ is a hydrogen atom, an acyl group, a straight-chain or branched-chain alkyl group having 1~10 carbon atoms, a straight-chain or branched-chain alkenyl group having 2~10 carbon atoms, or an aralkyl group; and physiologically acceptable salts thereof

(13) A 7-aminoquinolinone derivative in accordance with above description (12), wherein $R_5$ is an acyl group; and physiologically acceptable salts thereof

(14) A 7-aminoquinolinone derivative in accordance with above description (13) wherein $R_5$ is an acyl group composed of a cinnamoyl group which may have substituent groups; and physiologically acceptable salts thereof.

(15) A 7-aminoquinolinone derivative in accordance with above description (14), wherein $R_5$ is a 4-hydroxy-3-methoxycinnamoyl group, or a 3,5-dimethoxy-4-hydroxycinnamoyl group; and physiologically acceptable salts thereof.

(16) An anti-allergic agent having as an active ingredient a 7-aminoquinolinone derivative or physiologically acceptable salt thereof in accordance with any one of above description (1) through (11).

(17) An anti-allergic agent having as an active ingredient a 7-aminoquinolinone derivative or physiologically acceptable salt thereof in accordance with description (12).

(18) An anti-allergic agent having as an active ingredient a 7-aminoquinolinone derivative or physiologically acceptable salt thereof in accordance with description (13).

(19) An anti-allergic agent having as an active ingredient a 7-aminoquinolinone derivative or physiologically acceptable salt thereof in accordance with description (14).

(20) An anti-allergic agent having as an active ingredient a 7-aminoquinolinone derivative or physiologically acceptable salt thereof in accordance with description (15).

(21) A 7-aminoquinolinone derivative expressed by the following general formula (I):

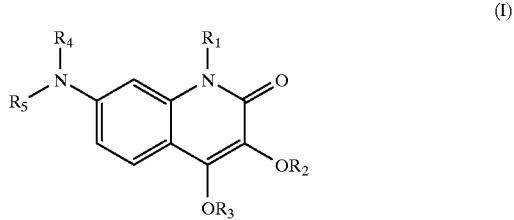

(I)

wherein
$R_1$ is a hydrogen atom or a straight-chain or branched-chain alkyl group having 1~10 carbon atoms;
$R_2$ and $R_3$ are identical groups, selected from among hydrogen atoms, alkyl groups or alkenyl groups; and
$R_4$ and $R_5$ are mutually different or identical groups, each of which is selected from among hydrogen atoms, acyl groups, alkyl groups, alkenyl groups or aralkyl groups; and physiologically acceptable salts thereof

(22) A 7-aminoquinolinone derivative in accordance with above description (21), wherein $R_2$ and $R_3$ are hydrogen atoms, straight-chain or branched-chain alkyl groups having 1~10 carbon atoms, or straight-chain or branched-chain alkenyl groups having 2~10 carbon atoms; and physiologically acceptable salts thereof

(23) A 7-aminoquinolinone derivative in accordance with above description (21), wherein $R_4$ and $R_5$ are mutually different or identical groups, each of which is selected from among hydrogen atoms, acyl groups, straight-chain or branched-chain alkyl groups having 1~10 carbon atoms, or straight-chain or branched-chain alkenyl groups having 2~10 carbon atoms or aralkyl groups; and physiologically acceptable salts thereof

(24) A 7-aminoquinolinone derivative in accordance with any one of above description (21) through (23), wherein $R_2$ and $R_3$ are hydrogen atoms, straight-chain or branched-chain alkyl groups having 1~10 carbon atoms, or straight-chain or branched-chain alkenyl groups having 2~10 carbon atoms; and $R_4$ and $R_5$ are mutually different or identical groups, each of which is selected from among hydrogen atoms, acyl groups, straight-chain or branched-chain alkyl groups having 1~10 carbon atoms, or straight-chain or branched-chain alkenyl groups having 2–10 carbon atoms or aralkyl groups; and physiologically acceptable salts thereof

(25) A 7-aminoquinolinone derivative in accordance with above description (24), wherein $R_2$ and $R_3$ are hydrogen atoms; and physiologically acceptable salts thereof

(26) A 7-aminoquinolinone derivative in accordance with above description (24), wherein $R_2$ and $R_3$ are straight-chain or branched-chain alkyl groups having 1~10 carbon atoms, or straight-chain or branched-chain alkenyl groups having 2~10 carbon atoms; and physiologically acceptable salts thereof.

(27) A 7-aminoquinolinone derivative in accordance with above description (25), wherein $R_4$ is a hydrogen atom; and $R_5$ is a hydrogen atom, an acyl group, a straight-chain or branched-chain alkyl group having 1~10 carbon atoms, or a straight-chain or branched-chain alkenyl group having 2~10 carbon atoms or an aralkyl group; and physiologically acceptable salts thereof.

(28) A 7-aminoquinolinone derivative in accordance with above description (26), wherein $R_4$ is a hydrogen atom; and $R_5$ is a hydrogen atom, an acyl group, a straight-chain or branched-chain alkyl group having 1~10 carbon atoms, or a straight-chain or branched-chain alkenyl group having 2~10 carbon atoms or an aralkyl group; and physiologically acceptable salts thereof.

(29) A 7-aminoquinolinone derivative in accordance with above description (27), wherein $R_5$ is an acyl group; and physiologically acceptable salts thereof.

(30) A 7-aminoquinolinone derivative in accordance with above description (28), wherein $R_5$ is an acyl group; and physiologically acceptable salts thereof.

(31) A 7-aminoquinolinone derivative in accordance with above description (29), wherein $R_5$ is an acyl group composed of a cinnamoyl group which may have a substituent group; and physiologically acceptable salts thereof.

(32) A 7-aminoquinolinone derivative in accordance with above description (30), wherein $R_5$ is an acyl group composed of a cinnamoyl group which may have a substituent group; and physiologically acceptable salts thereof.

(33) A 7-aminoquinolinone derivative in accordance with above description (31), wherein $R_5$ is a 4-hydroxy-3-methoxycinnamoyl group or a 3,5-dimethoxy-4-hydroxycinnamoyl group; and physiologically acceptable salts thereof.

(34) A 7-aminoquinolinone derivative in accordance with above description (32), wherein $R_5$ is a 4-hydroxy-3-methoxycinnamoyl group or a 3,5-dimethoxy-4-hydroxycinnamoyl group; and physiologically acceptable salts thereof.

(35) An anti-allergic agent having as an active ingredient a 7-aminoquinolinone derivative or physiologically acceptable salt thereof in accordance with any one of claims 21 through 34.

(36) A 7-nitroquinolinone derivative expressed by the following general formula (II):

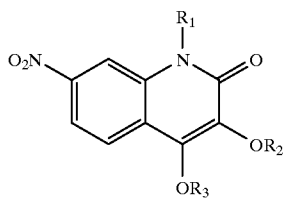

wherein
$R_1$ is a hydrogen atom or an alkyl group;
$R_2$ is a hydrogen atom, an alkyl group, an acyl group or an alkenyl group; and
$R_3$ is a hydrogen atom, an alkyl group or an alkenyl group.

(37) A 7-nitroquinolinone derivative in accordance with above description (36), wherein $R_1$ is a hydrogen atom or a straight-chain or branched-chain alkyl group having 1~10 carbon atoms.

(38) A 7-nitroquinolinone derivative in accordance with above description (36), wherein $R_2$ and $R_3$ are identical or different, and each is a hydrogen atom, a straight-chain or branched-chain alkyl group having 1~10 carbon atoms, or a straight-chain or branched-chain alkenyl group having 2~10 carbon atoms.

(39) A 7-nitroquinolinone derivative in accordance with any one of above description (36) through (38), wherein $R_1$ is a hydrogen atom or a straight-chain or branched-chain alkyl group having 1~10 carbon atoms; $R_2$ and $R_3$ are identical or different, and each is a hydrogen atom, a straight-chain or branched-chain alkyl group having 1~10 carbon atoms, or a straight-chain or branched-chain alkenyl group having 2~10 carbon atoms.

(40) A 7-nitroquinolinone derivative in accordance with above description (39), wherein $R_2$ is an alkyl group having 1~10 carbon atoms, or a straight-chain or branched-chain alkenyl group having 2~10 carbon atoms; and $R_3$ is a hydrogen atom.

(41) A 7-nitroquinolinone derivative in accordance with above description (39), wherein $R_2$ is an acyl group; and $R_3$ is a hydrogen atom, a straight-chain or branched-chain alkyl group having 1~10 carbon atoms, or a straight-chain or branched-chain alkenyl group having 2~10 carbon atoms.

(42) A method of treating allergic diseases of mammals, the method comprising administrating a pathologically effective amount of 7-aminoquinolinone derivative or physiologically acceptable salts thereof as described in one of descriptions (1) through (11).

(43) A method of treating allergic diseases of mammals, the method comprising administrating a pathologically effective amount of 7-aminoquinolinone derivative or physiologically acceptable salts thereof as described in description (12).

(44) A method of treating allergic diseases of mammals, the method comprising administrating a pathologically effective amount of 7-aminoquinolinone derivative or physiologically acceptable salts thereof as described in description (13).

(45) A method of treating allergic diseases of mammals, the method comprising administrating a pathologically effective amount of 7-aminoquinolinone derivative or physiologically acceptable salts thereof as described in description (14).

(46) A method of treating allergic diseases of mammals, the method comprising administrating a pathologically effective amount of 7-aminoquinolinone derivative or physiologically acceptable salts thereof as described in description (15).

(47) A method of treating allergic diseases of mammals, the method comprising administrating a pathologically effective amount of 7-aminoquinolinone derivative or physiologically acceptable salts thereof as described in one of descriptions (21) through (34)

(48) A method of using the 7-nitroquinolinone derivative according to any one of descriptions (34) through (36) to make a 7-aminoquinolinone derivative or physiologically acceptable salts thereof as defined by one of descriptions (1) through (15) and (21) through (34), the method comprising the step of using the 7-nitroquinolinone derivative as an intermediate.

(49) A method of using the 7-nitroquinolinone derivative according to description (37) to make a 7-aminoquinolinone derivative or physiologically acceptable salts thereof as defined by one of descriptions (1) through (15) and (21) through (34), the method comprising the step of using the 7-nitroquinolinone derivative as an intermediate.

(50) A method of using the 7-nitroquinolinone derivative according to one of descriptions (38) and (39) to make a 7-aminoquinolinone derivative or physiologically acceptable salts thereof as defined by one of descriptions (1) through (15) and (21) through (34), the method comprising the step of using the 7-nitroquinolinone derivative as an intermediate.

Thus, the present invention offers new nitroquinolinone derivatives, aminoquinolinone derivatives synthesized from these nitroquinolinone derivatives, and extremely safe anti-allergic agents having these aminoquinolinone derivatives as active ingredients, which are effective against immediate type allergies and delayed type allergies.

DESCRIPTION OF PREFERRED EMBODIMENTS OF THE INVENTION

In the 7-aminoquinolinone derivatives and 7-nitroquinolinone derivatives expressed by general formulas (I) and (II) according to the present invention, $R_1$ denotes a hydrogen atom or an alkyl group, wherein the alkyl group may be a straight-chain alkyl group or a branched-chain alkyl group.

Specific examples of such alkyl groups are methyl groups, ethyl groups, propyl groups, isopropyl groups, n-butyl groups, s-butyl groups, n-pentyl groups, hexyl groups, octyl groups, and decyl groups. The alkyl groups should preferably have 1~10 carbon atoms, more preferably 1~8 carbon atoms.

Additionally, $R_2$ and $R_3$ in general formula (I) denote hydrogen atoms, acyl groups, alkyl groups or alkenyl groups. Examples of acyl groups are benzoyl groups and alkanoyl groups represented by formyl groups, acetyl groups, propionyl groups and butyryl groups. The benzoyl groups may have substituent groups, and examples of such are p-hydroxybenzoyl groups, p-methoxybenzoyl groups, 2,4-dihydroxybenzoyl groups and 2,4-dimethoxybenzoyl groups. Preferably, they should be alkanoyl groups, more preferably acetyl groups.

As alkyl groups, they may be either straight-chain or branched-chain alkyl groups, examples of which include methyl groups, ethyl groups, propyl groups, isopropyl groups, n-butyl groups, s-butyl groups, n-pentyl groups, hexyl groups, octyl groups, and decyl groups. The allyl groups should preferably have 1~10 carbon atoms, more preferably 1~8 carbon atoms.

As alkenyl groups, they may be either straight-chain or branched-chain alkenyl groups, examples of which include vinyl groups, propenyl groups, hexenyl groups, octenyl groups, and geranyl groups. The alkenyl groups should preferably have 2~10 carbon atoms, more preferably 3~8 carbon atoms.

Additionally, $R_4$ and $R_5$ in general formulas (I) and (II) may be identical or different, and denote hydrogen atoms, acyl groups, alkyl groups, alkenyl groups, or aralkyl groups. Examples of acyl groups are alkenoyl groups represented by formyl groups, acetyl groups, propionyl groups and butyryl groups, benzoyl groups, substituted benzoyl groups, and cinnamoyl groups which may be substituted.

Examples of substituted benzoyl groups include p-hydroxybenzoyl groups, p-methoxybenzoyl groups, 2,4-dihydroxybenzoyl groups and 2,4-dimethoxybenzoyl groups. Examples of cinnamoyl groups which may be substituted include cinnamoyl groups, 2-hydroxycinnamoyl groups, 3-hydroxycinnamoyl groups, 4-hydroxycinnamoyl groups, 3,4-dihydroxycinnamoyl groups, 4-hydroxy-3-methoxycinnamoyl groups, 3-hydroxy-4-methoxycinnamoyl groups, and 3,5-dimethoxy-4-hydroxycinnamoyl groups. Preferably, they should be cinnamoyl groups which may be substituted.

If $R_4$ and $R_5$ in general formulas (I) and (II) are alkyl groups, they may be either straight-chain or branched-chain alkyl groups, examples of which include methyl groups, ethyl groups, propyl groups, isopropyl groups, n-butyl groups, s-butyl groups, n-pentyl groups, hexyl groups, octyl groups, and decyl groups. The alkyl groups should preferably have 1~10 carbon atoms, more preferably 1~8 carbon atoms.

As alkenyl groups, they may be either straight-chain or branched-chain alkenyl groups, examples of which include vinyl groups, propenyl groups, hexenyl groups, octenyl groups, and geranyl groups. The alkenyl groups should preferably have 2~10 carbon atoms, more preferably 3~8 carbon atoms.

As examples of aralkyl groups, there are benzyl groups, substituted benzyl groups (such as p-methoxybenzyl groups and p-hydroxybenzyl groups). The present invention includes 7-aminoquinolinone derivatives wherein the substituent groups $R_4$ and $R_5$ in the 7-aminoquinolinone derivatives of general formulas (I) and (II) are identical substituent groups, and 7-aminoquinolinone derivatives comprising a combination of different substituent groups chosen from the above-listed groups.

In the 7-nitroquinolinone derivatives expressed by general formula (II) which are important starting materials for the 7-aminoquinolinone derivatives of the present invention, $R_2$ denotes a hydrogen atom, an acyl group, an alkyl group or an alkenyl group. Examples of acyl groups are benzoyl groups and alkanoyl groups represented by formyl groups, acetyl groups, propionyl groups and butyryl groups. The benzoyl groups may have substituent groups, and examples of such are p-hydroxybenzoyl groups, p-methoxybenzoyl groups, 2,4-dihydroxybenzoyl groups and 2,4-dimethoxybenzoyl groups. Preferably, they should be alkanoyl groups, more preferably acetyl groups.

As alkyl groups, they may be either straight-chain or branched-chain alkyl groups, examples of which include methyl groups, ethyl groups, propyl groups, isopropyl groups, n-butyl groups, s-butyl groups, n-pentyl groups, hexyl groups, octyl groups, and decyl groups. The alkyl groups should preferably have 1~10 carbon atoms, more preferably 1~8 carbon atoms.

As alkenyl groups, they may be either straight-chain or branched-chain alkenyl groups, examples of which include vinyl groups, propenyl groups, hexenyl groups, octenyl groups, and geranyl groups. The alkenyl groups should preferably have 2~10 carbon atoms, more preferably 3~8 carbon atoms.

In general formula (II), $R_3$ denotes a hydrogen atom, an alkyl group or an alkenyl group. Examples of alkyl groups are methyl groups, ethyl groups, propyl groups, isopropyl groups, n-butyl groups, s-butyl groups, n-pentyl groups, hexyl groups, octyl groups, and decyl groups. The alkyl groups should preferably have 1~10 carbon atoms, more preferably 1~8 carbon atoms.

As alkenyl groups, they may be either straight-chain or branched-chain alkenyl groups, examples of which include vinyl groups, propenyl groups, hexenyl groups, octenyl groups, and geranyl groups. The alkenyl groups should preferably have 2~10 carbon atoms, more preferably 3~8 carbon atoms.

The following compounds are illustrative examples of 7-aminoquinolinone derivatives represented by the formula (I) of the present invention. 7-amino-3-acetoxy-4-methoxy-2(1H)-quinolinone, 7-amino-3-acetoxy-4-butoxy-2(1H)-quinolinone, 7-amino-3-acetoxy-4-hexyloxy-2(1H)-quinolinone, 7-amino-3-acetoxy-4-(3-methyl-2-butenyloxy)-2(1H)-quinolinone, 7-amino-3-acetoxy-4-geranyloxy-2(1H)-quinolinone, 7-amino-3-acetoxy-4-hydroxy-2(1H)-quinolinone, 7-amino-3-formyloxy-4-methoxy-2(1H)-quinolinone, 7-amino-4-butoxy-3-formyloxy-2(1H)-quinolinone, 7-amino-3-formyloxy-4-hexyloxy-2(1H)-quinolinone, 7-amino-3-formyloxy-4-(3-methyl-2-butenyloxy)-2(1H)-quinolinone, 7-amino-3-formyloxy-4-geranyloxy-2(1H)-quinolinone, 7-amino-3-formyloxy-4-hydroxy-2(1H)-quinolinone, 7-amino-4-acetoxy-3-methoxy-2(1H)-quinolinone, 7-amino-4-acetoxy-3-butoxy-2(1H)-quinolinone, 7-amino-4-acetoxy-3-hexyloxy -2(1H)-quinolinone, 7-amino-4-acetoxy-3-(3-methyl-2-butenyloxy)-2(1H)-quinolinone, 7-amino-4-acetoxy-3-geranyloxy-2(1H)-quinolinone, 7-amino-4-benzoyloxy-3-methoxy-2(1H)-quinolinone, 7-amino-4-benzoyloxy-3-butoxy-2(1H)-quinolinone, 7-amino-4-benzoyloxy -3-hexyloxy-2(1H)-quinolinone, 7-amino-4-benzoyloxy-3-(3-methyl-2-butenyloxy)-2(1H)-quinolinone, 7-amino -4-benzoyloxy -3-geranyloxy-2(1H)-quinolinone, 7-amino-3,4-dimethoxy-2(1H)-quinolinone, 7-amino-4-butoxy-3-methoxy-2(1H)-quinolinone, 7-amino-4-hexyloxy-3-methoxy-2(1H)-quinolinone, 7-amino-3-methoxy-4-(3-methyl-2-butenyloxy)-2(1H)-quinolinone, 7-amino-4-geranyloxy-3-methoxy-2(1H)-quinolinone, 7-amino-4-hydroxy-3-methoxy-2(1H)-quinolinone, 7-amino-3-isopropoxy-4-methoxy-2(1H)-quinolinone, 7-amino-4-butoxy-3-isopropoxy-2(1H)-quinolinone, 7-amino-4-hexyloxy-3-isopropoxy-2(1H)-quinolinone, 7-amino-3-isopropoxy-4-(3-methyl-2-butenyloxy)-2(1H)-quinolinone, 7-amino-4-geranyloxy-3-isopropoxy-2(1H)-quinolinone, 7-amino -4-hydroxy-3-isopropoxy-2(1H)-quinolinone, 7-amino-3-butoxy-4-methoxy-2(1H)-quinolinone, 7-amino-3,4-dibutoxy-2(1H)-quinolinone, 7-amino-3-butoxy-4-hexyloxy-2(1H)-quinolinone, 7-amino-3-butoxy-4-(3-methyl-2-butenyloxy)-2(1H)-quinolinone, 7-amino-3-butoxy-4-geranyloxy-2(1H)-quinolinone, 7-amino-3-butoxy-4-hydroxy-2(1H)-quinolinone, 7-amino-3-hexyloxy-4-methoxy-2(1H)-quinolinone, 7-amino-4-butoxy-3-hexyloxy-2(1H)-quinolinone, 7amino- 3,4-dihexyloxy-2(1H)-quinolinone, 7-amino-3-hexyloxy-4-(3-methyl-2-butenyloxy)-2(1H)-quinolinone, 7-amino-4-geranyloxy-3-hexyloxy-2(1H)-quinolinone, 7-amino-3-hexyloxy-4-hydroxy-2(1H)-quinolinone, 7-amino-4-methoxy-3-(2-methylpentyloxy)-2(1H)-quinolin e, 7-amino-4-butoxy-3-(2-methylpentyloxy)-2(1H)-quinolinone, 7-amino-4-hexyloxy-3-(2-methylpentyloxy)-2(1H)-quinolinone, 7-amino-4-(3-methyl-2-butenyloxy)-3-(2-methylpentyloxy)-2(1H)-quinolinone, 7-amino-4-geranyloxy-3-(2-methylpentyloxy)-2(1H)-quinolinone, 7-amino-2(1H)-quinolinone, 7-amino-4-butoxy-3-octyloxy-2(1H)-quinolinone, 7-amino-4-hexyloxy-3-octyloxy-2(1H)-quinolinone, 7-amino-4-(3-methyl-2-butenyloxy)-3-octyloxy-2(1H)-quinolinone, 7-amino-4-geranyloxy-3-octyloxy-2(1H)-quinolinone, 7-amino-4-hydroxy-3-octyloxy-2(1H)-quinolinone, 7-amino-4-methoxy-3-(2-propenyloxy)-2(1H)-quinolinone, 7-amino-4-butoxy-3-(2-propenyloxy)-2(1H)-quinolinone, 7-amino-4-hexyloxy-3-(2-propenyloxy)-2(1H)-quinolinone, 7-amino-4-(3-methyl-2-butenyloxy)-3-(2-propenyloxy)-2(1H)-quinolinone, 7-amino-4-geranyloxy-3-(2-propenyloxy)-2(1H)-quinolinone, 7-amino-4-hydroxy-3-(2-propenyloxy)-2(1H)-quinolinone, 7-amino-3-geranyloxy-4-methoxy-2(1H)-quinolinone, 7-amino-4-butoxy-3-geranyloxy-2(1H)-quinolinone, 7-amino-3-geranyloxy-4-hexyloxy-2(1H)-quinolinone, 7-amino-3-geranyloxy-4-(3-methyl-2-butenyloxy)-2(1H)-quinolinone, 7-amino-3,4-digeranyloxy-2(1H)-quinolinone, 7-amino-3-geranyloxy-4-hydroxy-2(1H)-quinolinone, 7-amino-3,4-dihydroxy-2(1H)-quinolinone, 7-amino-3-hydroxy-4-methoxy-2(1H)-quinolinone, 7-amino-4-butoxy-3-hydroxy-2(1H)-quinolinone, 7-amino-4-hexyloxy-3-hydroxy-2(1H)-quinolinone, 7-amino-3-hydroxy-4-(3-methyl-2-butenyloxy)-2(1H)-quinolinone, 7-amino-4-geranyloxy-3-hydroxy-2(1H)-quinolinone, 7-amino-3-acetoxy-4-methoxy-1-methyl-2(1H)-quinolinone, 7-amino-3-acetoxy-4-ethoxy-1-methyl-2(1H)-quinolinone, 7-amino-3-acetoxy-4-butoxy-1-methyl-2(1H)-quinolinone, 7-amino-3-acetoxy-4-hexyloxy-1-methyl-2(1H)-quinolinone, 7-amino 3-acetoxy-4-(3-methyl-2-butenyloxy)-1-methyl-2(1H)-quinolinone, 7-amino-3-acetoxy-4-geranyloxy-1-methyl-2(1H)-quinolinone, 7-amino-3-acetoxy-4-hydroxy-1-methyl-2(1H)-quinolinone, 7-amino-3-formyloxy-4-methoxy-1-methyl-2(1H)-quinolinone, 7-amino-4-butoxy-3-formyloxy-1-methyl-2(1H)-quinolinone, 7-amino-3-formyloxy-4-hexyloxy-1-methyl-2(1H)-quinolinone, 7-amino-3-formyloxy-4-(3-methyl-2-butenyloxy)-1-methyl-2(1H)-quinolinone, 7amino-3-formyloxy-4-geranyloxy-1-methyl-2(1H)-quinolinone, 7-amino-3-formyloxy-4-hydroxy-1-methyl-2(1H)-quinolinone, 7-amino-4-acetoxy-3-methoxy-1-methyl-2(1H)-quinolinone, 7-amino-4-acetoxy-3-butoxy-1-methyl-2(1H)-quinolinone, 7-amino-4-acetoxy-3-hexyloxy-1-methyl-2(1H)-quilinone, 7-amino-4-acetoxy-3-(3-methyl-2-butenyloxy)-1-methyl-2(1H)-quinolinone, 7-amino-4-acetoxy-3-geranyloxy-1-methyl2(1H)-quinolinone, 7-amino-4-benzoyloxy-3-methoxy-1-methyl-2(1H)-quinolinone, 7-amino-4-benzoyloxy-3-butoxy-1-methyl-2(1H)-quinolinone, 7-amino-4-benzoyloxy-3-hexyloxy-1-methyl-2(1H)-quinolinone, 7-amino-4-benzoyloxy-3-(3-methyl-2-butenyloxy)-1-methyl-2(1H)-quinolinone, 7-amino-4-benzoyloxy-3-geranyloxy-1-methyl-2(1H)-quinolinone, 7-amino-3,4-dimethoxy-1-methyl-2(1H)-quinolinone, 7-amino-4-butoxy-3-methoxy-1-methyl-2(1H)-quinolinone, 7-amino-4-hexyloxy-3-methoxy-1-methyl-2(1H)-quinolinone, 7-amino-3-methoxy-4-(3-methyl-2-butenyloxy)-1-methyl-2(1H)-quinolinone, 7-amino-4-geranyloxy-3-methoxy-1-methyl-2(1H)-quinolinone, 7-amino-4-hydroxy-3-methoxy-1-methyl-2(1 (1H)-quinolinone, 7-amino-3-isopropoxy-4-methoxy-1-methyl-2(1H)-quinolinone, 7-amino-4-butoxy-3-isopropoxy-1-methyl-2(1H)-quinolinone, 7-amino-4-hexyloxy-3-isopropoxy-1-methyl-2(1H)-quinolinone, 7-amino-3-isopropoxy-4-(3-methyl-2-butenyloxy)-1-methyl-2(1H)-quinolinone, 7-amino-4-geranyloxy-3-isopropoxy-1-methyl-2(1H)-quinolinone, 7-amino-4-hydroxy-3-isopropoxy-1-methyl-2(1H)-quinolinone, 7-amino-3-butoxy-4-methoxy-1-methyl-2(1H)-quinolinone, 7-amino-3,4-dibutoxy-1-methyl-2(1H)-quinolinone, 7-amino-3butoxy-4-hexyloxy-1-methyl-2(1H)-quinolinone, 7-amino-3-butoxy-4-(3-methyl-2-butenyloxy) 1-methyl-2(1H)-quinolinone, 7-amino-3-butoxy-4-geranyloxy-1-methyl-2(1H)-quinolinone, 7-amino-3-butoxy-4-hydroxy-1-methyl-2(1H)-quinolinone, 7-amino-3-hexyloxy-4-methoxy-1-methyl-2(1H)-quinolinone, 7-amino-4-butoxy-3-hexyloxy-1-methyl-2H)-quinolinone, 7-amino-3,4-dihexyloxy-1-methyl-2(1H)-quinolinone, 7-amino-3-hexyloxy-4-(3-methyl-2-butenyloxy)-1-methyl-2(1H)-quinolinone, 7-amino-4-geranyloxy-3-hexyloxy-1-methyl-2(1H)-quinolinone, 7-amino-3-hexyloxy-4-hydroxy-1-methyl-2(1H)-quinolinone, 7-amino-4-methoxy-3-(2-methylpentyloxy)-1-methyl-2(1H)-quinolinone, 7-amino-4-butoxy-3-(2-methylpentyloxy)-1-methyl-2(1H)-quinolinone, 7-amino-4-hexyloxy-3-(2-methylpentyloxy)-1-methyl-2(1H)-quinolinone, 7-amino-4-(3-methyl-2-butenyloxy)-3-(2-methylpentyloxy)-1-methyl-2(1H)-quinolinone, 7-amino-4-geranyloxy-3-(2-methylpentyloxy)-1-methyl-2(1H)-quinolinone, 7-amino-4-hydroxy-3-(2-methylpentyloxy)-1-methyl-2(1H)-quinolinone, 7-amino-4-methoxy-3-octyloxy-1-methyl-2(1H)-quinolinone, 7-amino-4-butoxy-3-octyloxy-1-methyl-2(1H)-quinolinone, 7-amino-4-hexyloxy-3-octyloxy-1-methyl-2(1H)-quinolinone, 7-amino-4-(3-methyl-2-butenyloxy)-3-octyloxy-1-methyl-2(1H)-quinolinone, 7-amino-4-geranyloxy-3-octyloxy-1-methyl-2(1H)-quinolinone, 7-amino-3-octyloxy-4-hydroxy- 1-methyl-2(1H)-quinolinone, 7-amino-4-methoxy-3-(2-propenyloxy)-1-methyl-2(1H)-quinolinone, 7-amino-4-butoxy-3-(2-propenyloxy)-1-methyl-2(1H)-quinolinone, 7-amino-4-hexyloxy-3-(2-propenyloxy)-1-methyl-2(1H)-quinolinone, 7-amino-4-(3-methyl-2-butenyloxy)-3-(2-propenyloxy)-1-methyl-2(1H)-quinolinone, 7-amino-4-geranyloxy-3-(2-propenyloxy)-1-methyl-2(1H)-quinolinone, 7-amino-4-hydroxy-3-(2-propenyloxy)-1-methyl-2(1H)-quinolinone, 7-amino-3-geranyloxy-4-methoxy-1-methyl-2(1H)-quinolinone, 7-amino-4-butoxy-3-geranyloxy-1-methyl-2(1H)-quinolinone, 7-amino-3-geranyloxy-4-hexyloxy-1-methyl-2(1H)-quinolinone, 7-amino-3-geranyloxy-4-(3-methyl-2-butenyloxy)-1-methyl-2(1H)-quinolinone, 7-amino-3,4-digeranyloxy-1-methyl-2(1H)-quinolinone, 7-amino-3-geranyloxy-4-hydroxy-1-methyl-2(1H)-quinolinone, 7-amino-3-hydroxy-4-methoxy-1-methyl-2(1H)-quinolinone, 7-amino-4-butoxy-3-hydroxy-1-methyl-2(1H)-quinolinone, 7-amino-4-hexyloxy-3-hydroxy-1-methyl-2(1H)-quinolinone, 7-amino-3-hydroxy-4-(3-methyl-2-butenyloxy)-1-methyl-2(1H)-quinolinone, 7-amino-4-geranyloxy-3-hydroxy-1-methyl-2(1H)-quinolinone, 7-amino-3,4-dihydroxy-1-methyl-2(1H)-quinolinone, 7-amino-3-acetoxy-4-methoxy-1-ethyl-2(1H)-quinolinone, 7-amino-3-acetoxy-4-ethoxy-1-ethyl-2(1H)-quinolinone, 7-amino-3-acetoxy-4-butoxy-1-ethyl-2(1H)-quinolinone, 7-amino-3-acetoxy-4-hexyloxy-1-ethyl-2(1H)-quinolinone, 7-amino-3-acetoxy-4-(3-methyl-2-butenyloxy)-1-ethyl-2(1H)-quinolinone, 7-amino-3-acetoxy-4-geranyloxy-1-ethyl-2(1H)-quinolinone, 7-amino-3-acetoxy-4-hydroxy-1-ethyl-2(1H)-quinolinone, 7-amino-3-formyloxy-4-methoxy-1-ethyl-2(1H)-quinolinone, 7-amino-4-butoxy-3-formyloxy-1-ethyl-2(1H)-quinolinone, 7-amino-3-formyloxy-4-hexyloxy-1-ethyl-2(1H)-quinolinone, 7-amino-3-formyloxy-4-(3-methyl-2-butenyloxy)-1-ethyl-2(1H)-quinolinone, 7-amino-3-formyloxy-4-geranyloxy-1-ethyl-2(1H)-quinolinone, 7-amino-3-formyloxy-4-hydroxy-1-ethyl-2(1H)-quinolinone, 7-amino-3,4-dimethoxy-1-ethyl-2(1H)-quinolinone, 7-amino-4-butoxy-3-methoxy-1-ethyl-2(1H)-quinolinone, 7-amino-4-hexyloxy-3-methoxy-1-ethyl-2(1H)-quinolinone, 7-amino-3-methoxy-4-(3-methyl-2-butenyloxy)-1-ethyl-2(1H)-quinolinone, 7-amino-4-geranyloxy-3-methoxy-1-ethyl-2(1H)-quinolinone, 7-amino-4-hydroxy-3-methoxy-1-ethyl-2(1H)-quinolinone, 7-amino-3-isopropoxy-4-methoxy-1-ethyl-2(1H)-quinolinone, 7-amino-4-butoxy-3-isopropoxy-1-ethyl-2(1H)-quinolinone, 7-amino-4-hexyloxy-3-isopropoxy-1-ethyl-2(1H)-quinolinone, 7-amino-3-isopropoxy-4-(3-methyl-2-butenyloxy)-1-ethyl-2(1H)-quinolinone, 7-amino-4-geranyloxy-3-isopropoxy-1-ethyl-2(1H)-quinolinone, 7-amino-4-hydroxy-3-isopropoxy-1-ethyl-2(1H)-quinolinone, 7-amino-3-butoxy-4-methoxy-1-ethyl-2(1H)-quinolinone, 7-amino-3,4-dibutoxy-1-ethyl-2(1H)-quinolinone, 7-amino-3-butoxy-4-hexyloxy-1-ethyl-2(1H)-quinolinone, 7-amino-3-butoxy-4-(3-methyl-2-butenyloxy)-1-ethyl-2(1H)-quinolinone, 7-amino-3-butoxy-4-geranyloxy-1-ethyl-2(1H)-quinolinone, 7-amino-3-butoxy-4-hydroxy-1-ethyl-2(1H)-quinolinone, 7-amino-3-hexyloxy-4-methoxy-1-ethyl-2(1H)-quinolinone, 7-amino-4-butoxy-3-hexyloxy-1-ethyl-2(1H)-quinolinone, 7-amino-3,4-dihexyloxy-1-ethyl-2(1H)-quinolinone, 7-amino-3-hexyloxy-4-(3-methyl-2-butenyloxy)-1-ethyl-2(1H)-quinolinone, 7-amino-4-geranyloxy-3-hexyloxy-1-ethyl-2(1H)-quinolinone, 7-amino-3-hexyloxy-4-hydroxy-1-ethyl-2(1H)-quinolinone, 7-amino-4-methoxy-3-(2-methylpentyloxy)-1-ethyl-2(1H)-quinolinone, 7-amino-4-butoxy-3-(2-methylpentyloxy)-1-ethyl-2(1H)-quinolinone, 7-amino-4-hexyloxy-3-(2-methylpentyloxy)-1-ethyl-2(1H)-quinolinone, 7-amino-4-(3-methyl-2-butenyloxy)-3-(2-methylpentyloxy)-1-ethyl-2(1H)-quinolinone, 7-amino-4-geranyloxy-3-(2-methylpentyloxy)-1-ethyl-2(1H)-quinolinone, 7-amino-4-hydroxy-3-(2-methylpentyloxy)-1-ethyl-2(1H)-quinolinone, 7-amino-4-methoxy-3-octyloxy-1-ethyl-2(1H)-quinolinone, 7-amino-4-butoxy-3-octyloxy-1-ethyl-2(1H)-quinolinone, 7-amino4-hexyloxy-3-octyloxy-1-ethyl-2(1H)-quinolinone, 7-amino-4-(3-methyl-2-butenyloxy)-3-octyloxy-1-ethyl-2(1H)-quinolinone, 7-amino-4-geranyloxy-3-octyloxy-1-ethyl-2(1H)-quinolinone, 7-amino-4-hydroxy-3-octyloxy-1-ethyl-2(1H)-quinolinone, 7-amino-4-methoxy-3-(2-propenyloxy)-1-ethyl-2(1H)-quinolinone, 7-amino-4-butoxy-3-(2-propenyloxy)-1-ethyl-2(1H)-quinolinone, 7-amino-4-hexyloxy-3-(2-propenyloxy)-1-ethyl-2(1H)-quinolinone, 7-amino-4-(3-methyl-2-butenyloxy)-3-(2-propenyloxy)-1-ethyl-2(1H)-quinolinone, 7-amino-4-geranyloxy-3-(2-propenyloxy)-1-ethyl-2(1H)-quinolinone, 7-amino-4-hydroxy-3-(2-propenyloxy)-1-ethyl-2(1H)-quinolinone, 7-amino-3-geranyloxy-4-methoxy-1-ethyl-2(1H)-quinolinone, 7-amino-4-butoxy-3-geranyloxy-1-ethyl-2(1H)-quinolinone, 7-amino-3-geranyloxy-4-hexyloxy-1-ethyl-2(1H)-quinolinone, 7-amino-3-geranyloxy-4-(3-methyl-2-butenyloxy)-1-ethyl-2(1H)-quinolinone, 7-amino-3,4-digeranyloxy-1-ethyl-2(1H)-quinolinone, 7-amino-3-geranyloxy-4-hydroxy-1-ethyl-2(1H)-quinolinone, 7-amino-3-hydroxy-4-methoxy-1-ethyl-2(1H)-quinolinone, 7-amino-4-butoxy-3-hydroxy-1-ethyl-2(1H)-quinolinone, 7-amino-4-hexyloxy-3-hydroxy-1-ethyl-2(1H)-quinolinone, 7-amino-3-hydroxy-4-(3-methyl-2-butenyloxy)-1-ethyl-2(1H)-quinolinone, 7-amino-4-geranyloxy-3-hydroxy-1-ethyl-2(1H)-quinolinone, 7-amino-3,4-dihydroxy-1-ethyl-2(1H)-quinolinone, 7-amino-3-hydroxy-4-methoxy-1-propyl-2(1H)-quinolinone, 7-amino-3-hydroxy-4-propoxy-1-propyl-2(1H)-quinolinone, 7-amino-4-butoxy-3-hydroxy-1-propyl-2(1H)-quinolinone, 7-amino-4-decyloxy-3-hydroxy-1-propyl-2(1H)-quinolinone, 7-amino-3-acetoxy-4-methoxy-1-butyl-2(1H)-quinolinone, 7-amino-3-acetoxy-4-ethoxy-1-butyl-2(1H)-quinolinone, 7-amino-3-acetoxy-1-butoxyl-1-butyl-2(1H)-quinolinone, 7-amino-3-acetoxy-4-hexyloxy-1-butyl-2(1H)-quinolinone, 7-amino-3-acetoxy-4-(3-methyl-2-butenyloxy)-1-butyl-2(1H)-quinolinone, 7-amino-3-acetoxy-4-geranyloxy-1-butyl-2(1H)-quinolinone, 7-amino-3-acetoxy-4-hydroxy-1-butyl-2(1H)-quinolinone, 7-amino-3-formyloxy-4-methoxy-1-butyl-2(1H)-quinolinone, 7-amino-4-butoxy-3-formyloxy-1-butyl-2(1H)-quinolinone, 7-amino-3-formyloxy-4-hexyloxy-1-butyl-2(1H)-quinolinone, 7-amino-3-formyloxy-4-(3-methyl-2-butenyloxy)-1-butyl-2(1H)-quinolinone, 7-amino-3-formyloxy-4-geranyloxy-1-butyl-2(1H)-quinolinone, 7-amino-3-formyloxy-4-hydroxy-1-butyl-2(1H)-quinolinone, 7-amino-3,4-dimethoxy-1-butyl-2(1H)-quinolinone, 7-amino-4-butoxy-3-methoxy-1-butyl-2(1H)-quinolinone, 7-amino-4-hexyloxy-3-methoxy-1-butyl-2(1H)-quinolinone, 7-amino-3-methoxy-4-(3-methyl-2-butenyloxy)-1-butyl-2(1H)-quinolinone, 7-amino-4-geranyloxy-3-methoxy-1-butyl-2(1H)-quinolinone, 7-amino-4-hydroxy-3-methoxy-1-butyl-2(1H)-quinolinone, 7-amino-3-isopropoxy-4-methoxy-1-butyl-2(1H)-quinolinone, 7-amino-4-butoxy-3-isopropoxy-1-butyl-2(1H)-quinolinone, 7-amino-4-hexyloxy-3-isopropoxy-1-butyl-2(1H)-quinolinone, 7-amino-3-isopropoxy-4-(3-methyl-2-butenyloxy)-1-butyl-2(1H)-quinolinone, 7-amino-4-geranyloxy-3-isopropoxy-1-butyl-2(1H)-quinolinone, 7-amino-4-hydroxy-3-isopropoxy-1-butyl-2(1H)-quinolinone, 7-amino-3-butoxy-4-methoxy-1-butyl-2(1H)-quinolinone, 7-amino-3,4-dibutoxy-1-butyl-2(1H)-quinolinone, 7-amino-3-butoxy-4-hexyloxy-1-butyl-2(1H)-quinolinone, 7-amino-3-butoxy-4-(3-methyl-2-butenyloxy)-1-butyl-2(1H)-quinolinone, 7-amino-3-butoxy-4-geranyloxy-1-butyl-2(1H)-quinolinone, 7-amino-3-butoxy-4-hydroxy-1-butyl-2(1H)-quinolinone, 7-amino-3-hexyloxy-4-methoxy-1-butyl-2(1H)-quinolinone, 7-amino-4-butoxy-3-hexyloxy-1-butyl-2(1H)-quinolinone, 7-amino-3,4-dihexyloxy-1-butyl-2(1H)-quinolinone, 7-amino-3-hexyloxy-4-(3-methyl-2-butenyloxy)-1-butyl-2(1H)-quinolinone, 7-amino-4-geranyloxy-3-hexyloxy-1-butyl-2(1H)-quinolinone, 7-amino-3-hexyloxy-4-hydroxy-1-butyl-2(1H)-quinolinone, 7-amino-4-methoxy-3-(2- methylpentyloxy)-1-butyl-2(1H)-quinolinone, 7-amino-4-butoxy-3-(2-methylpentyloxy)-1-butyl-2(1H)-quinolinone, 7-amino-4-hexyloxy-3-(2-methylpentyloxy)-1-butyl-2(1H)-quinolinone, 7-amino-4-(3-methyl-2-butenyloxy)-3-(2-methylpentyloxy)-1-butyl-2(1H)-quinolinone, 7-amino-4-geranyloxy-3-(2-methylpentyloxy)-1-butyl-2(1H)-quinolinone, 7-amino-4-hydroxy-3-(2-methylpentyloxy)-1-butyl-2(1H)-quinolinone, 7-amino-4-methoxy-3-octyloxy-1-butyl-2(1H)-quinolinone, 7-amino-4-butoxy-3-octyloxy-1-butyl-2(1H)-quinolinone, 7-amino-4-hexyloxy-3-octyloxy-1-butyl-2(1H)-quinolinone, 7-amino-4-(3-methyl-2-butenyloxy)-3-octyloxy-1-butyl-2(1H)-quinolinone, 7-amino-4-geranyloxy-3-octyloxy-1-butyl-2(1H)-quinolinone, 7-amino-3-octyloxy-4-hydroxy-1-butyl-2(1H)-quinolinone, 7-amino-4-methoxy-3-(2-propenyloxy)-1-butyl-2(1H)-quinolinone, 7-amino-4-butoxy-3-(2-propenyloxy)-1-butyl-2(1H)-quinolinone, 7-amino-4-hexyloxy-3-(2-propenyloxy)-1-butyl-2(1H)-quinolinone, 7-amino-4-(3-methyl-2-butenyloxy)-3-(2-propenyloxy)-1-butyl-2(1H)-quinolinone, 7-amino-4-geranyloxy-3-(2-propenyloxy)-1-butyl-2(1H)-quinolinone, 7-amino-4-hydroxy-3-(2-propenyloxy)-1-butyl-2(1H)-quinolinone, 7-amino-3-geranyloxy-4-methoxy-1-butyl-2(1H)-quinolinone, 7-amino-4-butoxy-3-geranyloxy-1-butyl-2(1H)-quinolinone, 7-amino-3-geranyloxy-4-hexyloxy-1-butyl-2(1H)-quinolinone, 7-amino-3-geranyloxy-4-(3-methyl-2-butenyloxy)-1-butyl-2(1H)-quinolinone, 7-amino-3,4-digeranyloxy-1-butyl-2(1H)-quinolinone, 7-amino-3-geranyloxy-4-hydroxy-1-butyl-2(1H)-quinolinone, 7-amino-3-hydroxy-4-methoxy-1-butyl-2(1H)-quinolinone, 7-amino-4-butoxy-3-hydroxy-1-butyl-2(1H)-quinolinone, 7-amino-4-hexyloxy-3-hydroxy-1-butyl-2(1H)-quinolinone, 7-amino-3-hydroxy-4-(3-methyl-2-butenyloxy)-1-butyl-2(1H)-quinolinone, 7-amino-4-geranyloxy-3-hydroxy-1-butyl-2(1H)-quinolinone, 7-amino-3,4-dihydroxy-1-butyl-2(1H)-quinolinone, 7-amino-3-acetoxy-4-methoxy-1-hexyl-2(1H)-quinolinone, 7-amino-3-acetoxy-4-ethoxy-1-hexyl-2(1H)-quinolinone, 7-amino-3-acetoxy-4-butoxy-1-hexyl-2(1H)-quinolinone, 7-amino-3-acetoxy-4-hexyloxy-1-hexyl-2(1H)-quinolinone, 7-amino-3-acetoxy-4-(3-methyl-2-butenyloxy)-1-hexyl-2(1H)-quinolinone, 7-amino-3-acetoxy-4-geranyloxy-1-hexyl-2(1H)-quinolinone, 7-amino-3-acetoxy-4-hydroxy-1-hexyl-2(1H)-quinolinone, 7-amino-3-formyloxy-4-methoxy-1-hexyl-2(1H)-quinolinone, 7-amino-4-butoxy-3-formyloxy-1-hexyl-2(1H)-quinolinone, 7-amino-3-formyloxy-4-hexyloxy-1-hexyl-2(1H)-quinolinone, 7-amino-3-formyloxy-4-(3-methyl-2-butenyloxy)-1-hexyl-2(1H)-quinolinone, 7-amino-3-formyloxy-4-geranyloxy-1-hexyl-2(1H)-quinolinone, 7-amino-3-formyloxy-4-hydroxy-1-hexyl-2(1H)-quinolinone, 7-amino-3,4-dimethoxy-1-hexyl-2(1H)-quinolinone, 7-amino-4-butoxy-3-methoxy-1-hexyl-2(1H)-quinolinone, 7-amino-3-methoxy-4-(3-methyl-2-butenyloxy)-1-hexyl-2(1H)-quinolinone, 7-amino-4-geranyloxy-3-methoxy-1-hexyl-2(1H)-quinolinone, 7-amino-4-hydroxy-3-methoxy-1-hexyl-2(1H)-quinolinone, 7-amino-3-isopropoxy-4-methoxy-1-hexyl-2(1H)-quinolinone, 7-amino-4-butoxy-3-isopropoxy-1-hexyl-2(1H)-quinolinone, 7-amino-4-hexyloxy-3-isopropoxy-1-hexyl-2(1H)-quinolinone, 7-amino-3-isopropoxy-4-(3-methyl-2-butenyloxy)-1-hexyl-2(1H)-quinolinone, 7-amino-4-geranyloxy-3-isopropoxy-1-hexyl-2(1H)-quinolinone, 7-amino-4-hydroxy-3-isopropoxy-1-hexyl-2(1H)-quinolinone, 7-amino-3-butoxy-4-methoxy-1-hexyl-2(1H)-quinolinone, 7-amino-3,4-dibutoxy-1-hexyl-2(1H)-quinolinone, 7-amino-3-butoxy-4-hexyloxy-1-hexyl-2(1H)-quinolinone, 7-amino-3-butoxy-4-(3-methyl-2-butenyloxy)-1-hexyl-2(1H)-quinolinone, 7-amino-3-butoxy-4-geranyloxy-1-hexyl-2(1H)-quinolinone, 7-amino-3-butoxy-4-hydroxy-1-hexyl-2(1H)-quinolinone, 7-amino-3-hexyloxy-4-methoxy-1-hexyl-2(1H)-quinolinone, 7-amino-4-butoxy-3-hexyloxy-1-hexyl-2(1H)-quinolinone, 7-amino-3,4-dihexyloxy-1-hexyl-2(1H)-quinolinone, 7-amino-3-hexyloxy-4-(3-methyl-2-butenyloxy)-1-hexyl-2(1H)-quinolinone, 7-amino-4-geranyloxy-3-hexyloxy-1-hexyl-2(1H)-quinolinone, 7-amino-3-hexyloxy-4-hydroxy-1-hexyl-2(1H)-quinolinone, 7-amino-4-methoxy-3-(2-methylpentyloxy)-1-hexyl-2(1H)-quinolinone, 7-amino-4-butoxy-3-(2-methypentyloxy)-1-hexyl-2(1H)-quinolinone, 7-amino-4-hexyloxy-3-(2-methylpentyloxy)-1-hexyl-2(1H)-quinolinone, 7-amino-4-(3-methyl-2-butenyloxy)-3-(2-methylpentyloxy)-1-hexyl-2(1H)-quinolinone, 7-amino-4-geranyloxy-3-(2-methylpentyloxy)-1-hexyl-2(1H)-quinolinone, 7-amino-4-hydroxy-3-(2-methylpentyloxy)-1-hexyl-2(1H)-quinolinone, 7-amino-4-methoxy-3-octyloxy-1-hexyl-2(1H)-quinolinone, 7-amino-4-butoxy-3-octyloxy-1-hexyl-2(1H)-quinolinone, 7-amino-4-hexyloxy-3-octyloxy-1-hexyl-2(1H)-quinolinone, 7-amino-4-(3-methyl-2-butenyloxy)-3-octyloxy-1-hexyl-2(1H)-quinolinone, 7-amino-4-geranyloxy-3-octyloxy-1-hexyl-2(1H)-quinolinone, 7-amino-4-hydroxy-3-octyloxy-1-hexyl-2(1H)-quinolinone, 7-amino-4-methoxy-3-(2-propenyloxy)-1-hexyl-2(1H)-quinolinone, 7-amino-4-butoxy-3-(2-propenyloxy)-1-hexyl-2(1H)-quinolinone, 7-amino-4-hexyloxy-3-(2-propenyloxy)-1-hexyl-2(1H)-quinolinone, 7-amino-4-(3-methyl-2-butenyloxy)-3-(2-propenyloxy)-1-hexyl-2(1H)-quinolinone, 7-amino-4-geranyloxy-3-(2-propenyloxy)-1-hexyl-2(1H)-quinolinone, 7-amino-4-hydroxy-3-(2-propenyloxy)-1-hexyl-2(1H)-quinolinone, 7-amino-3-geranyloxy-4-methoxy-1-hexyl-2(1H)-quinolinone, 7-amino-4-butoxy-3-geranyloxy-1-hexyl-2(1H)-quinolinone, 7-amino-3-geranyloxy-4-hexyloxy-1-hexyl-2(1H)-quinolinone, 7-amino-3-geranyloxy-4-(3-methyl-2-butenyloxy)-1-hexyl-2(1H)-quinolinone, 7-amino-3-geranyloxy-4-hydroxy-1-hexyl-2(1H)-quinolinone, 7-amino-3,4-digeranyloxy-1-hexyl-2(1H)-quinolinone, 7-amino-3-hydroxy-4-methoxy-1-hexyl-2(1H)-quinolinone, 7-amino-4-butoxy-3-hydroxy-1-hexyl-2(1H)-quinolinone, 7-amino-4-hexyloxy-3-hydroxy-1-hexyl-2(1H)-quinolinone, 7-amino-3-hydroxy-4-(3-methyl-2-butenyloxy)-1-hexyl-2(1H)-quinolinone, 7-amino-4-geranyloxy-3-hydroxy-1-hexyl-2(1H)-quinolinone, 7-amino-3,4-dihydroxy-1-hexyl-2(1H)-quinolinone, 7-amino-3-acetoxy- 4-methoxy-1-octyl-2(1H)-quinolinone, 7-amino-3-acetoxy-4-ethoxy-1-octyl-2(1H)-quinoline, 7-amino-3-acetoxy-4-butoxy-1-octyl-2(1H)-quinolinone, 7-amino-3-acetoxy-4-hexyloxy-1-octyl-2(1H)-quinolinone, 7-amino-3-acetoxy-4-(3-methyl-2-butenyloxy)-1-octyl-2(1H)-quinolinone, 7-amino-3-acetoxy-4-geranyloxy-1-octyl-2(1H)-quinolinone, 7-amino-3-acetoxy-4-hydroxy-1-octyl-2(1H)-quinolinone, 7-amino-3-formyloxy-4-methoxy-1-octyl-2(1H)-quinolinone, 7-amino-4-butoxy-3-formyloxy-1-octyl-2(1H)-quinolinone, 7-amino-3-formyloxy-4-hexyloxy-1-octyl-2(1H)-quinolinone, 7-amino-3-formyloxy-4-(3-methyl-2-butenyloxy)-1-octyl-2(1H)-quinolinone, 7-amino-3-formyloxy-4-geranyloxy-1-octyl-2(1H)-quinolinone, 7-amino-3-formyloxy-4-hydroxy-1-octyl-2(1H)-quinolinone, 7-amino-3,4-dimethoxy-1-octyl-2(1H)-quinolinone, 7-amino-4-butoxy-3-methoxy-1-octyl-2(1H)-quinolinone, 7-amino-4-hexyloxy-3-methoxy-1-octyl-2(1H)-quinolinone, 7-amino-3-methoxy-4-(3-methyl-2-butenyloxy)-1-octyl-2(1H)-quinolinone, 7-amino-4-geranyloxy-3-methoxy-1-octyl- 2(1H)-quinolinone, 7-amino-4-hydroxy-3-methoxy-1-octyl-2(1H)-quinolinone, 7-amino-3-hexyloxy-4-hydroxy-1-octyl-2(1H)-quinolinone, 7-amino-3-isopropoxy-4-methoxy-1-octyloxy-2(1H)-quinolinone, 7-amino-4-butoxy-3-isopropoxy-1-octyl-2(1H)-quinolinone, 7-amino-4-hexyloxy-3-isopropoxy-1-octyl-2(1H)-quinolinone, 7-amino-3-isopropoxy-4-(3-methyl-2-butenyloxy)-1-octyl-2(1H)-quinolinone, 7-amino-4-geranyloxy-3-isopropoxy-1-octyl-2(1H)-quinolinone, 7-amino-4-hydroxy-3-isopropoxy-1-octyl-2(1H)-quinolinone, 7-amino-3-butoxy-4-methoxy-1-octyl-2(1H)-quinolinone, 7-amino-3,4-dibutoxy-1-octyl-2(1H)-quinolinone, 7-amino-3-butoxy-4-hexyloxy-1-octyl-2(1H)-quinolinone, 7-amino-3-butoxy-4-geranyloxy-1-octyl-2(1H)-quinolinone, 7-amino-3-butoxy-4-hydroxy-1-octyl-2(1H)-quinolinone, 7-amino-3-hexyloxy-4-methoxy-1-octyl-2(1H)-quinolinone, 7-amino-4-butoxy-3-hexyloxy-1-octyl-2(1H)-quinolinone, 7-amino-3,4-dihexyloxy-1-octyl-2(1H)-quinolinone, 7-amino-3-hexyloxy-4-(3-methyl-2-butenyloxy)-1-octyl-2(1H)-quinolinone, 7-amino-4-geranyloxy-3-hexyloxy-1-octyl-2(1H)-quinolinone, 7-amino-3-hexyloxy-4-hydroxy-1-octyl-2(1H)-quinolinone, 7-amino-4-methoxy-3-(2-methylpentyloxy)-1-octyl-2(1H)-quinolinone, 7-amino-4-butoxy-3-(2-methyl-1pentyloxy)-1-octyl-2(1H)-quinolinone, 7-amino-4-hexyloxy-3-(2-methylpentyloxy)-1-octyl-2(1H)-quinolinone, 7-amino-4-(3-methyl-2-butenyloxy)-3-(2-methyl-pentyloxy)-1-octyl-2(1H)-quinolinone, 7-amino-4-geranyloxy-3-(2-methyl-pentyloxy)-1-octyl-2(1H)-quinolinone, 7-amino-4-hydroxy-3-(2-methylpentyloxy)-1-octyl-2(1H)-quinolinone, 7-amino-4-methoxy-3-octyloxy-1-octyl-2(1H)-quinolinone, 7-amino-4-butoxy-3-octyloxy-1-octyl-2(1H)-quinolinone, 7-amino-4-hexyloxy-3-octyloxy-1-octyl-2(1H)-quinolinone, 7-amino-4-(3-methyl-2-butenyloxy)-3-octyloxy-1-octyl-2(1H)-quinolinone, 7-amino-4-geranyloxy-3-octyloxy-1-octyl-2(1H)-quinolinone, 7-amino-4-hydroxy-3-octyloxy-1-octyl-2(1H)-quinolinone, 7-amino-4-methoxy-3-(2-propenyloxy)-1-octyl-2(1H)-quinolinone, 7-amino-4-butoxy-3-(2-propenyloxy)-1-octyl-2(1H)-quinolinone, 7-amino-4-hexyloxy-3-(2-propenyloxy)-1-octyl-2(1H)-quinolinone, 7-amino-4-(3-methy-2-butenyloxy)-3(2-propenyloxy)-1-octyl-2(1H)-quinolinone, 7-amino-4-geranyloxy-3-(2-propenyloxy)-1-octyl-2(1H)-quinolinone, 7-amino-4-hydroxy-3-(2-propenyloxy)-1-octyl-2(1H)-quinolinone, 7-amino-3-geranyloxy-4-methoxy-1-octyl-2(1H)-quinolinone, 7-amino-4-butoxy-3-geranyloxy-1-octyl-2(1H)-quinolinone, 7-amino-3-geranyloxy-4-hexyloxy-1-octyl-2(1H)-quinolinone, 7-amino-3-geranyloxy-4-(3-methyl-2-butenyloxy)-1-octyl-2(1H)-quinolinone, 7-amino-3,4-digeranyloxy-1-octyl-2(1H)-quinolinone, 7-amino-3-geranyloxy-4-hydroxy-1-octyl-2(1H)-quinolinone, 7-amino-3-hydroxy-4-methoxy-1-octyl-2(1H)-quinolinone, 7amino-4-butoxy-3-hydroxy-1-octyl-2(1H)-quinolinone, 7-amino-4-hexyloxy-3-hydroxy-1-octyl-2(1H)-quinolinone, 7-amino-3-hydroxy-4-(3-methyl-2-butenyloxy)-1-octyl-2(1H)-quinolinone, 7-amino-4-geranyloxy-3-hydroxy-1-octyl-2(1H)-quinolinone, 7-amino-3, 4-hydroxy-1-octyl-2(1H)-quinolinone, 7-methylamino-3-acetoxy-4-methoxy-2(1H)-quinolinone, 7-methylamino-3-acetoxy-4-butoxy-2(1H)-quinolinone, 7-methylamino-3-acetoxy-4-hexyloxy-2(1H)-quinolinone, 7-methylamino-3-acetoxy-4-(3-methyl-2-butenyloxy)-2(1H)-quinolinone, 7-methylamino-3-acetoxy-4-geranyloxy-2(1H)-quinolinone, 7-methylamino-3-acetoxy-4-hydroxy-2(1H)-quinolinone, 7-methylamino-3-formyloxy-4-methoxy-2(1H)-quinolinone, 7-methylamino-4-butoxy-3-formyloxy-2(1H)-quinolinone, 7-methylamino-3-formyl-oxy-4-hexyloxy-2(1H)-quinolinone, 7-methylamino-3-formyloxy-4-(3-methyl-2-butenyloxy)-2 (1H)-quinolinone, 7-methylamino-3-formyloxy-4-geranyloxy-2(1H)-quinolinone, 7-methylamino-3-formyloxy-4-hydroxy-2(1H)-quinolinone, 7-methylamino-3,4-dimethoxy-2(1H)-quinolinone, 7-methylamino-4-butoxy-3-methoxy-2(1H)-quinolinone, 7-methylamino-4-hexyloxy-3-methoxy-2(1H)-quinolinone, 7-methylamino-3-methoxy-4-(3-methyl-2-butenyloxy)-2(1H)-quinolinone, 7-methylamino-4-geranyloxy-3-methoxy-2(1H)-quinolinone, 7-methylamino-4-hydroxy-3-methoxy-2(1H)-quinolinone, 7-methylamino-3-(2-propenyloxy)-4-hydroxy-1-ethyl-2(1H)-quinolinone, 7-methylamino-3-isopropoxy-4-methoxy-2(1H)-quinolinone, 7-methylamino-4-butoxy-3-isopropoxy-2(1H)-quinolinone, 7-methylamino-4-hexyloxy-3-isopropoxy-2(1H)-quinolinone, 7-methylamino-3-isopropoxy-4-(3-methyl-2-butenyloxy)-2(1H)-quinolinone, 7-methylamino-4-geranyloxy-3-isopropoxy-2(1H)-quinolinone, 7-methylamino-4-hydroxy-3-isopropoxy-2(1H)-quinolinone, 7-methylamino-3-butoxy-4-methoxy-2(1H)-quinolinone, 7-methyl-amino-3-acetoxy-4-methoxy-1-methyl-2(1H)-quinolinone, 7-methylamino-3-hydroxy-4-methoxy-1-methyl-2(1H)-quinolinone, 7-methylamino-3-hydroxy-4-octyloxy-1-methyl-2(1H)-quinolinone, 7-methylamino-4-hydroxy-3-prenyloxy-1-methyl-2(1H)-quinolinone, 7-methylamino-3-geranyloxy-4-hydroxy-1-methyl-2(1H)-quinolinone, 7-methylamino-4-hydroxy-3-(2-propenyloxy)-1-methyl-2(1H)-quinolinone, 7-methylamino-4-hydroxy-3-prenyloxy-1-butyl-2(1H)-quinolinone, 7-methylamino-3-hydroxy-4-prenyloxy-1-butyl-2(1H)-quinolinone, 7-methylamino-4-hydroxy-3-prenyloxy-1-butyl-2(1H)-quinolinone, 7-methylamino-3-hydroxy-4-prenyloxy-1-butyl-2(1H)-quinolinone, 7-ethylamino-3,4-dibutoxy-2(1H)-quinolinone, 7-ethylamino-3-butoxy-4-hexyloxy-2(1H)-quinolinone, 7-ethylamino-3-butoxy-4-(3-methyl-2-butenyloxy)-2(1H)-quinolinone, 7-ethylamino-3-butoxy-4-geranyloxy-2(1H)-quinolinone, 7-ethylamino-3-butoxy-4-hydroxy-2(1H)-quinolinone, 7-ethylamino-3-hexyloxy-4-methoxy-2(1H)-quinolinone, 7-ethylamino-4-butoxy-3-hexyloxy-2(1H)-quinolinone, 7-ethylamino-3,4-dihexyloxy-2(1H)-quinolinone, 7-ethylamino-3-hexyloxy-4-(3-methyl-2-butenyloxy)-2(1H)-quinolinone, 7-ethylamino-4-geranyloxy-3-hexyloxy-2(1H)-quinolinone, 7-ethylamino-3-hexyloxy-4-hydroxy-2(1H)-quinolinone, 7-ethylamino-4-methoxy-3-(2-methylpentyloxy)-2(1H)-quinolinone, 7-ethylamino-4-butoxy-3-(2-methylpentyloxy)-2(1H)-quinolinone, 7-ethylamino-4-hexyloxy-3-(2-methylpentyloxy)-2(1H)-quinolinone, 7-ethylamino-4-(3-methyl-2-butenyloxy)-3-(2-methyl-pentyloxy)-2(1H)-quinolinone, 7-ethylamino-4-geranyloxy-3-(2-methylpentyloxy)-2(1H)-quinolinone, 7-ethylamino-4-hydroxy-3-(2-methylpentyloxy)-2(1H)-quinolinone, 7-ethylamino-4-methoxy-3-octyloxy-2(1H)-quinolinone, 7-ethylamino-4-butoxy-3-octyloxy-2(1H)-quinolinone, 7-ethylamino-4-hexyloxy-3-octyloxy-2(1H)-quinolinone, 7-ethylamino-4-(3-methyl-2-butenyloxy)-3-octyloxy-2(1H)-quinolinone, 7-ethylamino-4-geranyloxy-3-octyloxy-2(1H)-quinolinone, 7-ethylamino-4-hydroxy-3-octyloxy-2(1H)-quinolinone, 7-ethylamino-4-methoxy-3-(2-propenyloxy)-2(1H)-quinolinone, 7-ethylamino-4-butoxy-3-(2-propenyloxy)-2(1H)-quinolinone, 7-ethylamino-4-hexyloxy-3-(2-propenyloxy)-2(1H)-quinolinone, 7-dimethylamino-4-(3-methyl-2-butenyloxy)-3-(2-propenyloxy)-2(1H)-quinolinone, 7-dimethylamino-4-geranyloxy-3-(2-propenyloxy)-2(1H)-quinolinone, 7-dimethyl-amino-4-hydroxy-3-(2-propenyloxy)-2(1H)-quinolinone, 7-dimethylamino-3-geranyloxy-4-methoxy-2(1H)-quinolinone, 7-dimethylamino-4-butoxy-3- geranyloxy-2(1H)-quinolinone, 7-dimethylamino-3-geranyloxy-4-hexyloxy-2(1H)-quinolinone, 7-dimethylamino-3-geranyloxy-4-(3-methyl-2-butenyloxy)-2(1H)-quinolinone, 7-dimethylamino-3,4-digeranyloxy-2(1H)-quinolinone, 7-dimethylamino-3-geranyloxy-4-hydroxy-2(1H)-quinolinone, 7-dimethylamino-3-hydroxy-4-methoxy-2(1H)-quinolinone, 7-dimethylamino-4-butoxy-3-hydroxy-2(1H)-quinolinone, 7-dimethylamino-4-hexyloxy-3-hydroxy-2(1H)-quinolinone, 7-dimethylamino-3-hydroxy-4-(3-methyl-2-butenyloxy)-2(1H)-quinolinone, 7-dimethylamino-4-geranyloxy-3-hydroxy-2(1H)-quinolinone, 7-dimethylamino-3,4-dihydroxy-2(1H)-quinolinone, 7-dimethylamino-3-acetoxy-4-methoxy-1-methyl-2(1H)-quinolinone, 7-dimethylamino-3-acetoxy-4-butoxy-1-methyl-2(1H)-quinolinone, 7-dimethylamino-3-acetoxy-4-hexyloxy-1-methyl-2(1H)-quinolinone, 7-dimethylamino-3-acetoxy-4-(3-methyl-2-butenyloxy)-1-methyl-2(1H)-quinolinone, 7-dimethylamino-3-acetoxy-4-geranyloxy-1-methyl-2(1H)-quinolinone, 7-dimethylamino-3-acetoxy-4-hydroxy-1-methyl-2(1H)-quinolinone, 7-dimethylamino-3-formyloxy-4-methoxy-1-methyl-2(1H)-quinolinone, 7-dimethylamino-4-butoxy-3-formyloxy-1-methyl-2(1H)-quinolinone, 7-dimethylamino-3-formyloxy-4-hexyloxy-1-methyl-2(1H)-quinolinone, 7-dimethylamino-3-formyloxy-4-(3-methyl-2-butenyloxy)-1-methyl-2(1H)-quinolinone, 7-dimethylamino-3-formyloxy4-geranyloxy-1-methyl-2(1H)-quinolinone, 7-dimethylamino-3-formyloxy-4-hydroxy-1-methyl-2(1H)-quinolinone, 7-dimethylamino-3,4-dimethoxy-1-methyl-2(1H)-quinolinone, 7-dimethylamino-3-hexyloxy-4-hydroxy-1-methyl-2(1H)-quinolinone, 7-dimethylamino-4-butoxy-3-methoxy-1-methyl-2(1H)-quinolinone, 7-dimethylamino-4-hexyloxy-3-hydroxy-1-methyl-2(1H)-quinolinone, 7-dimethylamino-3-hydroxy-4-methoxy-1-butyl-2(1H)-quinolinone, 7-dimethylamino-3-hexyloxy-4-hydroxy-1-butyl-2(1H)-quinolinone, 7-dimethylamino-3-hydroxy-4-methoxy-1-butyl-2(1H)-quinolinone, 7-butylamino-3-acetoxy-4-methoxy-2(1H)-quinolinone, 7-butylamino-3-hydroxy-4-methoxy-2(1H)-quinolinone, 7-butylamino-4-hexyloxy-3-methoxy-1-methyl-2(1H)-quinolinone, 7-butylamino-3-acetoxy-4-methoxy-2(1H)-quinolinone, 7-butylamino-3-hydroxy-4-methoxy-2(1H)-quinolinone, 7-butylamino-3-methoxy-4-(3-methyl-2-butenyloxy)-1-methyl-2(1H)-quinolinone, 7-butylamino-4-geranyloxy-3-methoxy-1-methyl-2(1H)-quinolinone, 7-butylamino-4-hydroxy-3-methoxy-1-methyl-2(1H)-quinolinone, 7-butylamino-4-hexyloxy-3-hydroxy-1-methyl-2(1H)-quinolinone, 7-butylamino-3-isopropoxy-4-methoxy-1-methyl-2(1H)-quinolinone, 7-butylamino-4-butoxy-3-isopropoxy-1-methyl-2(1H)-quinolinone, 7-butylamino-4-hexyloxy-3-isopropoxy-1-methyl-2(1H)-quinolinone, 7-butylamino-3-isopropoxy-4-(3-methyl-2-butenyloxy)- 1-methyl-2(1H)-quinolinone, 7-butylamino-4-geranyloxy-3-isopropoxy-1-methyl-2(1H)-quinolinone, 7-butylamino-4-hydroxy-3-isopropoxy-1-methyl-2(1H)-quinolinone, 7-butylamino-3-butoxy-4-methoxy-1-methyl-2(1H)-quinolinone, 7-butylamino-3,4-dibutoxy-1-methyl-2(1H)-quinolinone, 7-butylamino-3-butoxy-4-hexyloxy-1-methyl-2(1H)-quinolinone, 7-butylamino-3-butoxy-4-(3-methyl-2-butenyloxy)-1-methyl-2(1H)-quinolinone, 7-butylamino-3-butoxy-4-geranyloxy-1-methyl-2(1H)-quinolinone, 7butylamino-3-butoxy-4-hydroxy-1-methyl-2(1H)-quinolinone, 7-butylamino-3-hexyloxy-4-methoxy-1-methyl-2(1H)-quinolinone, 7-butylamino-4-butoxy-3-hexyloxy-1-methyl-2(1H)-quinolinone, 7-butylamino-3,4-dihexyloxy-1-methyl-2(1H)-quinolinone, 7-butylamino-3-hexyloxy-4-(3-methyl-2-butenyloxy)-1-methyl-2(1H)-quinolinone, 7-butylamino-4-geranyloxy-3-hexyloxy-1-methyl-2(1H)-quinolinone, 7-butylamino-3-hexyloxy-4-hydroxy-1-methyl-2(1H)-quinolinone, 7-butylamino-4-methoxy-3-(2-methylpentyloxy)-1-methyl-2(1H)-quinolinone, 7-butylamino-4-butoxy-3-(2-methylpentyloxy)-1-methyl-2(1H)-quinolinone, 7-butylamino-4-hexyloxy-3-(2-methylpentyloxy)-1methyl-2(1H)-quinolinone, 7-butylamino-4-(3-methyl-2-butenyloxy)-3-(2-methylpentyloxy)-1-methyl-2(1H)-quinolinone, 7-butylamino-4-geranyloxy-3-(2-methylpentyloxy)-1-methyl-2(1H)-quinolinone, 7-hexylamino-3-methoxy-4-hydroxy-1-methyl-2(1H)-quinolinone, 7-(2-propenylamino)-4-hydroxy-3-octyl-1-methyl-2(2(1H)-quinolinone, 7-prenylamino-4-hydroxy-3-octyloxy-1-methyl-2(1H)-quinolinone, 7-octylamino-4-hydroxy-3-methoxy-1-methyl-2(1H)-quinolinone, 7-octylamino-3-hydroxy-4-methoxy-1-methyl-2(1H)-quinolinone, 7-(octylamino-4-methoxy-3-octyloxy-1-methyl -2(1H)-quinolinone, 7-octylamino-4-butoxy-3-octyloxy-1-methyl-2(1H)-quinolinone, 7-octylamino-4-hexyloxy-3-octyloxy-1-methyl-2(1H)-quinolinone, 7-octylamino-4-(3-methyl-2-butenyloxy)-3-octyloxy-1-methyl-2(1H)-quinolinone, 7-octylamino-4-geranyloxy-3-octyloxy-1-methyl-2(1H)-quinolinone, 7-octylamino-4-hydroxy-3-octyloxy-1-methyl-2(1H)-quinolinone, 7-octylamino-4-methoxy-3-(2-propenyloxy)-1-methyl-2(1H)-quinolinone, 7-octylamino-4-butoxy-3-(2-propenyloxy)-1-methyl-2(1H)-quinolinone, 7-octylamino-4-hexyloxy-3-(2-propenyloxy)-1-methyl-2(1H)-quinolinone, 7-octylamino-4-(3-methyl-2-butenyloxy)-3-(2-propenyloxy)-1-methyl-2(1H)-quinolinone, 7-octylamino-4-(3-methyl-2-butenyloxy)-3-(2-propenyloxy)-1-methyl-2(1H-quinolinone, 7-octylamino-4-geranyloxy-3-(2-propenyloxy)-1-methyl-2(1H)-quinolinone, 7-octylamino-4-hydroxy-3-(2-propenyloxy)-1-methyl-2(1H)-quinolinone, 7-octylamino-3-geranyloxy-4-methoxy-1-methyl-2(1H)-quinolinone, 7-octylamino-4-butyoxy-3-geranyloxy-1-methyl-2(1H)-quinoline, 7-octylamino-3-geranyloxy-4-hexyloxy-1-methyl-2-(1H)-quinolinone, 7-octylamino-3-geranyloxy-4-(3-methyl-2-butenyloxy)- 1-methyl-2(1H)-quinolinone, 7-octylamino-3-geranyloxy-4-hydroxy-1-methyl-2(1H)-quinolinone, 7-octylamino-3-hydroxy-4-methoxy-1-methyl-2(1H)-quinolinone, 7-octylamino-4-butoxy-3-hydroxy-1-methyl-2(1H)-quinolinone, 7-octylamino-4-hexyloxy-3-hydroxy-1-methyl-2(1H)-quinolinone, 7-octylamino-3-hydroxy-4-(3-methyl-2-butenyloxy)-1-methyl-2(1H)-quinolinone, 7-octylamino-4-geranyloxy-3-hydroxy-1-methyl-2(1H)-quinolinone, 7-octylamino-3,4-dihydroxy-1-methyl-2(1H)-quinolinone, 7-octylamino-3-acetoxy-4-methoxy-1-butyl-2(1H)-quinolinone, 7-(2-propenylamino)-4-hydroxy-3-octyloxy-1-butyl-2(1H)-quinolinone, 7-(2-propenylamino)-3-acetoxy-4-butoxy-1-butyl-2(1H)-quinolinone, 7-(2-propenylamino)-3-acetoxy-4-hexyloxy-1-butyl-2(1H)-quinolinone, 7-(2-propenylamino)-3-acetoxy-4-(3-methyl-2-butenyloxy)-1-butyl-2(1H)-quinolinone, 7-(2-propenylamino)-3-acetoxy-4-geranyloxy-1-butyl-2(1H)-quinolinone, 7-(2-propenylamino)-3-acetoxy-4hydroxy-1-butyl-2(1H)-quinolinone, 7-(2-propenylamino)-3-formyloxy-4-methoxy-1-butyl-2(1H)-quinolinone, 7-(2-propenylamino)-4-butoxy-3-formyloxy-1-butyl-2(1H)-quinolinone, 7-(2-propenylamino)-3-formyloxy-4-hexyloxy-1-butyl-2(1H)-quinolinone, 7-(2-propenylamino)-3-formyloxy-4-(3-methyl-2-butenyloxy)-1-butyl-2(1H)-quinolinone, 7-(2-propenylamino)-3-formyl-oxy-4-geranyloxy-1-butyl-2(1H)-quinolinone, 7-(2-propenylamino)-3-formyloxy-4-hydroxy-1-butyl-2(1H)-quinolinone, 7-(2-propenylamino)-

3,4-dimethoxy-1-butyl-2(1H)-quinolinone, 7-(2-propenylamino)-4-butoxy-3-methoxy-1-butyl-2(1H)-quinolinone, 7-(2-propenylamino)-4-hexyloxy-3-methoxy-1-butyl-2(1H)-quinolinone, 7-(2-propenylamino)-3-methoxy-4-(3-methyl-2-butenyloxy)-1-butyl-2(1H)-quinolinone, 7-(2-propenylamino)-4-geranyloxy-3-methoxy-1-butyl-2(1H)-quinolinone, 7-(2-propenylamino)-4-hydroxy-3-methoxy-1-butyl-2(1H)-quinolinone, 7-(2-propenylamino)-3-isopropoxy-4-methoxy-1-butyl-2(1H)-quinolinone, 7-(2-propenylamino)-4-butoxy-3-isopropoxy-1-butyl-2(1H)-quinolinone, 7-(2-propenylamino)-4-hexyloxy-3-isopropoxy-1-butyl-2(1H)-quinolinone, 7-(2-propenylamino)-3-isopropoxy-4-(3-methyl-2-butenyloxy)-1-butyl-2(1H)-quinolinone, 7-(2-propenylamino)-4-geranyloxy-3-isopropoxy-1-butyl-2(1H)-quinolinone, 7-(2-propenylamino)-4-hydroxy-3-isopropoxy-1-butyl-2(1H)-quinolinone, 7-(2-propenylamino)-4-hydroxy-3-octyloxy-1-methyl-2(1H)-quinolinone, 7-(2-propenylamino)-3-butoxy-4-methoxy-1-butyl-2(1H)-quinolinone, 7-(2-propenylamino)-3-butoxy-4-hexyloxy-1-butyl-2(1H)-quinolinone, 7-(2-propenylamino)-3-butoxy-4-(3-methyl-2-butenyloxy)-1-butyl-2(1H)-quinolinone, 7-geranylamino-3-butoxy-4-geranyloxy-1-butyl-2(1H)-quinolinone, 7-geranylamino-3-butoxy-4-hydroxy-1-butyl-2(1H)-quinolinone, 7-geranylamino-3-hexyloxy-4-methoxy-1-butyl-2(1H)-quinolinone, 7-geranylamino-4-butoxy-3-hexyloxy-1-butyl-2(1H)-quinolinone, 7-geranylamino-3,4-dihexyloxy-1-butyl-2(1H)-quinolinone, 7-geranylamino-3-hexyloxy-4-(3-methyl-2-butenyloxy)-1-butyl-2(1H)-quinolinone, 7-geranylamino-4-geranyloxy-3-hexyloxy-1-butyl-2(1H)-quinolinone, 7-geranyl-amino-3-hexyloxy-4-hydroxy-1-butyl-2(1H)-quinolinone, 7-geranylamino-4-methoxy-3-(2-methylpentyloxy)-1-butyl-2(1H)-quinolinone, 7-geranylamino-4-butoxy-3-(2-methylpentyloxy)-1-butyl-2(1H)-quinolinone, 7-geranylamino-4-hexyloxy-3-(2-methylpentyloxy)-1-butyl-2(1H)-quinolinone, 7-geranylamino-4-(3-methyl-2-butenyloxy)-3-(2-methylpentyloxy)-1-butyl-2(1H)-quinolinone, 7-geranylamino-4-geranyloxy-3-(2-methylpentyloxy)-1-butyl-2(1H)-quinolinone, 7-geranylamino-4-hydroxy-3-(2-methylpentyloxy)-1-butyl-2(1H)-quinolinone, 7-geranylamino-4-methoxy-3-octyloxy-1-butyl-2(1H)-quinolinone, 7-geranylamino-4-butoxy-3-octyloxy-1-butyl-2(1H)-quinolinone, 7-geranylamino-4-hexyloxy-3-octyloxy-1-butyl-2(1H)-quinolinone, 7-geranylamino-4-(3-methyl-2-butenyloxy)-3-octyloxy-1-butyl-2(1H)-quinolinone, 7-geranylamino-4-geranyloxy-3-octyloxy-1-butyl-2(1H)-quinolinone, 7-geranylamino-4-hydroxy-3-octyloxy-1-butyl-2(1H)-quinolinone, 7-geranylamino-4-methoxy-3-(2-propenyloxy)-1-butyl-2(1H)-quinolinone, 7-geranylamino-4-butoxy-3-(2-propenyloxy)-1-butyl-2(1H)-quinolinone, 7-geranylamino-4-hexyloxy-3-(2-propenyloxy)-1-butyl-2(1H)-quinolinone, 7-geranylamino-4-(3-methyl-2-butenyloxy)-3-(2-propenyloxy)-1-butyl-2(1H)-quinolinone, 7-acetylamino-4-hydroxy-3-methoxy-2(1H)-quinolinone, 7-acetylamino-3-hexyloxy-4-hydroxy-2(1H)-quinolinone, 7-acetylamino-3-methoxy-4-hydroxy-1-methyl-2(1H)-quinolinone, 7-acetylamino-4-hexyloxy-3-hydroxy-1-methyl-2(1H)-quinolinone, 7-acetylamino-4-octyloxy-3-hydroxy-1-methyl-2(1H)-quinolinone, 7-acetylamino-3-octyloxy-4-hydroxy-1-methyl-2(1H)-quinolinone, 7-acetylamino-4-geranyloxy-3-(2-propenyloxy)-1-butyl-2(1H)-quinolinone, 7-acetylamino-4-hydroxy-3-(2-propenyloxy)-1-butyl-2(1H)-quinolinone, 7-acetylamino-3-geranyloxy-4-methoxy-1-butyl-2(1H)-quinolinone, 7-acetylamino-4-butoxy-3-geranyloxy-1-butyl-2(1H)-quinolinone, 7-acetylamino-3-geranyloxy-4-hexyloxy-1-butyl-2(1H)-quinolinone, 7-acetylamino-3-geranyloxy-4-(3-methyl-2-butenyloxy)-1-butyl-2(1H)-quinolinone, 7-acetylamino-3,4-digeranyloxy-1-butyl-2(1H)-quinolinone, 7-acetylamino-3-geranyloxy-4-hydroxy-1-butyl-2(1H)-quinolinone, 7-acetylamino-3-hydroxy-4-methoxy-1-butyl-2(1H)-quinolinone, 7-acetylamino-4-butoxy-3-hydroxy-1-butyl-2(1H)-quinolinone, 7-acetylamino-4-hexyloxy-3-hydroxy-1-butyl-2(1H)-quinolinone, 7-acetylamino-3-hydroxy-4-(3-methyl-2-butenyloxy)-1-butyl-2(1H)-quinolinone, 7-acetylamino-4-geranyloxy-3-hydroxy-1-butyl-2(1H)-quinolinone, 7-acetylamino-3,4-dihydroxy-1-butyl-2(1H)-quinolinone, 7-acetylamino-3-acetoxy-4-methoxy-1-hexyl-2(1H)-quinolinone, 7-acetylamino-3-acetoxy-4-butoxy-1-hexyl-2(1H)-quinolinone, 7-acetylamino-3-acetoxy-4-hexyloxy-1-hexyl-2(1H)-quinolinone, 7-acetylamino-3-acetoxy-4-(3-methyl-2-butenyloxy)-1-hexyl-2(1H)-quinolinone, 7-acetylamino-3-acetoxy-4-geranyloxy-1-hexyl-2(1H)-quinolinone, 7-acetylamino-3-acetoxy-4-hydroxy-1-hexyl-2(1H)-quinolinone, 7-acetylamino 3-formyloxy-4-methoxy-1-hexyl-2(1H)-quinolinone, 7-acetylamino-4-butoxy-3-formyloxy-1-hexyl-2(1H)-quinolinone, 7-acetylamino-3-formyloxy-4-hexyloxy-1-hexyl-2(1H)-quinolinone, 7-acetylamino-3-formyloxy-4-(3-methyl-2-butenyloxy)-1-hexyl-2(1H)-quinolinone, 7-acetylamino-3-formyloxy-4-geranyloxy-1-hexyl-2(1H)-quinolinone, 7-acetylamino-3-formyloxy-4-hydroxy-1-hexyl-2(1H)-quinolinone, 7-acetylamino-3,4-dimethoxy-1-hexyl-2(1H)-quinolinone, 7-acetylamino-4-butoxy-3-methoxy-1-hexyl-2(1H)-quinolinone, 7-acetylamino-4-hexyloxy-3-methoxy-1-hexyl-2(1H)-quinolinone, 7-acetylamino-3-methoxy-4-(3-methyl-2-butenyloxy)-1-hexyl-2(1H)-quinolinone, 7-acetylamino-4-geranyloxy-3-methoxy-1-hexyl-2(1H)-quinolinone, 7-acetylamino-4-hydroxy-3-methoxy-1-hexyl-2(1H)-quinolinone, 7-acetylamino-3-isopropoxy-4-methoxy-1-hexyl-2(1H)-quinolinone, 7-acetylamino-4-butoxy-3-isopropoxy-1-hexyl-2(1H)-quinolinone, 7-acetylamino-4-hexyloxy-3-isopropoxy-1-hexyl-2(1H)-quinolinone, 7-acetylamino-3-isopropoxy-4-(3-methyl-2-butenyloxy)-1-hexyl-2(1H)-quinolinone, 7-acetylamino-4-geranyloxy-3-isopropoxy-1-hexyl-2(1H)-quinolinone, 7-acetylamino-4-hydroxy-3-isopropoxy-1-hexyl-2(1H)-quinolinone, 7-acetylamino-3-butoxy-4-methoxy-1-hexyl-2(1H)-quinolinone, 7-acetylamino-3,4-dibutoxy-1-hexyl-2(1H)-quinolinone, 7-acetylamino-3-butoxy-4-hexyloxy-1-hexyl-2(1H)-quinolinone, 7-acetylamino-3-butoxy-4-(3-methyl-2-butenyloxy)-1-hexyl-2(1H)-quinolinone, 7-acetylamino-3,4-digeranyloxy-1-butyl-2(1H)-quinolinone, 7-acetylamino-3-geranyloxy-4-hydroxy-1-butyl-2(1H)-quinolinone, 7-benzoylamino-3-hydroxy-4-methoxy-1-butyl-2(1H)-quinolinone, 7-benzoylamino-4-hydroxy-3-octyloxy-1-methyl-2(1H)-quinolinone, 7-benzoylamino-3-hydroxy-4-methoxy-1-butyl-2(1H)-quinolinone, 7-benzoylamino-4-butoxy-3-hydroxy-1-butyl-2(1H)-quinolinone, 7-benzoylamino-4-hexyloxy-3-hydroxy-1-butyl-2(1H)-quinolinone, 7-benzoylamino-3-butoxy-4-geranyloxy-1-methyl-2(1H)-quinolinone, 7-benzoylamino-3-butoxy-4-hydroxy-1-methyl-2(1H)-quinolinone, 7-benzoylamino-3-hexyloxy-4-methoxy-1-methyl-2(1H)-quinolinone, 7-benzoylamino-4-butoxy-3-hexyloxy-1-methyl-2(1H)-quinolinone, 7-benzoylamino-3,4-dihexyloxy-1-ethyl-2(1H)-quinolinone, 7-benzoylamino-3-hexyloxy-4-(3-methyl-2-butenyloxy)-1-ethyl-2(1H)-quinolinone, 7-benzoylamino-4-geranyloxy-3-hexyloxy-1-ethyl-2(1H)-quinolinone, 7-benzoylamino-3-hexyloxy-4-hydroxy-1-hexyl-2(1H)-quinolinone, 7-benzoylamino-4-methoxy-3-(2-methylpentyloxy)-1-hexyl-2(1H)- quinolinone, 7-benzoylamino-4-butoxy-3-(2-methylpentyloxy)-1-hexyl-2(1H)-quinolinone, 7-benzoylamino-4-hexyloxy-3-(2-methylpentyloxy)-1-hexyl-2(1H)-quinolinone, 7-benzoylamino-4-(3-methyl-2-butenyloxy)-3-(2-methylpentyloxy)-1-hexyl-2(1H)-quinolinone, 7-benzoylamino-4-geranyloxy-3-(2-methylpentyloxy)-1-hexyl-2(1H)-quinolinone, 7-benzoylamino-4-hydroxy-3-(2-methylpentyloxy)-1-hexyl-2(1H)-quinolinone, 7-benzoylamino-4-methoxy-3-octyloxy-1-hexyl-2(1H)-quinolinone, 7-benzoylamino-4-butoxy-3-octyloxy-1-hexyl-2(1H)-quinolinone, 7-benzoylamino-4-hexyloxy-3-octyloxy-1-hexyl-2(1H)-quinolinone, 7-benzoylamino-4-(3-methyl-2-butenyloxy)-3-octyloxy-1-hexyl-2(1H)-quinolinone, 7-benzoylamino-4-geranyloxy-3-octyloxy-1-hexyl-2(1H)-quinolinone, 7-benzoylamino-4-hydroxy-3-octyloxy-1-hexyl-2(1H)-quinolinone, 7-benzoylamino-4-methoxy-3-(2-propenyloxy)-1-hexyl-2(1H)-quinolinone, 7-benzoylamino-4-butoxy-3-(2-propenyloxy)-1-hexyl-2(1H)-quinolinone, 7-benzoylamino-4-hexyloxy-3-(2-propenyloxy)-1-hexyl-2(1H)-quinolinone, 7-benzoylamino-4-(3-methyl-2-butenyloxy)-3-(2-propenyloxy)-1-hexyl-2(1H)-quinolinone, 7-benzoylamino-4-geranyloxy-3-(2-propenyloxy)-1-hexyl-2(1H)-quinolinone, 7-benzoylamino-4-hydroxy-3-(2-propenyloxy)-1-hexyl-2(1H)-quinolinone, 7-benzoylamino-3-geranyloxy-4-methoxy-1-hexyl-2(1H)-quinolinone, 7-benzoylamino-4-butoxy-3-geranyloxy-1-hexyl-2(1H)-quinolinone, 7-benzoylamino-3-geranyloxy-4-hexyloxy-1-hexyl-2(1H)-quinolinone, 7-benzoylamino-3-geranyloxy-4-(3-methyl-2-butenyloxy)-1-hexyl-2(1H)-quinolinone, 7-benzoylamino-3,4-digeranyloxy-1-hexyl-2(1H)-quinolinone, 7-benzoylamino-3-geranyloxy-4-hydroxy-1-hexyl-2(1H)-quinolinone, 7-benzoylamino-3-hydroxy-4-methoxy-1-hexyl-2(1H)-quinolinone, 7-benzoylamino-4-butoxy-3-hydroxy-1-hexyl-2(1H)-quinolinone, 7-benzoylamino-4-hexyloxy-3-hydroxy-1-hexyl-2(1H)-quinolinone, 7-benzoylamino-3-hydroxy-4-(3-methyl-2-butenyloxy)-1-hexyl-2(1H)-quinolinone, 7-benzoylamino-4-geranyloxy-3-hydroxy-1-hexyl-2(1H)-quinolinone, 7-benzoylamino-3,4-dihydroxy-1-hexyl-2(1H)-quinolinone, 7-benzoylamino-3-acetoxy-4-methoxy-1-octyl-2(1H)-quinolinone, 7-benzoylamino-3-acetoxy-4-butoxy-1-octyl-2(1H)-quinolinone, 7-benzoylamino-3-acetoxy-4-hexyloxy-1-methyl-2(1H)-quinolinone, 7-cinnamoylamino-3-butoxy-4-geranyloxy-1-methyl-2(1H)-quinolinone, 7-cinnamoylamino-3-butoxy-4-hydroxy-1-methyl-2(1H)-quinolinone, 7-cinnamoylamino-3-hexyloxy-4-methoxy-1-methyl-2(1H)-quinolinone, 7-cinnamoylamino-4-butoxy-3-hexyloxy-1-methyl-2(1H)-quinolinone, 7-cinnamoylamino-3,4-dihexyloxy-1-methyl-2(1H)-quinolinone, 7-cinnamoylamino-3-hexyloxy-4-(3-methyl-2-butenyloxy)-1-methyl-2(1H)-quinolinone, 7-cinnamoylamino-4-geranyloxy-3-hexyloxy-1-methyl-2(1H)-quinolinone, 7-(3,5-dimethoxy-4-acetoxycinnamoylamino)-3-hexyloxy-4-hydroxy-1-methyl-2(1H)-quinolinone, 7-(3,5-dimethoxy-4-acetoxycinnamoylamino)-4-hydroxy-3-octyloxy-1-methyl-2(1H)-quinolinone, 7-(3,5-dimethoxy-4-hydroxycinnamoylamino)-3-hexyloxy-4-hydroxy-1-methyl-2(1H)-quinolinone, 7-(3,5-dimethoxy-4-hydroxycinnamoylamino)-4-hydroxy-3-octyloxy-1-methyl-2(1H)-quinolinone, 7-(4-hydroxy-3-methoxycinnamoylamino)-4-methoxy-3-(2-methylpentyloxy)-1-methyl-2(1H)-quinolinone, 7-(4-hydroxy-3-methoxy-cinnamoylamino)-4-butoxy-3-(2-methylpentyloxy)-1-methyl-2(1H)-quinolinone, 7-(4-hydroxy-3-methoxycinnamoylamino)-4-hexyloxy-3-(2-methylpentyloxy)-1-methyl-2(1H)-quinolinone, 7-(4-hydroxycinnamoylamino)-4-(3-methyl-2-butenyloxy)-3-(2-methylpentyloxy)-1-methyl-2(1H)-quinolinone, 7-cinnamoylamino-4-geranyloxy-3-(2-methylpentyloxy)-1-methyl-2(1H)-quinolinone, 7-(4-hydroxy-3-methoxycinnamoylamino)-4-hydroxy-3-(2-methylpentyloxy)-1-methyl-2(1H)-quinolinone, 7-(4-hydroxy-3-methoxycinnamoylamino)-4-methoxy-3-octyloxy-1-methyl-2(1H)-quinolinone, 7-cinnamoylamino-4-butoxy-3-octyloxy-1-methyl-2(1H)-quinolinone, 7-cinnamoylamino-4-hexyloxy-3-octyloxy-1-methyl-2(1H)-quinolinone, 7-cinnamoylamino-4-(3-methyl-2-butenyloxy)-3-octyloxy-1-methyl-2(1H)-quinolinone, 7-cinnamoylamino-4-geranyloxy-3-octyloxy-1-methyl-2(1H)-quinolinone, 7-(4-hydroxy-3-methoxycinnamoylamino)-4-hydroxy-3-octyloxy-1-methyl-2(1H)-quinolinone, 7-cinnamoylamino-4-methoxy-3-(2-propenyloxy)-1-methyl-2(1H)-quinolinone, 7-cinnamoylamino-4-butoxy-3-(2-propenyloxy)-1-methyl-2(1H)-quinolinone, 7-cinnamoylamino-4-hexyloxy-3-(2-propenyloxy)-1-methyl-2(1H)-quinolinone, 7-cinnamoylamino-4-(3-methyl-2-butenyloxy)-3-(2-propenyloxy)-1-methyl-2(1H)-quinolinone, 7-cinnamoylamino-3-geranyloxy-4-methoxy-1-methyl-2(1H)-quinolinone, 7-cinnamoylamino-4-butoxy-3-geranyloxy-1-methyl-2(1H)-quinolinone, 7-cinnamoylamino-3-geranyloxy-4-methoxy-3-(2-methylpentyloxy)-1-methyl-2(1H)-quinolinone, 7-(4-hydroxy-3-methoxy-cinnamoylamino)-4-butoxy-3-(2-methylpentyloxy)-1-methyl-2(1H)-quinolinone, 7-(4-hydroxy-3-methoxycinnamoylamino)-4-hexyloxy-3-(2-methylpentyloxy)-1-methyl-2(1H)-quinolinone, 7-(4-hydroxycinnamoylamino)-4-(3-methyl-2-butenyloxy)-3-(2-methylpentyloxy)-1-methyl-2(1H)-quinolinone, 7-cinnamoylamino-4-geranyloxy-3-(2-methylpentyloxy)-1-methyl-2(1H)-quinolinone, 7-(4-hydroxy-3-methoxycinnamoylamino)-4-hydroxy-3-(2-methylpentyloxy)-1-methyl-2(1H)-quinolinone, 7-(4-hydroxy-3-methoxycinnamoylamino)-4-methoxy-3-octyloxy-1-hexyl-2(1H)-quinolinone, 7-cinnamoylamino-4-butoxy-3-octyloxy-1-hexyl-2(1H)-quinolinone, 7-cinnamoylamino-4-hexyloxy-3-octyloxy-1-hexyl-2(1H)-quinolinone, 7-cinnamoylamino-4-(3-methyl-2-butenyloxy)-3-octyloxy-1-hexyl-2(1H)-quinolinone, 7-cinnamoylamino-4-geranyloxy-3-octyloxy-1-hexyl-2(1H)-quinolinone, 7-(4-hydroxy3-methoxycinnamoylamino)-4-hydroxy-3-octyloxy-1-hexyl-2(1H)-quinolinone, 7-cinnamoylamino-4-methoxy-3-(2-propenyloxy)-1-hexyl-2(1H)-quinolinone, 7-cinnamoylamino-4-butoxy-3-(2-propenyloxy)-1-hexyl-2(1H)-quinolinone, 7-cinnamoylamino-4-hexyloxy-3-(2-propenyloxy)-1-hexyl-2(1H)-quinolinone, 7-cinnamoylamino-4-(3-methyl-2-butenyloxy)-3-(2-propenyloxy)-1-hexyl-2(1H)-quinolinone, 7-cinnamoylamino-4-geranyloxy-3-(2-propenyloxy)-1-hexyl-2(1H)-quinolinone, 7-cinnamoylamino-4-hydroxy-3-(2-propenyloxy)-1-hexyl-2(1H)-quinolinone, 7-cinnamoylamino-3-geranyloxy-4-methoxy-1-hexyl-2(1H)-quinolinone, 7-cinnamoylamino-4-butoxy-3-geranyloxy-1-hexyl-2(1H)-quinolinone, 7-cinnamoylamino-3-geranyloxy-4-hexyloxy-1-hexyl-2(1H)-quinolinone, 7-cinnamoylamino-3-geranyloxy-4-(3-methyl-2-butenyloxy)-1-hexyl-2(1H)-quinolinone, 7-cinnamoylamino-3,4-digeranyloxy-1-hexyl-2(1H)-quinolinone, 7-cinnamoylamino-3-geranyloxy-4-hydroxy-1-hexyl-2(1H)-quinolinone, 7-cinnamoylamino-3-hydroxy-4-methoxy-1-hexyl-2(1H)-quinolinone, 7-cinnamoylamino- 4-butoxy-3-hydroxy-1-hexyl-2(1H)-quinolinone, 7-(3,5-dimethoxy-4-hydroxycinnamoylamino)-4-hexyloxy-3-hydroxy-1-hexyl-2(1H)-quinolinone, 7-(3,5-dimethoxy-4-hydroxycinnamoylamino)-3-hydroxy-4-(3-methyl-2-butenyloxy)-1-hexyl-2(1H)-quinolinone, 7-cinnamoylamino-4-geranyloxy-3-hydroxy-1-hexyl-2(1H)-quinolinone, 7-cinnamoylamino-3,4-dihydroxy-1-hexyl-2(1H)-quinolinone, 7-cinnamoylamino-3-acetoxy-4-methoxy-1-octyl-2(1H)-quinolinone, 7-(3,5-dimethoxy-4-hydroxycinnamoylamino)-3-acetoxy-4-butoxy-1-octyl-2(1H)-quinolinone, 7-cinnamoylamino-3-acetoxy-4-hexyloxy-1-octyl-2(1H)-quinolinone, 7-benzylamino-3-acetoxy-4-(3-methyl-2-butenyloxy)-1-methyl-2(1H)-quinolinone, 7-benzylamino-3-acetoxy-4-geranyloxy-1-methyl-2(1H)-quinolinone, 7-benzylamino-3-acetoxy-4-hydroxy-1-methyl-2(1H)-quinolinone, 7-benzylamino-3-formyloxy-4-methoxy-1-methyl-2(1H)-quinolinone, 7-benzylamino-4-butoxy-3-formyloxy-1-methyl-2(1H)-quinolinone, 7-benzylamino-3-formyloxy-4-hexyloxy-1-methyl-2(1H)-quinolinone, 7-benzylamino-3-formyloxy-4-(3-methyl-2-butenyloxy)-1-methyl-2(1H)-quinolinone, 7-benzylamino-3-formyloxy-4-geranyloxy-1-methyl-2(1H)-quinolinone, 7-benzylamino-3-formyloxy-4-hydroxy-1-methyl-2(1H)-quinolinone, 7-benzylamino-3,4-dimethoxy-1-methyl-2(1H)-quinolinone, 7-benzylamino-4-butoxy-3-methoxy-1-methyl-2(1H)-quinolinone, 7-benzylamino-4-hexyloxy-3-methoxy-1-methyl-2(1H)-quinolinone, 7-benzylamino-3-methoxy-4-(3-methyl-2-butenyloxy)-1-methyl-2(1H)-quinolinone, 7-benzylamino-4-geranyloxy-3-methoxy-1-methyl-2(1H)-quinolinone, 7-benzylamino-4-hydroxy-3-methoxy-1-methyl-2(1H)-quinolinone, 7-benzylamino-3-isopropoxy-4-methoxy-1-methyl-2(1H)-quinolinone, 7-benzylamino-4-butoxy-3-isopropoxy-1-methyl-2(1H)-quinolinone, 7-benzylamino-4-hexyloxy-3-isopropoxy-1-methyl-2(1H)-quinolinone 7-benzylamino-3-isopropoxy-4-(3-methyl-2-butenyloxy)-1-methyl-2(1H)-quinolinone, 7-benzylamino-4-geranyloxy-3-isopropoxy-1-methyl-2(1H)-quinolinone, 7-benzylamino-4-hydroxy-3-isopropoxy-1-methyl-2(1H)-quinolinone, 7-benzylamino-3-butoxy-4-methoxy-1-methyl-2(1H)-quinolinone, 7-benzylamino-3,4-dibutoxy-1-methyl-2(1H)-quinolinone, 7-benzylamino-3-butoxy-4-hexyloxy-1-methyl-2(1H)-quinolinone, 7-benzylamino-3-butoxy-4-(3-methyl-2-butenyloxy)-1-methyl-2(1H)-quinolinone, 7-benzylamino-3-butoxy-4-geranyloxy-1-methyl-2(1H)-quinolinone, 7-benzylamino-3-butoxy-4-hydroxy-1-methyl-2(1H)-quinolinone, 7-benzylamino-3-hexyloxy-4-methoxy-1-octyl-2(1H)-quinolinone, 7-benzylamino-4-butoxy-3-hexyloxy-1-octyl-2(1H)-quinolinone, 7-benzylamino-3,4-dihexyloxy-1-octyl-2(1H)-quinolinone, 7-benzylamino-3-hexyloxy-4-(3-methyl-2-butenyloxy)-1-octyl-2(1H)-quinolinone, 7-benzylamino-4-geranyloxy-3-hexyloxy-1-octyl-2(1H)-quinolinone, 7-benzylamino-3-hexyloxy-4-hydroxy-1-octyl-2(1H)-quinolinone, 7-benzylamino-4-methoxy-3-(2-methylpentyloxy)-1-octyl-2(1H)-quinolinone, 7-benzylamino-4-butoxy-3-(2-methylpentyloxy)-1-octyl-2(1H)-quinolinone, 7-benzylamino-4-hexyloxy-3-(2-methylpentyloxy)-1-octyl-2(1H)-quinolinone, 7-benzylamino-4-(3-methyl-2butenyloxy)-3-2-methylpentyloxy)-1-octyl-2(1H)-quinolinone, 7-benzylamino-4-geranyloxy-3-(2-methylpentyloxy)-1-octyl-2(1H)-quinolinone, 7-benzylamino-4-hydroxy-3-(2-methylpentyloxy)-1-octyl-2(1H)-quinolinone, 7-benzylamino-4-methoxy-3-octyloxy-1-octyl-2(1H)-quinolinone, 7-benzylamino-4-butoxy-3-octyloxy-1-octyl-2(1H)-quinolinone, 7-benzylamino-4-hexyloxy-3-octyloxy-1-octyl-2(1H)-quinolinone, 7-benzylamino-4-(3-methyl-2-butenyloxy)-3-octyloxy-1-octyl-2(1H)-quinolinone, 7-benzylamino-4-geranyloxy-3-octyloxy-1-octyl-2(1H)-quinolinone, 7-benzylamino-4-octyloxy-1-octyl-2(1H)-quinolinone, 7-benzylamino-4-hydroxy-3-octyloxy-1-methyl-2(1H)-quinolinone, 7-benzylamino-3-hexyloxy-4-hydroxy-1-ethyl-2(1H)-quinolinone, 7-benzylamino-3-hexyloxy-4-hydroxy-1-propyl-2(1H)-quinolinone, 7-benzylamino-4-methoxy-3-(2-propenyloxy)-1-octyl-2(1H)-quinolinone, 7-benzylamino-4-butoxy-3-(2-propenyloxy)-1-octyl-2(1H)-quinolinone, 7-benzylamino-4-hexyloxy-3-(2-propenyloxy)-1-octyl-2(1H)-quinolinone, 7-benzylamino-4-(3-methyl-2-butenyloxy)-3-(2-propenyloxy)-1-octyl-2(1H)-quinolinone, 7-benzylamino-4-geranyloxy-3-(2-propenyloxy)-1-octyl-2(1H)-quinolinone, 7-benzylamino-4-hydroxy-3-(2-propenyloxy)-1-octyl-2(1)-quinolinone, 7-benzylamino-3-geranyloxy-4-methoxy-1-octyl-2(1H)-quinolinone, 7-benzylamino-4-butoxy-3-geranyloxy-1-octyl-2(1H)-quinolinone, 7-benzylamino-3-geranyloxy-4-hexyloxy-1-octyl-2(1H)-quinolinone, 7-benzylamino-3-geranyloxy-4-(3-methyl-2-butenyloxy)-1-octyl-2(1H)-quinolinone, 7-benzylamino-3,4-digeranyloxy-1-octyl-2(1H)-quinolinone, 7-benzylamino-3-geranyloxy-4-hydroxy-1-octyl-2(1H)-quinolinone, 7-benzylamino-3-hydroxy-4-methoxy-1-octyl-2(1H)-quinolinone, 7-benzylamino-4-butoxy-3-hydroxy-1-octyl-2(1H)-quinolinone, 7-benzylamino-4-hexyloxy-3-hydroxy-1-octyl-2(1H)-quinolinone, 7-benzylamino-3-hydroxy-4-(3-methyl-2-butenyloxy)-1octyl-2-(1H)-quinolinone, 7-benzylamino-4-geranyloxy-3-hydroxy-1-octyl-2(1H)-quinolinone, 7-benzylamino-3,4-dihydroxy-1-octyl-2(1H)-quinolinone.

Physiologically acceptable salts of these compounds are also included in the illustrative examples.

As to compounds having hydroxy groups at 3 position and/or 4 position described above, the term "physiologically acceptable salts" as used herein means nontoxic alkali addition salts of, for example, the compounds cited above, which include sodium salts, As to compounds having hydroxy groups at 3 position and/or 4 position described the like. These physiologically acceptable salts can be produced by known methods and are also included in the present invention. As to compounds having no hydroxy groups at 3 position and/or 4 position, the term "physiologically acceptable salts" means nontoxic addition salts of amino groups and mineral acid salts (for example hydrochloric acid and sulfuric acid), also included in the present invention. As to compounds having no hydroxy groups at 3 position and/or 4 position, the term "physiologically acceptable salts" means nontoxic addition the like.

These physiologically acceptable salts can be produced by known methods and are also included in the present invention.

7-nitroquinolinone derivatives represented by the formula (II) of the present invention are important intermediates for synthesis of 7-aminoquinolinone derivatives of the present invention, the following compounds are illustrative examples.

7-nitro-3-acetoxy-4-methoxy-2(1H)-quinolinone, 7-nitro-3-acetoxy-4-butoxy-2(1)-quinolinone, 7-nitro-3-acetoxy-4-hexyloxy-2(1H)-quinolinone, 7-nitro-3-acetoxy-4-(3-methyl-2-butenyloxy)-2(1H)-quinolinone, 7-nitro-3-acetoxy-4-geranyloxy-2(1H)-quinolinone, 7-nitro-3-acetoxy-4-hydroxy-2(1H)-quinolinone, 7-nitro-3-formyloxy-4-methoxy-2(1H)-quinolinone, 7-nitro-4-butoxy-3-formyloxy-2(1H)-quinolinone, 7-nitro-3-formyloxy-4-hexyloxy-2(1H)-quinolinone, 7-nitro-3- formyloxy-4-(3-methyl-2-butenyloxy)-2(1H)-quinolinone, 7-nitro-3-formyloxy-4-geranyloxy-2(1H)-quinolinone, 7-nitro-3-formyloxy-4-hydroxy-2(1H)-quinolinone, 7-nitro-3,4-dimethoxy-2(1H)-quinolinone, 7-nitro-4-butoxy-3-methoxy-2(1H)-quinolinone, 7-nitro-4-hexyloxy-3-methoxy-2(1H)-quinolinone, 7-nitro-3-methoxy-4-(3-methyl-2-butenyloxy)-2(1H)-quinolinone, 7-nitro-4-geranyloxy-3-methoxy-2(1H)-quinolinone, 7-nitro-4-hydroxy-3-methoxy-2(1H)-quinolinone, 7-nitro-3-isopropoxy-4-methoxy-2(1H)-quinolinone, 7-nitro-4-butoxy-3-isopropoxy-2(1H)-quinolinone, 7-nitro-4-hexyloxy-3-isopropoxy-2(1H)-quinolinone, 7-nitro-3-isopropoxy-4-(3-methyl-2-butenyloxy)-2(1H)-quinolinone, 7-nitro-4-geranyloxy-3-isopropoxy-2(1H)-quinolinone, 7-nitro-4-hydroxy-3-isopropoxy-2(1H)-quinolinone, 7-nitro-3-butoxy-4-methoxy-2(1H)-quinolinone, 7-nitro-3,4-dibutoxy-2(1H)-quinolinone, 7-nitro-3-butoxy-4-hexyloxy-2(1H)-quinolinone, 7-nitro-3-butoxy-4-(3-methyl-2-butenyloxy)-2(1H)-quinolinone, 7-nitro-3-butoxy-4-geranyloxy-2(1H)-quinolinone, 7-nitro-3-butoxy-4-hydroxy-2(1H)-quinolinone, 7-nitro-3-hexyloxy-4-methoxy-2(1H)-quinolinone, 7-nitro-4-butoxy-3-hexyloxy-2(1H)-quinolinone, 7-nitro-3,4-dihexyloxy-2(1H)-quinolinone, 7-nitro-3-hexyloxy-4-(3-methyl-2-butenyloxy)-2(1H)-quinolinone, 7-nitro-4-geranyloxy-3-hexyloxy-2(1H)-quinolinone, 7-nitro-3-hexyloxy-4-hydroxy-2(1H)-quinolinone, 7-nitro-4-methoxy-3-(2-methylpentyloxy)-2(1H)-quinolinone, 7-nitro-4-butoxy-3-(2-methylpentyloxy)-2(1H)-quinolinone, 7-nitro-4-hexyloxy-3-(2-methylpentyloxy)-2(1H)-quinolinone, 7-nitro-4-(3-methyl-2-butenyloxy)-3-(2-methylpentyloxy)-2(1H)-quinolinone, 7-nitro-4-geranyloxy-3-(2-methylpentyloxy)-2(1H)-quinolinone, 7-nitro-4-hydroxy-3-(2-methylpentyloxy)-2(1H)-quinolinone, 7-nitro-4-methoxy-3-octyloxy-2(1H)-quinolinone, 7-nitro-4-butoxy-3-octyloxy-2(1H)-quinolinone, 7-nitro- 4-hexyloxy-3-octyloxy-2(1H)-quinolinone, 7-nitro-4-(3-methyl-2-butenyloxy)-3-octyloxy-2(1H)-quinolinone, 7-nitro-4-geranyloxy-3-octyloxy-2(1H)-quinolinone, 7-nitro-4-hydroxy-3-octyloxy-2(1H)-quinolinone, 7-nitro-4-methoxy-3-(2-propenyloxy)-2(1H)-quinolinone, 7-nitro-4-butoxy-3-(2-propenyloxy)-2(1H)-quinolinone, 7-nitro-4-hexyloxy-3-(2-propenyloxy)-2(1H)-quinolinone, 7-nitro-4-(3-methyl-2-butenyloxy)-3-(2-propenyloxy)-2(1H)-quinolinone, 7-nitro-4-geranyloxy-3-(2-propenyloxy)-2(1H)-quinolinone, 7-nitro-4-hydroxy-3-(2-propenyloxy)-2(1H)-quinolinone, 7-nitro-3-geranyloxy-4-methoxy-2(1H)-quinolinone, 7-nitro-4-butoxy-3-geranyloxy-2(1H)-quinolinone, 7-nitro-3-geranyloxy-4-hexyloxy-2(1H)-quinolinone, 7-nitro-3-geranyloxy-4-(3-methyl-2-butenyloxy)-2(1H)-quinolinone, 7-nitro-3,4-digeranyloxy-2(1H)-quinolinone, 7-nitro-3-geranyloxy-4-hydroxy-2(1H)-quinolinone, 7-nitro-3,4-dihydroxy-2(1H)-quinolinone, 7-nitro-3-hydroxy-4-methoxy-2(1H)-quinolinone, 7-nitro-4-butoxy-3-hydroxy-2(1H)-quinolinone, 7-nitro-4-hexyloxy-3-hydroxy-2(1H)-quinolinone, 7-nitro-3-hydroxy-4-(3-methyl-2-butenyloxy)-2(1H)-quinolinone, 7-nitro-4-geranyloxy-3-hydroxy-2(1H)-quinolinone, 7-nitro-3-acetoxy-4-methoxy-1-methyl-2(1H)-quinolinone, 7-nitro-3-acetoxy-4-ethoxy-1-methyl-2(1H)-quinolinone, 7-nitro-3-acetoxy-4-butoxy-1-methyl-2(1H)-quinolinone, 7-nitro-3-acetoxy-4-hexyloxy-1-methyl-2(1H)-quinolinone, 7-nitro-3-acetoxy-4-(3-methyl-2-butenyl-oxy)-1-methyl-2(1H)-quinolinone, 7-nitro-3-acetoxy-4-geranyloxy-1-methyl-2(1H)-quinolinone, 7-nitro-3-acetoxy-4-hydroxy-1-methyl-2(1H)-quinolinone, 7-nitro-3-formyloxy-4-methoxy-1-methyl-2(1H)-quinolinone, 7-nitro-4-butoxy-3-formyloxy-1-methyl-2(1H)-quinolinone, 7-nitro-3-formyloxy-4-hexyloxy-1-methyl-2(1H)-quinolinone, 7-nitro-3-formyloxy-4-(3-methyl-2-butenyloxy)-1-methyl-2(1H)-quinolinone, 7-nitro-3-formyloxy-4-geranyloxy-1-methyl-2(1H)-quinolinone, 7-nitro-3-formyloxy-4-hydroxy-1-methyl-2(1H)-quinolinone, 7-nitro-3,4-dimethoxy-1-methyl-2(1H)-quinolinone, 7-nitro-4-butoxy-3-methoxy-1-methyl-2(1H)-quinolinone, 7-nitro-4-hexyloxy-3-hydroxy-1-methyl-2(1H)-quinolinone, 7-nitro-4-hexyloxy-3-methoxy-1-methyl-2(1H)-quinolinone, 7-nitro-3-methoxy-4-(3-methyl-2-butenyloxy)-1-methyl-2(1H)-quinolinone, 7-nitro-4-geranyloxy-3-methoxy-1-methyl-2(1H)-quinolinone, 7-nitro-4-hydroxy-3-methoxy-1-methyl-2(1H)-quinolinone, 7-nitro-3-isopropoxy-4-methoxy-1-methyl-2(1H)-quinolinone, 7-nitro-4-butoxy-3-isopropoxy-1-methyl-2(1H)-quinolinone, 7-nitro-4-hexyloxy-3-isopropoxy-1-methyl-2(1H)-quinolinone, 7-nitro-3-isopropoxy-4-(3-methyl-2-butenyloxy)-1-methyl-2(1H)-quinolinone, 7-nitro-4-geranyloxy-3-isopropoxy-1-methyl-2(1H)-quinolinone, 7-nitro-4-hydroxy-3-isopropoxy-1-methyl-2(1H)-quinolinone, 7-nitro- 3-butoxy-4-methoxy-1-methyl-2(1H)-quinolinone, 7-nitro-3,4-dibutoxy-1-methyl-2(1H)-quinolinone, 7-nitro-3-butoxy-4-hexyloxy-1-methyl-2(1)-quinolinone, 7-nitro-3-butoxy-4-(3-methyl-2-butenyloxy)-1-methyl-2(1H)-quinolinone, 7-nitro-3-butoxy-4-geranyloxy-1-methyl-2(1H)-quinolinone, 7-nitro-3-butoxy-4-hydroxy-1-methyl-2(1H)-quinolinone, 7-nitro-3-hexyloxy-4-methoxy-1-methyl-2(1H)-quinolinone, 7-nitro-4-butoxy-3-hexyloxy-1-methyl-2(1H)-quinolinone, 7-nitro-3,4-dihexyloxy-1-methyl-2(1H)-quinolinone, 7-nitro-3-hexyloxy-4-(3-methyl-2-butenyloxy)-1-methyl-2(1H)-quinolinone, 7-nitro-4-geranyloxy-3-hexyloxy-1-methyl-2(1H)-quinolinone, 7-nitro-3-hexyloxy-4-hydroxy-1-methyl-2(1H)-quinolinone, 7-nitro-4-methoxy-3-(2-methylpentyloxy)-1-methyl-2(1H)-quinolinone, 7-nitro-4-butoxy-3-(2-methyl-pentyloxy)-1-methyl-2(11H)-quinolinone, 7-nitro-4-hexyloxy-3-(2-methylpentyloxy)-1-methyl-2(1H)-quinolinone, 7-nitro-4-(3-methyl-2-butenyloxy)-3-(2-methyl-pentyloxy)-1-methyl-2(1H)-quinolinone, 7-nitro-4-geranyloxy-3-(2-methyl-pentyloxy)-1-methyl-2(1H)-quinolinone, 7-nitro-4-hydroxy-3-(2-methylpentyloxy)-1-methyl-2(1H)-quinolinone, 7-nitro-4-methoxy-3-octyloxy-1-methyl-2(1H)-quinolinone, 7-nitro-4- butoxy-3-octyloxy-1-methyl-2(1H)-quinolinone, 7-nitro-4-hexyloxy-3-octyloxy-1-methyl-2(1H)-quinolinone, 7-nitro-4-(3-methyl-2-butenyloxy)-3-octyloxy-1-methyl-2(1H)-quinolinone, 7-nitro-4-geranyloxy-3-octyloxy-1-methyl-2(1H)-quinolinone, 7-nitro-4-hydroxy-3-octyloxy-1-methyl-2(1H)-quinolinone, 7-nitro-4-methoxy-3-(2-propenyloxy)-1-methyl-2(1H)-quinolinone, 7-nitro-4-butoxy-3-(2-propenyloxy)-1-methyl-2(1H)-quinolinone, 7-nitro-4-hexyloxy-3-(2-propenyloxy)-1-methyl-2(1H)-quinolinone, 7-nitro-4-(3-methyl-2-butenyloxy)-3-(2-propenyloxy)-1-methyl-2(1H)-quinolinone, 7-nitro-4-geranyloxy-3-(2-propenyloxy)-1-methyl-2(1H)-quinolinone, 7-nitro-4-hydroxy-3-(2-propenyloxy)-1-methyl-2(1H)-quinolinone, 7-nitro-3-geranyloxy-4-methoxy-1-methyl-2(1H)-quinolinone, 7-nitro-4-butoxy-3-geranyloxy-1-methyl-2(1H)-quinolinone, 7-nitro-3-geranyloxy-4-hexyloxy-1-methyl-2(1H)-quinolinone, 7-nitro-3-geranyloxy-4-(3-methyl-2-butenyloxy)-1-methyl-2(1H)-quinolinone, 7-nitro-3-geranyloxy-4-hydroxy-1-methyl-2(1H)-quinolinone, 7-nitro-3-hydroxy-4-methoxy--methyl-2(1H)-quinolinone, 7-nitro-4-butoxy-3-hydroxy-1-methyl-2(1H)-quinolinone, 7-nitro-4-hexyloxy-3-hydroxy-1methyl-2(1H)-quinolinone, 7-nitro 3-hydroxy-4-(3-methyl-2-butenyloxy)-1-methyl-2(1H)-quinolinone, 7-nitro-4-geranyloxy-3-hydroxy-1-methyl-2(1H)-quinolinone, 7-nitro-3,4-dihydroxy-1-methyl-2(1H)-quinolinone, 7-nitro-3-acetoxy-4-methoxy-1-ethyl-2(1H)-quinolinone, 7-nitro-3-acetoxy-4-ethoxy-1ethyl-1-2(1H)-quinolinone, 7-nitro-3-acetoxy-4-geranyloxy-1-ethyl-2(1H)-quinolinone,7-nitro-3-acetoxy- 4-hexyloxy-1-ethyl-2(1H)-quinolinone, 7-nitro-3-acetoxy-4-(3-methyl-2-butenyloxy)-1-ethyl-2(1H)-quinolinone, 7-nitro-3-acetoxy-4-geranyloxy-1-ethyl-2(1H)-quinolinone, 7-nitro-3-acetoxy-4-hydroxy-1-ethyl-2(1H)-quinolinone, 7-nitro-3-formyloxy-4-methoxy-1-ethyl-2(1H)-quinolinone, 7-nitro-4-butoxy-3-formyloxy-1-ethyl-2(1H)-quinolinone, 7-nitro-3-formyloxy-4-hexyloxy-1-ethyl-2(1H)-quinolinone, 7-nitro-3-formyloxy-4-(3-methyl-2-butenyloxy)-1-ethyl-2(1H)-quinolinone, 7-nitro-3-formyloxy-4-geranyloxy-1-ethyl-2(1H)-quinolinone, 7-nitro-3-formyloxy-4-hydroxy-1-ethyl-2(1H)-quinolinone, 7-nitro-3,4-dimethoxy-1-ethyl-2(1H)-quinolinone, 7-nitro-4-butoxy-3-methoxy-1-ethyl-2(1H)-quinolinone, 7-nitro-4-hexyloxy-3-methoxy-1-ethyl-2(1H)-quinolinone, 7-nitro-3-methoxy-4-(3-methyl-2-butenyloxy)-1-ethyl-2(1H)-quinolinone, 7-nitro-4-geranyloxy-3-methoxy-1-2(1H)-quinolinone, 7-nitro-4-hydroxy-3-methoxy-1-ethyl-2(1H)-quinolinone, 7-nitro-3-isopropoxy-4-methoxy-1-ethyl-2(1H)-quinolinone, 7-nitro-4-butoxy-3-isopropoxy-1-ethyl-2(1H)-quinolinone, 7-nitro-4-hexyloxy-3-isopropoxy-1-ethyl-2(1H)-quinolinone, 7-nitro-3-isopropoxy-4-(3-methyl-2-butenyloxy)-1-ethyl-2(1H)-quinolinone, 7-nitro-4-geranyloxy-3-isopropoxy-1-ethyl-2(1H)-quinolinone, 7-nitro-4-hydroxy-3-isopropoxy-1-ethyl-2(1H)-quinolinone, 7-nitro-3-butoxy-4-methoxy-1-ethyl-2(1-)-quinolinone, 7-nitro-3,4-dibutoxy-1-ethyl-2(1H)-quinolinone, 7-nitro-3-butoxy-4-hexyloxy-1-ethyl-2(1H)-quinolinone, 7-nitro-3-butoxy-4-(3-methyl-2-butenyloxy)-1-ethyl-2(1H)-quinolinone, 7-nitro-3-butoxy-4-geranyloxy-1-ethyl-2(1H)-quinolinone, 7-nitro-3-butoxy-4-hydroxy-1-ethyl-2(1H)-quinolinone, 7-nitro-3-hexyloxy-4-methoxy-1-ethyl-2(1H)-quinolinone, 7-nitro-4-butoxy-3-hexyloxy-1-ethyl-2(1H)-quinolinone, 7-nitro-4-methoxy-3-(2-methyl-pentyloxy)-1-ethyl-2(1H)-quinolinone, 7-nitro-3-hexyloxy-4-(3-methyl-2-butenyloxy)-1-ethyl-2(1H)-quinolinone, 7-nitro-4-geranyloxy-3-hexyloxy-1-ethyl-2(1H)-quinolinone, 7-nitro-3-hexyloxy-4-hydroxy-1-ethyl-2(1H)-quinolinone, 7-nitro-4-methoxy-3-(2-methyl-pentyloxy)-1-ethyl-2(1H)-quinolinone, 7-nitro-4-butoxy-3-(2-methylpentyloxy)-1-ethyl-2(1H)-quinolinone, 7-nitro-4-hexyloxy-3(2-methylpentyloxy)-1-ethyl-2(1H)-quinolinone, 7-nitro-4-(3-methyl-2-butenyloxy)-3-(2-methylpentyloxy)-1-ethyl-2(1H)-quinolinone, 7-nitro-4-geranyloxy-3-(2-methylpentyloxy)-1-ethyl-2(1H)-quinolinone, 7-nitro-4-hydroxy-3-(2-methylpentyloxy)-1-ethyl-2(1H)-quinolinone, 7-nitro-4-methoxy-3-octyloxy-1-ethyl-2(1H)-quinolinone, 7-nitro-4-butoxy-3-octyl-1-ethyl-2(1H)-quinolinone, 7-nitro-4-hexyloxy-3-octyloxy-1-ethyl-2(1H)-quinolinone, 7-nitro-4-(3-methyl-2-butenyloxy)-3-octyloxy-1-ethyl-2(1H)-quinolinone, 7-nitro-4-geranyloxy-3-octyloxy-1-ethyl-2(1H)-quinolinone, 7-nitro-4-hexyloxy-3-octyloxy-1-ethyl-2(1H)-quinolinone, 7-nitro-4-methoxy-3-(2-propenyloxy)-1-ethyl-2(1H)-quinolinone, 7-nitro-4-butoxy-3-(2-propenyloxy)-1-ethyl-2(1H)-quinolinone, 7-nitro-4-hexyloxy-3-(2-propenyloxy)-1-ethyl-2(1H)-quinolinone, 7-nitro-4-(3-methyl-2-butenyloxy)-3-(2propenyloxy)-1ethyl-2(1H)-quinolinone, 7-nitro-4-geranyloxy-3-(2-propenyloxy)-1-ethyl-2(1H)-quinolinone, 7-nitro-4-hydroxy-3-(2-propenyloxy)-1-ethyl-2(1H)-quinolinone, 7-nitro-3-geranyloxy-4-methoxy-1-ethyl-2(1H)-quinolinone, 7-nitro-4-butoxy-3-geranyloxy-1-ethyl-2(1H)-quinolinone, 7-nitro-3-geranyloxy-4-hexyloxy-1-ethyl-2(1H)-quinolinone, 7-nitro-3-geranyloxy-4-(3-methyl-2-butenyloxy)-1-ethyl-2(1H)-quinolinone, 7-nitro-3,4-digeranyloxy-1ethyl-2(1H)-quinolinone, 7-nitro-3-geranyloxy-4-hydroxy-1ethyl-2(1H)-quinolinone, 7-nitro-3-hydroxy-4-methoxy-1-ethyl-2(1H)-quinolinone, 7-nitro-4-butoxy-3-hydroxy-1-ethyl-2(1H)-quinolinone, 7-nitro-4-hexyloxy-3-hydroxy-1-ethyl-2(1H)-quinolinone, 7-nitro-3-hydroxy-4-(3-methyl-2-butenyloxy)-1-ethyl-2(1H)-quinolinone, 7-nitro-4-geranyloxy-3-hydroxy-1-ethyl-2(1H)-quinolinone, 7-nitro-3,4-dihydroxy-1-ethyl-2(1H)-quinolinone, 7-nitro-3-acetoxy-4-methoxy-1-butyl-2(1H)-quinolinone, 7-nitro-3-acetoxy-4-ethoxy-1-butyl-2(1H)-quinolinone, 7-nitro-3-acetoxy-4-butoxy-1-butyl-2(1H)-quinolinone, 7-nitro-3-acetoxy4-hexyloxy-1-butyl-2(1H)-quinolinone, 7-nitro-3-acetoxy-4-(3-methyl-2-butenyloxy)-1-butyl-2(1H)-quinolinone, 7-nitro-3-acetoxy-4-geranyloxy-1-butyl-2(1H)-quinolinone, 7-nitro-3-acetoxy-4-hydroxy-1-butyl-2(1H)-quinolinone, 7-nitro-3formyloxy-4-methoxy-1butyl-2(1H)-quinolinone, 7-nitro-4-butoxy-3-formyloxy-1-butyl-2(1H)-quinolinone, 7-nitro-3-formyloxy4-hexyloxy-1-butyl-2(1H)-quinolinone, 7-nitro-3-formyloxy-4-(3-methyl-2-butenyloxy)-1-butyl-2(1H)-quinolinone, 7-nitro-3-formyloxy-4-geranyloxy-1-butyl-2(1H)-quinolinone, 7-nitro-3-formyloxy-4-hydroxy-1-butyl-2(1H)-quinolinone, 7-nitro-3,4-dimethoxy-1-butyl-2(1H)-quinolinone, 7-nitro-4-butoxy-3-methoxy-1-butyl-2(1H)-quinolinone, 7-nitro-4-hexyloxy-3-methoxy-1-butyl-2(1H)-quinolinone, 7-nitro-3methoxy-4-(3methyl-2-butenyloxy)-1-butyl-2(1H)-quinolinone, 7-nitro-4-geranyloxy-3-methoxy-1-butyl-2(1H)-quinolinone, 7-nitro-4-hydroxy-3-methoxy-1-butyl-2(1H)-quinolinone, 7-nitro-3-isopropoxy-4-methoxy-1-butyl-2(1H)-quinolinone, 7-nitro-4-butoxy-3-isopropoxy-1-butyl-2(1H)-quinolinone, 7-nitro-4-hexyloxy-3-isopropoxy-1-butyl-2(1H)-quinolinone, 7-nitro-3-isopropoxy-4-(3-methyl-2-butenyloxy)-1-butyl-2(1H)-quinolinone, 7-nitro-4-geranyloxy-3-isopropoxy-1-butyl-2(1H)-quinolinone, 7-nitro-4-hydroxy-3-isopropoxy-1-butyl-2(1H)-quinolinone, 7-nitro-3-butoxy-4-methoxy-1-butyl-2(1H)-quinolinone, 7-nitro-3,4-dibutoxy-1-butyl-2(1H)-quinolinone, 7-nitro-3-butoxy-4-hexyloxy- 1-butyl-2(1H)-quinolinone, 7-nitro-3-butoxy-4-(3-methyl-2-butenyloxy)-1-butyl-2(1H)-quinolinone, 7-nitro-3-butoxy-4-geranyloxy-1-butyl-2(1H)-quinolinone, 7-nitro-3-butoxy-4-hydroxy-1-butyl-2(1H)-quinolinone, 7-nitro-3-hexyloxy-4-methoxy-1-butyl-2(1H)-quinolinone, 7-nitro-4-butoxy-3-hexyloxy-1-butyl-2(1H)-quinolinone, 7-nitro-3,4-dihexyloxy-1-butyl-2(1H)-quinolinone, 7-nitro-3-hexyloxy-4-(3-methyl-2-butenyloxy)-1-butyl-2(1H)-quinolinone, 7-nitro-4-geranyloxy-3-hexyloxy-1-butyl-2(1H)-quinolinone, 7-nitro-3-hexyloxy-4-hydroxy-1-butyl-2(1H)-quinolinone, 7-nitro-4-methoxy-3-(2-methylpentyloxy)-1-butyl-2(1H)-quinolinone, 7-nitro-4-butoxy-3-(2-methylpentyloxy)-1-butyl-2(1H)-quinolinone, 7-nitro-4-hexyloxy-3-(2-methylpentyloxy)-1-butyl-2(1H )-quinolinone, 7-nitro-4-(3-methyl-2-butenyloxy)-3-(2-methylpentyloxy)-1-butyl-2(1H)-quinolinone, 7-nitro-4-geranyloxy-3-(2-methylpentyloxy)-1-butyl-2(1H)-quinolinone, 7-nitro-4-hydroxy-3-(2-methyl-pentyloxy)-1-butyl-2(1H)-quinolinone, 7-nitro-4-methoxy-3-octyloxy-1-butyl-2(1H)-quinolinone, 7-nitro-4-butoxy-3-octyloxy-1-butyl-2(1H)-quinolinone, 7-nitro-4-hexyloxy-3-octyloxy-1-butyl-2(1H)-quinolinone, 7-nitro-4-(3-methyl-2-butenyloxy)-3-octyloxy-1-butyl-2(1H)-quinolinone, 7-nitro-4-geranyloxy-3-octyloxy-1-butyl-2(1H)-quinolinone, 7-nitro-4-hexyloxy-3-octyloxy-1-butyl-2(1H)-quinolinone, 7-nitro-4-methoxy-3-(2-propenyloxy)-1-butyl-2(1H)-quinolinone, 7-nitro-4-butoxy-3-(2-propenyloxy)-1-butyl-2(1H-)-quinolinone, 7-nitro-4-hexyloxy-3-(2-propenyl-oxy)-1-butyl-2(1H)-quinolinone, 7-nitro-4-(3-methyl-2-butenyloxy)-3-(2-propenyl-oxy)-1-butyl-2(1H)-quinolinone, 7-nitro-4-geranyloxy-3-(2-propenyloxy)-1-butyl-2(1H)-quinolinone, 7-nitro-4-hydroxy-3-(2-propenyloxy)-1-butyl-2(1H)-quinolinone, 7-nitro-3-geranyloxy-4-methoxy-1-butyl-2(1H)-quinolinone, 7-nitro-4-butoxy-3-geranyloxy-1-butyl-2(1H)-quinolinone, 7-nitro-3-geranyloxy-4-hexyloxy-1-butyl-2(1H)-quinolinone, 7-nitro-3-geranyloxy-4-(3-methyl-2-butenyloxy)-1-butyl-2(1H)-quinolinone, 7-nitro-3,4-digeranyloxy-1-butyl-2(1H)-quinolinone, 7-nitro-3-geranyloxy-4-hydroxy-1-butyl-2(1H)-quinolinone, 7-nitro-3-hydroxy-4-methoxy-1-butyl-2(1H)-quinolinone, 7-nitro-4-butoxy-3-hydroxy-1-butyl-2(1H)-quinolinone, 7-nitro-4-hexyloxy-3-hydroxy-1-butyl-2(1H)-quinolinone, 7-nitro-3-hydroxy-4-(3-methyl-2-butenyloxy)-1-butyl-2(1H)-quinolinone, 7-nitro-4-geranyloxy-3-hydroxy-1-butyl-2(1H)-quinolinone, 7-nitro-3,4-dihydroxy-1-butyl-2(1H)-quinolinone, 7-nitro-3-acetoxy-4-methoxy-1-hexyl-2(1H)-quinolinone, 7-nitro-3-acetoxy-4-butoxy)-1-hexyl-2(1H)-quinolinone, 7-nitro-3-acetoxy-4-butoxy-1-hexyl-2(1H)-quinolinone, 7-nitro-3-acetoxy-4-hexyloxy-1-hexyl-2(1H)-quinolinone, 7-nitro-3-acetoxy-4-(3-methyl-2-butenyloxy)-1-hexyl-2-(1H)-quinolinone, 7-nitro-3-acetoxy-4geranyloxy-1-hexyl-2(1H)-quinolinone, 7-nitro-3-acetoxy-4-hydroxy-1-hexyl-2(1H)-quinolinone, 7-nitro-3-formyloxy-4-methoxy-1-hexyl-2(1H)-quinolinone, 7-nitro-4-butoxy-3-formyloxy-1-hexyl-2(1H)-quinolinone, 7-nitro-3-formyloxy-4-hexyloxy-1-hexyl-2(1H)-quinolinone, 7-nitro-3-formyloxy-4-(3-methyl-2-butenyloxy)-1-hexyl-2(1H)-quinolinone, 7-nitro-3-formyloxy-4-geranyloxy-1-hexyl-2(1l)-quinolinone, 7-nitro-3-formyloxy-4-hydroxy-1-hexyl-2(1H)-quinolinone, 7-nitro-3,4-dimethoxy-1-hexyl-2(1H)-quinolinone, 7-nitro-4-butoxy-3-methoxy-1-hexyl-2(1H)-quinolinone, 7-nitro-4-hexyloxy-3-methoxy-1-hexyl-2(1H)-quinolinone, 7-nitro-3-methoxy-4-(3-methyl-2-butenyloxy)-1-hexyl-2(1H)-quinolinone, 7-nitro-4-geranyloxy-3-methoxy-1-hexyl-2(1H)-quinolinone, 7-nitro-4-hydroxy-3-methoxy-1-hexyl-2(1H)-quinolinone, 7-nitro-3-isopropoxy-4-methoxy-1-hexyl-2(1H)-quinolinone, 7-nitro-4-butoxy-3-isopropoxy-1-hexyl-2(1H)-quinolinone, 7-nitro-4-hexyloxy-3-isopropoxy-1-hexyl-2(1H)-quinolinone, 7-nitro-3-isopropoxy-4-(3-methyl-2-butenyloxy)-1-hexyl-2(1H)-quinolinone, 7-nitro-4-geranyloxy-3-isopropoxy-1-hexyl-2(1H)-quinolinone, 7-nitro-4-hydroxy-3-isopropoxy-1-hexyl-2(1H)-quinolinone, 7-nitro-3-butoxy-4-methoxy-1-hexyl-2(1H)-quinolinone, 7-nitro-3,4-dibutoxy-1-hexyl-2(1H)-quinolinone, 7-nitro-3-butoxy-4-hexyloxy-1-hexyl-2(1H)-quinolinone, 7-nitro-3-butoxy-4-(3-methyl-2-butenyloxy)-1-hexyl-2(1H)-quinolinone, 7-nitro-3-butoxy-4-geranyloxy-1-hexyl-2(1H)-quinolinone, 7-nitro-3-butoxy-4-hydroxy-1-hexyl-2(1H)-quinolinone, 7-nitro-3-hexyloxy-4-methoxy-1-hexyl-2(1H)-quinolinone, 7-nitro-4-butoxy-3-hexyloxy-1-hexyl-2(1H)-quinolinone, 7-nitro-3,4-dihexyloxy-1-hexyl-2(1H)-quinolinone, 7-nitro-3-hexyloxy-4-(3-methyl-2-butenyloxy)-1-hexyl-2(1H)-quinolinone, 7-nitro-4-geranyloxy-3-hexyloxy-1-hexyl-2(1H)-quinolinone, 7-nitro-3-hexyloxy-4-hydroxy-1-hexyl-2(1H)-quinolinone, 7-nitro-4-methoxy-3-(2-methylpentyloxy)-1-hexyl-2(1H)-quinolinone, 7-nitro-4-butoxy-3-(2-methylpentyloxy)-1-hexyl-2(1H)-quinolinone, 7-nitro-4-hexyloxy-3-(2-methylpentyloxy)-1-hexyl-2(1H)-quinolinone, 7-nitro-4-(3-methyl-2-butenyloxy)-3-(2-methylpentyloxy)-1-hexyl-2(1H)-quinolinone, 7-nitro-4-geranyloxy-3-(2-methylpentyloxy)-1-hexyl-2(1H)-quinolinone, 7-nitro-4-hydroxy-3-(2-methylpentyloxy)-1-hexyl-2(1H)-quinolinone, 7-nitro-4-methoxy-3-octyloxy-1-hexyl-2(1H)-quinolinone, 7-nitro-4-butoxy-3-octyloxy-1-hexyl-2(1H)-quinolinone, 7-nitro-4-hexyloxy-3-octyloxy-1-hexyl-2(1H)-quinolinone, 7-nitro-4-(3-methyl-2-butenyloxy)-3-octyloxy-1-hexyl-2(1H)-quinolinone, 7-nitro-4-geranyloxy-3-octyloxy-1-hexyl-2(1H)-quinolinone, 7-nitro-4-hydroxy-3-octyloxy-1-hexyl-2(1H)-quinolinone, 7-nitro-4-methoxy-3-(2-propenloxy)-1-hexyl-2-(1H)-quinolinone, 7-nitro-4-butoxy-3-(2-propenyloxy)-1-hexyl- 2(1H)-quinolinone, 7-nitro-4-hexyloxy-3-(2-propenyloxy)-1-hexyl-2(1H)-quinolinone, 7-nitro-4-(3-methyl-2-butenyloxy)-3-(2-propenyloxy)-1-hexyl-2(1H)-quinolinone, 7-nitro-4-geranyloxy-3-(2-propenyloxy)-1-hexyl-2(1H)-quinolinone, 7-nitro-4-hydroxy-3-(2-propenyloxy)-1-hexyl-2(1H)-quinolinone, 7-nitro-3-geranyloxy-4-methoxy-1-hexyl-2(1H)-quinolinone, 7-nitro-4-butoxy-3-geranyloxy-1-hexyl-2(1H)-quinolinone, 7-nitro-3-geranyloxy-4-hexyloxy-1-hexyl-2(1H)-quinolinone, 7-nitro-3-geranyloxy-4-(3-methyl-2-butenyloxy)-1-hexyl-2(1H)-quinolinone, 7-nitro-3,4-digeranyloxy-1-hexyl-2(1H)-quinolinone, 7-nitro-3-geranyloxy-4-hydroxy-1-hexyl-2(1H)-quinolinone, 7-nitro-3-hydroxy-4-methoxy-1-hexyl-2(1H)-quinolinone, 7-nitro-4-butoxy-3-hydroxy-1-hexyl-2(1H)-quinolinone, 7-nitro-4-hexyloxy -3-hydroxy-1-hexyl-2(1H)-quinolinone, 7-nitro-3-hydroxy-4-(3-methyl-2-butenyloxy)-1-hexyl-2(1H)-quiniolinone, 7-nitro-4-geranyloxy-3-hydroxy-1-hexyl-2(1H)-quinolinone, 7-nitro-3,4-dihydroxy-1-hexyl-2(1H)-quinolinone, 7-nitro-3-acetoxy-4-methoxy-1-octyl-2(1H)-quinolinone, 7-nitro-3-acetoxy-4-ethoxy-1-octyl-2(1H)-quinolinone, 7-nitro-3-acetoxy-4-butoxy-1-octyl-2(1H)-quinolinone, 7-nitro-3-acetoxy-4-hexyloxy-1-octyl-2(1H)-quinolinone, 7-nitro-3-acetoxy-4-(3-methyl-2-butenyloxy)-1-octyl-2(1H)-quinolinone, 7-nitro-3-acetoxy-4-geranyloxy-1-octyl-2(1H)-quinolinone, 7nitro-3acetoxy-4-hydroxy-1-octyl-2(1H)-quinolinone, 7-nitro-3-formyloxy-4-methoxy-1-octyl-2(1H)-quinolinone, 7-nitro-4-butoxy-3-formyloxy-1-octyl-2(1H)-quinolinone, 7-nitro-3-formyloxy-4-hexyloxy-1-octyl-2(1H)-quinolinone, 7-nitro-3-formyloxy-4-(3-methyl-2-butenyloxy)-1-octyl-2(1H)-quinolinone, 7-nitro-3-formyloxy-4-geranyloxy-1-octyl-2(1H)-quinolinone, 7-nitro-3-formyloxy-4-hydroxy-1-octyl-2(1H)-quinolinone, 7-nitro-3,4-dimethoxy-1-octyl-2(1H)-quinolinone, 7-nitro-4-butoxy-3-methoxy-1-octyl-2(1H)-quinolinone, 7-nitro-4-hexyloxy-3-hydroxy-1-octyl-2(1H)-quinolinone, 7-nitro-4-hexyloxy-3-methoxy-1-octyl-2(1H)-quinolinone, 7-nitro-3-methoxy-4-(3-methyl-2-butenyloxy)-1-octyl-2(1H)-quinolinone, 7-nitro-4-geranyloxy-3-methoxy-1-octyl2(1H)-quinolinone, 7-nitro-4-hydroxy-3-methoxy-1-octyl-2(1H)-quinolinone, 7-nitro-3-isopropoxy-4-methoxy-1-octyl-2(1H)-quinolinone, 7-nitro-4-butoxy-3-isopropoxy-1-octyl-2(1H)-quinolinone, 7-nitro-4-hexyloxy-3-isopropoxy-1-octyl-2(1H)-quinolinone, 7-nitro-3-isopropoxy-4-(3-methyl-2-butenyloxy)-1-octyl-2(1H)-quinolinone, 7-nitro-4-geranyloxy-3-isopropoxy-1-octyl-2(1H)-quinolinone, 7-nitro-4-hydroxy-3-isopropoxy-1-octyl-2(1H)-quinolinone, 7-nitro-3-butoxy-4-methoxy-1-octyl-2(1H)-quinolinone, 7-nitro-3,4-dibutoxy-1-octyl-2(1H)-quinolinone, 7-nitro-3-butoxy-4-hexyloxy-1-octyl-2(1H)-quinolinone, 7-nitro-3-butoxy 4-(3-methyl-2-butenyloxy)-1-octyl- 2(1H)-quinolinone, 7-nitro-3-butoxy-4-geranyloxy-1-octyl2(1H)-quinolinone, 7-nitro-3-butoxy-4-hydroxy-1-octyl-2(1H)-quinolinone, 7-nitro-3-hexyloxy-4-methoxy-1-octyl-2(1H)-quinolinone, 7-nitro-4-butoxy-3-hexyloxy-1-octyl-2(1H)-quinolinone, 7-nitro-3,4-dihexyloxy-1-octyl-2(1H)-quinolinone, 7-nitro-3-hexyloxy-4-(3-methyl-2-butenyloxy)-1-octyl-2(1H)-quinolinone, 7-nitro-4- geranyloxy-3-hexyloxy-1-octyl-2(1H)-quinolinone, 7-nitro-3-hexyloxy-4-hydroxy-1-octyl-2(1)-quinolinone, 7-nitro-4-methoxy-3-(2-methylpentyloxy)-1-octyl-2(1H)-quinolinone, 7-nitro-4-butoxy-3-(2-methylpentyloxy)-1-octyl-2(1H)-quinolinone, 7-nitro-4-hexyloxy-3-(2-methylpentyloxy)-1-octyl-2(1H)-quinolinone, 7-nitro-4-(3-methyl-2-butenyloxy)-3-(2-methylpentyloxy)-1-octyl-2(1H)-quinolinone, 7-nitro-4-geranyloxy-3-(2-methylpentyloxy)-1-octyl-2(1H)-quinolinone, 7-nitro-4-hydroxy-3-(2-methylpentyloxy)-1-octyl-2(1H)-quinolinone, 7-nitro-4-methoxy-3-octyloxy-1-octyl-2(1H)-quinolinone, 7-nitro-4-butoxy-3-octyloxy-1-octyl-2(1H)-quinolinone, 7-nitro-4-hexyloxy-3-octyloxy-1-octyl-2(1H)-quinolinone, 7-nitro-4-(3-methyl-2-butenyloxy)-3-octyloxy-1-octyl-2(1H)-quinolinone, 7-nitro-4-geranyloxy-3-octyloxy-1-octyl-2(1H)-quinolinone, 7-nitro-4-hydroxy-3-octyloxy-1-octyl-2(1H)-quinolinone, 7-nitro-4-methoxy-3-(2-propenyloxy)-1-octyl-2(1H)-quinolinone, 7-nitro-4-butoxy-3-(2-propenyloxy)-1-octyl-2(1H)-quinolinone, 7-nitro-4-hexyloxy-3-(2-propenyloxy)-1-octyl-2(1H)-quinolinone, 7-nitro-4-(3-methyl-2-butenyloxy)-3-(2-propenyloxy)-1-octyl-2(1H)-quinolinone, 7-nitro-4-geranyloxy-3-(2-propenyloxy)-1-octyl-2(1H)-quinolinone, 7-nitro-4-hydroxy-3-(2-propenyloxy)-1-octyl-2(1H)-quinolinone, 7-nitro-3-geranyloxy-4-methoxy-1-octyl-2(1H)-quinolinone, 7-nitro-4-butoxy-3-geranyloxy-1-octyl-2(1H)-quinolinone, 7-nitro-3-geranyloxy-4-hexyloxy-1-octyl-2(1H)-quinolinone, 7-nitro-3-geranyloxy-4-(3-methyl-2-butenyloxy)-1-octyl-2(1H)-quinolinone, 7-nitro-3,4-digeranyloxy-1-octyl-2(1H)-quinolinone, 7-nitro-3-geranyloxy-4-hydroxy-1 octyl-2(1H)-quinolinone, 7-nitro-3-hydroxy-4-methoxy-1-octyl-2(1H)-quinolinone, 7-nitro-4-butoxy-3-hydroxy-1-octyl-2(1H)-quinolinone, 7-nitro-4-hexyloxy-3-hydroxy-1-octyl-2(1H)-quinolinone, 7-nitro-3-hydroxy-4-(3-methyl-2-butenyloxy)-1-octyl-2(1H)-quinolinone, 7-nitro-4-geranyloxy-3-hydroxy-1-octyl-2(1H)-quinolinone, 7-nitro-3,4-dihydroxy-1-octyl-2(1H)-quinolinone.

Since the 7-aminoquinolinone derivatives and physiologically acceptable salts of the present invention (to be referred to as "the compound of the present invention" hereinafter) have a function to inhibit both immediate and delayed type allergic reactions and low toxicity as will be described later in examples, they are useful as anti-allergic agents for the treatment or prevention of various allergic diseases.

The term "allergic diseases" as used herein means allergic diseases resulting from excess activation of the biological immune mechanism caused by extrinsic or intrinsic antigens, which include immediate type asthma, delayed type asthma, bronchial asthma, pediatric asthma, atopic dermatitis, allergic dermatitis, urticaria, eczema, allergic conjunctivitis, allergic rhinitis, hay fever, food allergy, allergic gastroenteritis, allergic colitis, contact dermatitis, autoimmune disease and the like.

The anti-allergic agent which comprises the compound of the present invention as an active ingredient can be administered orally (internal use or inhalation) or parenterally (for example, intravenous injection, subcutaneous injection, percutaneous absorption, rectal administration or the like). Such a pharmaceutical agent can be made into various dosage forms according to the purpose, such as tablets, capsules, granules, fine subtilaes, powders, troches, sublingual tablets, suppositories, ointments, injections, emulsions, suspensions, medicated syrups and the like. These dosage forms can be prepared in accordance with known techniques making use of pharmaceutically acceptable carriers which are commonly used in this type of drugs, such as excipients, bonding agents, disintegrators, lubricants, preservatives, antioxidative agents, isotonic agents, buffering agents, coating agents, sweetening agents, dissolving agents, bases, dispersing agents, stabilizing agents, coloring agents and the like.

Illustrative examples of these pharmaceutically acceptable carriers are listed in the following.

Firstly, as excipients, the following can be listed: starch and derivatives of starch (such as dextrin, carboxymethyl starch and the like), cellulose and derivatives of cellulose (such as methylcellulose, hydroxypropylmethylcellulose and the like), sugars (such as lactose, sucrose, glucose and the like), silicic acid and silicates (such as naturally occurring aluminum silicate, magnesium silicate and the like), carbonates (such as calcium carbonate, magnesium carbonate, sodium hydrogencarbonate and the like), aluminum magnesium hydroxide, synthetic hydrotalcite, polyoxyethylene derivatives, glycerin monostearate, sorbitan monooleic acid and the like.

As bonding agents, the following can be listed: starch and starch derivatives (such as alpha starches, dextrin and the like), cellulose and derivatives of cellulose (such as ethyl cellulose, sodium carboxymethyl cellulose, hydroxypropylmethyl cellulose and the like), gum arabic, traganth, gelatin, sugars (such as glucose, sucrose and the like), ethanol, polyvinyl alcohols and the like.

As disintegrators, the following can be listed: starch and starch derivatives (such as carboxymethyl starch, hydroxypropyl starch and the like), cellulose and cellulose derivatives (such as sodium carboxymethyl cellulose, crystal cellulose, hydroxypropylmethyl cellulose and the like), carbonates (such as calcium carbonate, calcium hydrogencarbonate and the like), traganth, gelatins, agar and the like.

As lubricants, the following can be listed: stearic acid, calcium stearate, magnesium stearate, talc, silicic acid and its salts (such as light silicic anhydrides, naturally occurring aluminum silicates and the like), titanium oxide, calcium hydrogen phosphate, dry aluminum hydroxide gel, macrogol and the like.

As preservatives, the following can be listed: p-hydroxybenzoates, sulfites (such as sodium sulfites, sodium pyrosulfites and the like), phosphates (such as sodium phosphates, calcium polyphosphates, sodium polyphosphates, sodium methaphosphate and the like), alcohols (such as chlorobutanol, benzyl alcohol and the like), benzalkonium chloride, benzethonium chloride, phenol, cresol, chlorocresol, dihydroacetic acid, sodium dihydroacetate, glycerin sorbic acid, sugars and the like.

As anti-oxidative agents, the following can be listed: sulfites (such as sodium sulfite, sodium hydrogen sulfite and the like), rongalite, erythorbic acid, L-ascorbic acid, cysteine, thioglycerol, butylhydroxyanisol, dibutylhydroxytoluene, propylgallic acid, ascorbyl palmitate, dl-α-tocopherol and the like.

As isotonic agents, the following can be listed: sodium chloride, sodium nitrate, potassium nitrate, dextrin, glycerin, glucose and the like.

As buffering agents, the following can be listed: sodium carbonate, hydrochloric acid, boric acid, phosphates (such as sodium hydrogenphosphate) and the like.

As coating agents, the following can be listed: cellulose derivatives (such as hydroxypropyl cellulose, cellulose acetate phthalate, hydroxypropylmethyl cellulose phthalate and the like), shellac, polyvinylpyrrolidone, polyvinylpyridines (such as poly-2-vinyl-5pyridine, poly-2-vinylethylpyridine and the like), polyvinylacetyl diethylaminoacetate, polyvinyl alcohol phthalate, methacrylate, methacrylate copolymers and the like.

As sweetening agents, the following can be listed: sugars (such as glucose, sucrose, lactose and the like), sodium saccharin, sugar alcohols and the like.

As dissolving agents, the following can be listed: ethylenediamine, nicotinamide, sodium saccharin, citric acid, citrates, sodium benzoic acid, soaps, polyvinylpyrrolidone, polysolvates, sorbitan fatty acid esters, glycerin, propylene glycol, benzyl alcohols and the like.

As bases, the following can be listed: fats (such as lard and the like), vegetable oils (such as olive oil, sesame oil and the like), animal oil, lanolin acid, petrolatums, paraffin, wax, resins, bentonite, glycerin, glycol oils, higher alcohols (such as stearyl alcohol, cetanol) and the like.

As dispersing agents, the following can be listed: gum arabic, traganth, cellulose derivatives (such as methyl cellulose and the like), stearic acid polyesters, sorbitan sesquioleate, aluminum monostearate, sodium alginate, polysolvates, sorbitan fatty acid esters and the like.

Lastly, as stabilizing agents, the following can be listed: sulfites (such as sodium hydrogen sulfite and the like), nitrogen, carbon dioxide and the like.

Though the content of the compound of the present invention in these pharmaceutical preparations varies depending on the dosage forms, it may be contained preferably in a concentration of from 0.01 to 100% by weight.

Dose of the anti-allergic agent of the present invention can be varied over a broad range depending on each warm-blooded animal including human and the like, to be treated, extent of each disease, doctor's judgement and the like. In general, however, it may be administered in a dose of from 0.01 to 50 mg, preferably from 0.01 to 10 mg, as the active ingredient per day per kg body weight in the case of oral administration or in a dose of from 0.01 to 10 mg, preferably from 0.01 to 5 mg, as the active ingredient per day per kg body weight in the case of parenteral administration. The daily dose described above may be used in one portion or in divided portions and changed optionally in accordance with the extent of diseases and doctor's judgement.

The following summarizes a process for the production of the 7-aminoquinolinone derivative and the 7-nitroquinolinone derivative of the present invention.

The 7-aminoquinolinone derivative represented by the formula (I) and the 7-nitroquinolinone derivative represented by the formula (II), a useful intermediate for synthesis of 7-aminoquinolinone derivative, can be produced for example in the following manner in accordance with the following reaction scheme: wherein, $R_1$~$R_5$ represent same meanings defined in the formula (I) and the formula (II) described above.

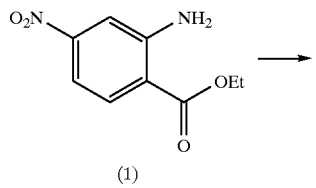

(1)

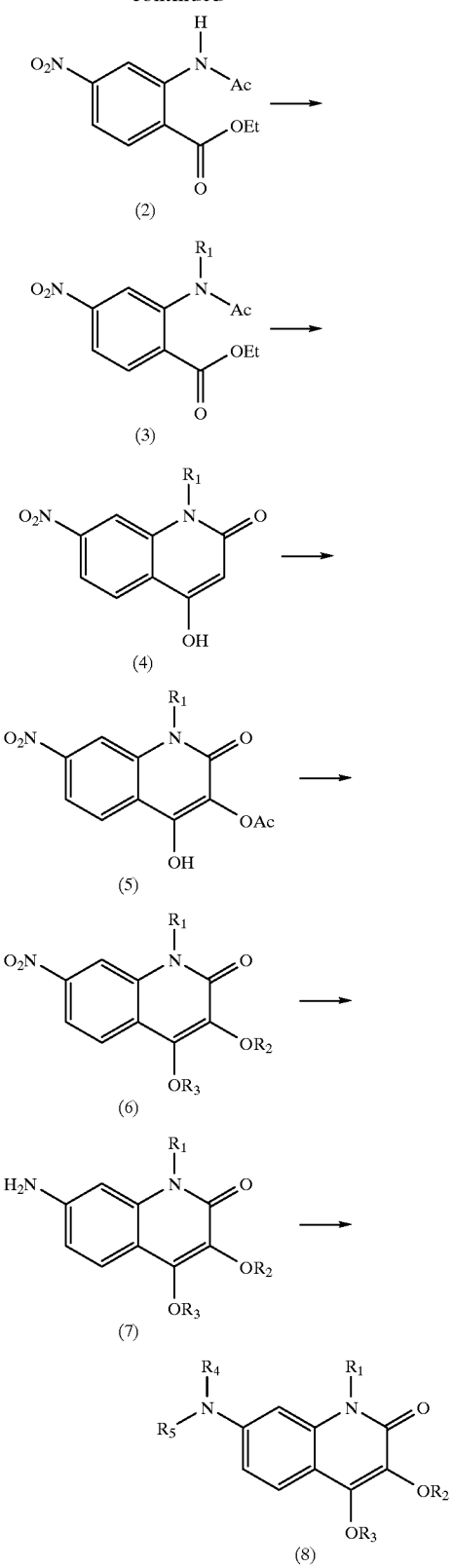

As a first step, 4-nitroanthranilic acid is acetylated to give compound (2). The reaction may be carried out by making use of usual acetylating agent, for example, acetic anhydride or acetyl chloride. The reaction may be carried out at a temperature of from 0 to 120°, preferably from 60 to 100°. The reaction time varies depending on acetylating agent to be used and reaction temperature, generally from 0.5 to 3 hours. Though the reaction can be carried out without a substance to accelerate the reaction, a basic substance may be used as an accelerator. Amine is preferable as a basic substance, for example triethylamine, pyridine and the like.

Next, as a second step, alkylation of the thus obtained compound (2) is carried out, making use of alkyl halide as an alkylating agent. Preferred examples of the base to be used include inorganic salts such as sodium bicarbonate, sodium carbonate, potassium carbonate and the like and alcoholate bases such as sodium ethoxide, potassium t-butoxide and the like and sodium hydride. The reaction may be carried out in a solvent. Preferred examples of the solvent include hydrocarbones such as benzene, toluene and the like, ether solvents such as diethyl ether, tetrahydrofurane, 1,2-dimethoxy ethane and the like, amide solvents such as N,N-dimethyl-formamide and the like. The reaction may be carried out at a temperature of from 0 to 100°, preferably from 20 to 60°, for a period of generally from 1 to 5 hours. In the case of $R_1$ is hydrogen, following cyclization reaction may be carried out without performing the alkylation reaction described above.

Next, as a third step, the thus obtained compound (3) is subjected to cyclization reaction, affording compound (4). This reaction is performed by treating compound (3) with a basic substance in organic solvent. Preferred examples of the base to be used include alcoholate bases such a sodium methoxide, sodium ethoxide, potassium t-butoxide and the like, sodium hydride, potassium hydride, lithium diisopropylamide, lithium bis(trimethylsilyl)amide and the like. The reaction may be carried out in a solvent. Preferred examples of the solvent include hydrocarbones such as benzene, toluene and the like, alcohol solvents such as methanol, ethanol and the like, ether solvents such as diethyl ether, tetrahydrofurane, 1,2-dimethoxy ethane and the like, amide solvents such as N,N-dimethylformamide and the like. The reaction may be carried out at a temperature of from −50 to 100°, preferably from 0 to 50°, for a period of generally from 1 to 5 hours.

Next, as a fourth step, the thus obtained compound (4) is subjected to oxidation reaction by performing acyloxylation reaction at 3-position of the compound (4). Preferred examples of the oxidation agent to be used include iodobenzene diacetate and the like. In this reaction, the desired compound can be obtained directly by the reaction with iodobenzene diacetate in a organic acid, but also can be obtained by treating an iodonium compound to be isolated as an intermediate with an organic acid. The reaction may be carried out at a temperature of preferably from 30 to 80°, for a period of generally from 2 to 5 hours.

Next, in order to introduce $R_2$ group and $R_3$ group into compound (5), when $R_2$ group is hydrogen, deacylation reaction is carried out in usual hydrolysis manner, when $R_2$ group and $R_3$ group are not hydrogen, alkylation reaction or alkenylation reaction are carried out after introduction of preferable protecting group, then deprotection reaction is performed. Preferred examples of the protecting group to be used include hydroxy protecting group, for example methoxymethyl group. Thus the compounds represented by the formula (II), can be produced.

Next, compound (7) is prepared by performing reduction reaction of nitro group of the obtained compound (6), then compound (8) can be produced by following alkylation reaction or alkenylation reaction or aralkylation reaction. In the case of performing these alkylation reaction or alkenylation reaction or aralkylation reaction, when the compound (7) has hydroxy group at 3-position or 4-position, preferable hydroxy protecting group may be introduce into the compound. This reduction reaction is effected by hydrogenation in an atmosphere of hydrogen gas making use of a metal catalyst in a organic solvent. Examples of the metal catalyst include palladium, platinum and the like catalysts which may be used in an amount of from 1 to 10% by weight based on the compound. The reaction in hydrogen gas may be carried out under a pressurized condition or under normal pressure. The reaction may be carried out at a temperature from 0 to 100°, preferably from 20 to 50°, for a period of generally from 1 to 5 hours. This reduction reaction also can be proceeded, making use of metals such as tin and zinc. Thus the compounds represented by the formula (I) can be produced.

The following examples are intended to illustrate this invention, however these examples are intended to illustrate the invention and not to be construed to limit the scope of the invention.

Reference Example 1

Ethyl 2-acetylamino-4-nitro-benzoate (compound 1)

A mixture of 4.45 g of ethyl 4-nitroanthranilate (21.2 mmol) and 9 ml of acetic anhydride was stirred at 90° for 1 hour. The reaction mixture was concentrated under reduced pressure, the residue was crystallized from dichloromethane and hexane to give 4.98 g of the title compound (1). (yield=93%)

$^1$H-NMR (CDCl$_3$, δ-TMS) 8.15 (m, 3H), 6.05 (bs, 1H), 4.43 (q, 2H, J=7.0 Hz), 1.82 (s, 3H), 1.41 (t, 3H)

IR (KBr, cm$^{-1}$): 3240, 2850, 1740, 1550, 1345

Reference Examples 2

Ethyl 2-acetylmethylamino-4-nitrobenzoate (compound 2) 1.35 g of ethyl 2-acetylamino-4-nitrobenzoate (5.4 mmol) was dissolved in 15 ml of DMF, 220 mg of sodium hydride (purity 60%, 5.5 mmol) was added to the mixture with cooling on an ice bath and stirred for 15 minutes. After 1.50 g of methyl iodide (10.7 mmol) was added, the mixture was stirred for additional 40 minutes. To the mixture added were benzene and water, and extracted with benzene. The organic layer was concentrated under reduced pressure, the obtained residue was crystallized from ethyl acetate and hexane to give 1.16 g of the title compound (2). (yield=81%)

$^1$H-NMR (CDCl$_3$, δ-TMS) 8.15 (m, 3H), 4.43 (q, 2H, J=, 7.0 Hz), 3.25 (s, 3H), 1.82 (s, 3H), 1.41 (t, 3H)

IR (KBr, cm$^{-1}$): 2850, 1740, 1550, 1345

Reference Example 3

7-nitro-4-hydroxy-1-methyl-2(1H)-quinolinone (compound 3)

1.48 g of ethyl 2-acetylmethylamino-4-nitrobenzoate (5.6 mmol) was dissolved in 9 ml of DMF, 220 mg of sodium hydride (purity 60%, 5.5 mmol) was added to the mixture with cooling on an ice bath and stirred overnight. The reaction mixture was added to 20 ml of water and acidified with 4N-HCl. The resulting precipitate was filtered and dried to give 0.96 g of the title compound (3). (yield=78%)

$^1$H-NMR(CDCl$_3$, δ-TMS) 11.15 (s, 1H), 8.21 (m, 3H), 5.67 (s, 1H), 3.55 (s, 3H)

IR$_4$ (KBr, cm$^{-1}$):3275, 1680, 1555, 1345

EXAMPLE 1

7-nitro-3-acetoxy-4-hydroxy-1-methyl-2(1H)-quinolinone (compound 4)

To a mixture of 9.72 g of 7-nitro-4-hydroxy-1-methyl-2(1H)-quinolinone (44.2 mmol) in 50 ml of dichloromethane was added 14.0 g of iodobenzene diacetate (43.5 mmol) and stirred at room temperature for 3 hours. The mixture was filtered and the filtrate was dried under reduced pressure to give 14.90 g of phenyl iodonium salt. This salt was added to 150 ml of acetic acid and stirred at 70° C. for 3 hours. The mixture was concentrated under reduced pressure, the resulting crude product was washed with dichloromethane to give 6.98 g of the title compound (4). (field=56%)

$^1$H-NMR ($d_6$-DMSO, 67 -TMS) 11.83 (s, 1H), 8.27 (s, 1H), 8.18 (d, 1H, J=7.2 Hz), 8.01 (d, 1H, J=7.2 Hz), 3.68 (s, 3H), 2.30 (s, 3H)

IR (KBr, cm$^{-1}$): 3275, 1745, 1680, 1555, 1345

Elemental analysis for $C_{12}H_{10}N_2O_6$ Calculated (%):C 51.80; H 3.62; N 10.07; O 34.51 Found (%):C 51.75; H 3.67; N 10.26; O 34.32

EXAMPLE 2

7-nitro-3-acetoxy-4-methoxy-1-methyl-2(1H)-quinolinone (compound 5)

To a mixture of 1.50 g of 7-nitro-3-acetoxy-4-hydroxy-1-methyl-2(1H)-quinolinone (5.4 mmol) in 15 ml of DMF were added 1.12 g of potassium carbonate (8.1 mmol) and 0.76 g of methyl iodide (5.4 mmol) and stirred at room temperature for 3 hours. The reaction mixture was added to water and extracted with benzene. The organic layer was concentrated under reduced pressure to give a crude product. Purification of this crude by column chromatography on silica gel (hexane/ethyl acetate=1/1 as an eluent) gave 0.68 g of the title compound (5). (yield=43%)

$^1$H-NMR ($d_6$-DMSO, δ-TMS) 8.27 (s, 1H), 8.18 (d, 1H, J=7.2 Hz), 8.01 (d, 1H, J=7.2 Hz), 4.32 (s, 3H), 3.68 (s, 3H), 2.30 (s, 3H)

IR (KBr, cm$^{-1}$): 1745, 1680, 1555, 1345

Elemental analysis for $C_{13}H_{12}N_2O_6$ Calculated (%):C53.53; H4.14; N9.59; O32.85 Found (%):C53.55; H4.05; N9.66; O32.74

EXAMPLE 3

7-amino-3-acetoxy-4-methoxy-1-methyl-2(1H)-quinolinone (compound 6)

A mixture of 0.95 g of 7-nitro-3-acetoxy-4-methoxy-1-methyl-2(1H)-quinolinone (3.3 mmol) and 95 mg of 10% palladium carbon in 20 ml of THF was stirred under hydrogen gas at room temperature for 3 hours. After hydrogen gas was replaced by nitrogen gas, the mixture was filtered and the filtrate was concentrated under reduced pressure. The resulting residue was purified by column chromatography on silica gel (hexane/ethyl acetate=1/2 as an eluent), affording 0.75 g of the title compound (6). (yield=87%)

$^1$H-NMR ($d_6$-DMSO, δ-TMS) 7.95 (s, 1H), 7.85 (d, 1H, J=7.2 Hz), 7.50 (d, 1H, J=7.2 Hz), 6.05(bs, 2H), 4.32 (s, 3H), 3.68 (s, 3H), 2.30 (s, 3H)

IR (KBr, cm$^{-1}$): 3280, 1745, 1675, 1250

Elemental analysis for $C_{13}H_{14}N_2O_4$ Calculated (%):C59.53; H5.38; N10.68; O24.40 Found (%):C59.55; H5.45; N10.66; O24.34

EXAMPLE 4

7-nitro-3,4-dihydroxy-1-methyl-2(1H)-quinolinone (compound 7)

To a mixture of 2.56 g of 7-nitro-3-acetoxy-4-hydroxy-1-methyl-2(1H)-quinolinone (9.2 mmol) in 50 ml of methanol was added 545 mg of sodium methoxide (10.1 mmol) in 2.5 ml of methanol with cooling on an ice bath. After stirring for 1 hour, to the mixture was added 4.4 g of Amberlyst and stirred at room temperature for 1 hour. The reaction mixture was filtered, the filtrate was concentrated under reduced pressure. The residue was crystallized from THF and hexane to yield 1.75 g of the title compound (7). (yield=81%)

$^1$H-NMR ($d_6$-DMSO, δ-TMS) 11.18 (s, 1H), 10.85 (s, 1H), 8.05 (m, 3H), 3.68 (s, 3H)

IR (KBr, cm$^{-1}$): 3280, 1605, 1550, 1345, 1250

Elemental analysis for $C_{10}H_8N_2O_5$ Calculated (%):C50.81; H3.41; N11.86; O33.87 Found (%):C50.85; H3.45; N11.66; O34.04

EXAMPLE 5

7-amino-3,4-dihydroxy-1-methyl-2(1H)-quinolinone (compound 8)

In accordance with EXAMPLE 3, 7-nitro-3,4-dihydroxy-1-methyl-2(1H)-quinolinone was used instead of 7-nitro-3-acetoxy-4-methoxy-1-methyl-2(1H)-quinolinone, the title compound (8) was obtained. (yield=67%)

$^1$H-NMR ($d_6$-DMSO, δ-TMS) 11.05 (s, 1H), 10.85 (s, 1H), 7.88 (s, 1H), 7.78 (d, 1H J=7.2 Hz), 7.50 (d, 1H, J=7.2 Hz), 5.97 (bs, 2H), 3.65 (s, 3H)

IR (KBr, cm$^{-1}$): 3280, 1605, 1250

Elemental analysis for $C_{10}H_{10}N_2O_3$ Calculated (%):C58.25; H4.89; N13.58; O23.28 Found (%):C58.55; H4.75; N13.66; O23.04

EXAMPLE 6

7-methylamino-3-acetoxy-4-methoxy-1-methyl-2(1H-quinolinone (compound 9)

To a mixture of 0.95 g of 7-amino-3-acetoxy-4-methoxy-1-methyl-2(1H)-quinolinone (3.6 mmol) in 20 ml of DMF were added 0.55 g of potassium carbonate (4.0 mmol) and 0.56 g of methyl iodide (4.0 mmol) and stirred at room temperature for 1 hour. The reaction mixture was added to water and extracted with toluene, the organic layer was concentrated under reduced pressure. Purification of the residue by column chromatography on silica gel (hexane/ethyl acetate=1/1 as an eluent) gave 0.45 g of the title compound (9). (yield=45%)

$^1$H-NMR ($d_6$-DMSO, δ-TMS) 7.95 (s, 1H), 7.85 (d, 1H, J=7.2 Hz), 7.50 (d, 1H, J=7.2 Hz), 5.86 (s, 1H)4.32 (s, 3H), 3.68 (s, 3H), 3.45 (s, 3H), 2.30 (s, 3H)

IR (KBr, cm$^{-1}$): 3280, 1745, 1675, 1250

Elemental analysis for $C14H_{16}N_2O_4$ Calculated (%):C60.86; H5.84; N10.14; O23.16 Found (%):C60.76; H5.95; N10.26; O23.03

EXAMPLE 7

7-methylamino-3-hydroxy-4-methoxy-1-methyl-2(1H)-quinolinone (compound 8)

In accordance with EXAMPLE 4, 7-methylamino-3-acetoxy-4-methoxy-1-methyl-2(1H)-quinolinone was used instead of 7nitro-3-acetoxy-4-hydroxy-1-methyl-2(1H)-quinolinone, the title compound (10) was obtained. (yield=75%)

$^1$H-NMR (d$_6$-DMSO, δ-TMS) 10.45 (s, 1H), 7.95 (s, 1H), 7.85 (d, 1H, J=7.2 Hz), 7.50 (d, 1H, J=7.2 Hz), 5.86 (s, 1H), 4.32 (s, 3H), 3.68 (s, 3H), 3.45 (s, 3H)

IR (KBr, cm$^{-1}$): 3280, 1605, 1250

Elemental analysis for C$_{12}$H$_{14}$N$_2$O$_3$ Calculated (%):C61.52; H6.02; N11.96; O20.49 Found (%):C61.43; H5.98; N11.96; O20.63

EXAMPLE 8

7-nitro-3-acetoxy-4-hydroxy-2(1H)-quinolinone (compound 11)

In accordance with EXAMPLE 1, 7-nitro-4-hydroxy-2(1H)-quinolinone was used instead of 7-nitro-4-hydroxy-1-methyl-2(1H)-quinolinone, the title compound (11) was obtained. (yield=61%)

$^1$H-NMR (d$_6$-DMSO, δ-TMS) 11.45 (s, 1H), 9.56 (s, 1H), 8.27 (s, 1H), 8.18 (d, 1H, J=7.2 Hz), 8.01 (d, 1H, J=7.2 Hz), 2.30 (s, 3H)

IR (KBr, cm$^{-1}$): 3275, 1745, 1680, 1555, 1345

Elemental analysis for C$_{11}$H$_8$N$_2$O$_6$ Calculated (%):C50.01; H3.05; N10.60; O36.34 Found (%):C50.23; H2.98; N10.46; O36.33

EXAMPLE 9

7-nitro-3-acetoxy-4-methoxy-2(1H)-quinolinone (compound 12)

In accordance with EXAMPLE 2, 7-nitro-3-acetoxy-4-hydroxy-2(1H)-quinolinone was used instead of 7-nitro-3-acetoxy-4-hydroxy-1-methyl-2(1H)-quinolinone, the title compound (10) was obtained. (yield=41%)

$^1$H-NMR (d$_6$-DMSO, δ-TMS) 9.56 (s, 1H), 8.27 (s, 1H), 8.18 (d, 1H, J=7.2 Hz), 8.01 (d, 1H, J=7.2 Hz), 4.15 (s, 3H), 2.15 (s, 3H)

IR (KBr, cm$^{-1}$): 3245, 1730, 1650, 1555, 1345

Elemental analysis for C$_{12}$H$_{10}$N$_2$O$_6$ Calculated (%):C51.80; H3.62; N10.07; O34.51 Found (%):C51.83; H3.58; N10.36; O34.23

EXAMPLE 10

7-nitro-3-hydroxy-4-methoxy-2(1H)-quinolinone (compound 13)

In accordance with EXAMPLE 4, 7-nitro-3-acetoxy-4-hydroxy-2(1H)-quinolinone was used instead of 7-nitro-3-acetoxy-4-hydroxy-1-methyl-2(1H)-quinolinone, the title compound (13) was obtained. (yield=79%)

$^1$H-NMR (d$_6$-DMSO, δ-TMS) 10.89 (s, 1H), 9.56 (s, 1H), 8.27 (s, 1H), 8.18 (d, 1H, J=7.2 Hz), 8.01 (d, 1H, J=7.2 Hz), 4.15 (s, 3H)

IR (KBr, cm$^{-1}$):3245, 1600, 1555, 1345

Elemental analysis for C$_{10}$H$_8$N$_2$O$_5$ Calculated (%):C50.85; H3.41; N11.86; O33.87 Found (%):C50.83; H13.48; N11.76; O33.93

EXAMPLE 11

7-amino-3-hydroxy-4-methoxy-2(1H)-quinolinone (compound 14)

In accordance with EXAMPLE 3, 7-nitro-3-hydroxy4-methoxy-2(1H)-quinolinone was used instead of 7-nitro-3-acetoxy-4-methoxy-1-methyl-2(1H)-quinolinone, the title compound (14) was obtained. (yield=66%)

$^1$H-NMR (d$_6$-DMSO, δ-TMS) 10.89 (s, 1H), 9.56 (s, 1H), 7.95 (s, 1H), 7.85 (d, 1H, J=7.2 Hz), 7.50 (d, 1H, J=7.2 Hz), 5.86 (s, 2H), 4.15 (s, 3H)

IR (KBr, cm$^{-1}$): 3245, 1605, 1250

Elemental analysis for C$_{10}$H$_{10}$N$_2$O$_3$ Calculated (%):C58.25; H4.89; N13.58; O23.28 Found (%):C58.28; H4.78; N13.76; O23.18

EXAMPLE 12

7-amino-3-acetoxy-4-methoxy-2(1H)-quinolinone (compound 15)

In accordance with EXAMPLE 3, 7-nitro-3-acetoxy-4-methoxy-2(1H)-quinolinone was used instead of, 7-nitro-3-acetoxy-4-methoxy-1-methyl-2(1H)-quinolinone, the title compound (15) was obtained. (yield=66%)

$^1$H-NMR (d$_6$-DMSO, δ-TMS) 9.56 (s, 1H), 7.95 (s, 1H), 7.85 (d, 1H, J=7.2 Hz), 7.50 (d, 1H, J=7.2 Hz), 5.86 (s, 2H), 4.15 (s, 3H), 2.14 (s, 3H)

IR (KBr, cm$^{-1}$): 3245, 1730, 1680, 1250

Elemental analysis for C$_{12}$H$_{12}$N$_2$O$_4$ Calculated (%):C58.06; H4.87; N11.29; O25.78 Found (%):C58.18; H4.88 N11.16; O25.78

EXAMPLE 13

7-butylamino-3-acetoxy-4-methoxy-2(1H)-quinolinone (compound 16)

In accordance with EXAMPLE 6, 7-amino-3-acetoxy-4-methoxy-2(1H)-quinolinone and butyl iodide were used instead of 7-amino-3-acetoxy-4-methoxy-1-methyl-2(1H)-quinolinone and methyl iodide, the title compound (16) was obtained. (yield=75%)

$^1$H-NMR (d$_6$-DMSO, δ-TMS) 9.56 (s, 1H), 7.90 (s, 1H), 7.85 (d, 1H, J=7.2 Hz), 7.50 (d, 1H, J=7.2 Hz), 6.04 (m, 1H), 4.15 (s, 3H), 3.34 (m, 2H, J=7.5 Hz), 2.14 (s, 3H), 1.80~1.35 (m, 4H), 0.96 (t, 3H, J=7.5 Hz)

IR (KBr, cm$^{-1}$): 3245, 1734, 1680, 1250

Elemental analysis for C$_{16}$H$_{20}$N$_2$O$_4$ Calculated (%):C63.14; H6.62; N9.21; O21.03 Found (%):C63.18; H6.88; N9.16; O20.78

EXAMPLE 14

7-butylamino-3-hydroxy-4-methoxy-2(1H)-quinolinone (compound 17)

In accordance with EXAMPLE 4, 7-butylamino-3-acetoxy-4-methoxy-2(1H)-quinolinone was used instead of 7-nitro-3-acetoxy-4-hydroxy-1-methyl-2(1H)-quinolinone, the title compound (17) was obtained. (yield=84%)

$^1$H-NMR (d$_6$-DMSO, δ-TMS) 10.89 (s, 1H), 9.56 (s, 1H), 7.90 (s, 1H), 7.85 (d, 1H, J=7.2 Hz), 7.50 (d, 1H, J=7.2 Hz), 6.04(m, 143H), 4.15 (s, 3H), 3.34 (m, 2, J=7.5 Hz), 1.80~1.35 (m, 4H), 0.96 (t, 3H, J=7.5 Hz)

IR (KBr, cm$^{-1}$): 3245, 1610, 1250

Elemental analysis for C$^{14}$H$_{18}$N$_2$O$_3$ Calculated (%):C64.10; H6.92; N10.68; O18.30 Found (%):C64.18; H6.98; N10.56; 018.28

EXAMPLE 15

7-nitro-3-methoxy-4-hydroxy-1-methyl-2(1H)-quinolinone (compound 18)

After addition of 1.87 g of triethylamine (18.5 mmol) to a mixture of 3.2 g of 7-nitro-3-acetoxy-4-hydroxy-1-methyl-2(1H)-quinolinone (11.5 mmol) in 64 ml of THF, 1.89 g of chloromethyl methyl ether (23.0 mmol) was dropped to the mixture, and stirred at room temperature for 1 hour. Filtration of the reaction mixture, the filtrate was concentrated under reduced pressure to give 3.6 g of 7-nitro-3-acetoxy- 4-methoxymethoxy-1-methyl-2(1H-quinolinone. In accordance with EXAMPLE 4, the obtained 7-nitro-3-acetoxy-4-methoxymethoxy-1-methyl-2(1H)-quinolinone was used instead of 7-nitro-3-acetoxy-4-hydroxy-1-methyl-2(1H)-quinolinone, 7-nitro-3-hydroxy-4-methoxymethoxy-1-methyl-2(1H)-quinolinone was provided. Then in accordance with EXAMPLE 2, 7-nitro-3-methoxy-4-methoxymethoxy-1-methyl-2(1H)-quinolinone was given by methylation reaction. Finally, to a mixture of the obtained 7-nitro-3-methoxy-4-methoxymethoxy-1-methyl-2(1H)-quinolinone in 40 ml of methanol was added 0.22 g of p-toluenesulfonic acid monohydrate and stirred at room temperature for 1 hour. To the reaction mixture was added water, extracted (yield=54%) residue was crystallized from THF and hexane to yield 1.45 g of the title compound (18). (yield=54%)

$^1$H-NMR (d$_6$-DMSO, δ-TMS) 11.29 (s, 1H), 8.27 (s, 1H), 8.18 (d, 1H, J=7.2 Hz), 8.01 (d, 1H, J=7.2 Hz), 3.98 (s, 3H), 3.56 (s, 3H)

IR (KBr, cm$^{-1}$): 3245, 1600, 1550, 1345, 1250

Elemental analysis for C$_{11}$H$_{10}$N$_2$O$_4$ Calculated (%):C52.80; H4.03; N11.20; O31.97 Found (%):C52.67 H3.98; N11.56; O31.79

EXAMPLE 16

7-amino-3-methoxy-4-hydroxy-1-methyl-2(1H)-quinolinone (compound 19)

In accordance with EXAMPLE 3, 7-nitro-3-methoxy-4-hydroxy-1-methyl-2(1H)-quinolinone was used instead of 7-nitro-3-acetoxy-4-methoxy-1-methyl-2(1H)-quinolinone, the title compound (19) was obtained. (yield=78%)

$^1$H-NMR (d$_6$-DMSO, δ-TMS) 10.89 (s, 1H), 7.90 (s, 1H), 7.85 (d, 1H, J=7.2 Hz), 7.50 (d, 1H, J=7.2 Hz), 5.85 (m, 2H), 4.08 (s, 3H), 3.54 (s, 3H)

IR (KBr, cm$^{-1}$): 3245, 1600, 1250

Elemental analysis for C$_{11}$H$_{12}$N$_2$O$_3$ Calculated (%):C59.99; H5.49; N12.72; O21.80 Found (%):C60.01; H5.45; N12.68; O21.86

EXAMPLE 17

7-amino-3-acetoxy-4-ethoxy-1-methyl-2(1H)-quinolinone (compound 20)

In accordance with EXAMPLE 2 and 3, using 7-nitro-3-acetoxy-4-hydroxy-1-methyl-2(1H)-quinolinone, ethyl iodide was used instead of methyl iodide, the title compound (20) was obtained. (yield=56%)

$^1$H-NMR (d$_6$-DMSO, δ-TMS) 7.95 (s, 1H), 7.85 (d, 1H, J=7.2 Hz), 7.50 (d, 1H, J=7.2 Hz), 6.00 (bs, 2H), 4.12 (t, 2H, J=7.5 Hz), 3.58 (s, 3H), 2.30 (s, 3H), 0.98 (t, 3H, J=7.5 Hz)

IR (KBr, cm$^{-1}$): 3245, 1745, 1600, 1245

Elemental analysis for C$_{14}$H$_{16}$N$_2$O$_4$ Calculated (%):C60.86; H5.84; N10.14; O23.16 Found (%):C60.85; H5.95; N9.96; O23.24

EXAMPLE 18

7-amino-3-hexyloxy-4-hydroxy-1-methyl-2(1H)-quinolinone (compound 21)

In accordance with EXAMPLE 15 and 3, using 7-nitro-3-acetoxy-4-hydroxy-1-methyl-2(1H)-quinolinone, hexyl iodide was used instead of methyl iodide, the title compound (21) was obtained. (yield=54%)

$^1$H-NMR (d$_6$-DMSO, δ-TMS) 10.89 (s, 1H), 7.90 (s, 1H), 7.85 (d, 1H, J=7.2 Hz), 7.50 (d, 1H, J=7.2 Hz), 5.85 (m, 2H), 4.23 (d, 2H, J=7.6 Hz), 3.54 (s, 3H), 1.98~1.45 (m, 8H) 1.05 (t, 3H, J=7.5 Hz)

IR(KBr, cm$^{-1}$): 3200, 1590, 1220, 1100

Elemental analysis for C$_{16}$H$_{22}$N$_2$O$_3$ Calculated (%):C66.18; H7.64; N9.65; O16.53 Found (%):C66.18; H7.58; N9.56; O16.68

EXAMPLE 19

7-amino-3-octyloxy-4-hydroxy-1-methyl-2(1H)-quinolinone (compound 22)

In accordance with EXAMPLE 15 and 3, using 7-nitro-3-acetoxy-4-hydroxy-1-methyl-2(1H)-quinolinone, octyl iodide was used instead of methyl iodide, the title compound (22) was obtained. (yield=47%)

$^1$H-NMR (d$_6$-DMSO, δ-TMS) 11.23 (s, 1H), 7.92 (s, 1H), 7.85 (d, 1H, J=7.2 Hz), 7.50 (d, 1H, J=7.2Hz), 5.85 (m, 2H), 4.23 (d, 2H, J=7.6 Hz), 3.54 (s, 3H), 1.86~1.45 (m, 12H), 0.97 (t, 3H, J=7.5 Hz)

IR(KBr, cm$^{-1}$): 3200, 1595, 1230, 1100

Elemental analysis for C$_{18}$H$_{26}$N$_2$O$_3$ Calculated (%):C67.90; H8.23; N8.80; O15.08 Found (%):C67.86; H8.38; N8.96; O14.80

EXAMPLE 20

7-amino-3-hydroxy-4-hexyloxy-1-methyl-2(1H)-quinolinone (compound 23)

In accordance with EXAMPLE 2, 3 and 4, using 7-nitro-3-acetoxy-4-hydroxy-1-methyl-2(1H)-quinolinone, hexyl iodide was used instead of methyl iodide, the title compound (23) was obtained. (yield=54%)

$^1$H-NMR (d$_6$-DMSO, δ-TMS) 11.05 (s, 1H), 7.89 (s, 1H), 7.78 (d, 1H, J=7.2 Hz), 7.50 (d, 1H, J=7.2 Hz), 5.85 (m, 2H), 4.23 (d, 2H, J=7.6 Hz), 3.54 (s, 3H), 1.87~1.45 (m, 8H), 1.02 (t, 3H, J=7.5 Hz)

IR (KBr, cm$^{-1}$): 3245, 1600, 1250

Elemental analysis for C$_{16}$H$_{22}$N$_2$O$_3$ Calculated (%):C66.18; H7.64; N9.65; O16.53 Found (%):C66.13; H7.58; N9.56; O16.73

EXAMPLE 21

7-octylamino-3-methoxy-4-hydroxy-1-methyl-2(1H)-quinolinone (compound 24)

In accordance with EXAMPLE 3, 6 and 15, using 7-nitro-3-acetoxy-4-hydroxy-1-methyl-2(1H)-quinolinone, octyl iodide was used as an alkylating agent of amino group instead of methyl iodide, the title compound (24) was obtained. (yield=54%)

$^1$H-NMR (d$_6$-DMSO, δ-TMS) 11.05 (s, 1H), 7.89 (s, 1H), 7.78 (d, 1H, J=7.2 Hz), 7.50 (d, 1H, J=7.2 Hz), 5.78 (m, 1H), 4.23 (s, 3H), 3.54 (s, 3H), 3.45 (t, 2H, J=7.5 Hz), 1.87~1.45 (m, 12H), 1.02 (t, 3H, J=7.5 Hz)

IR (KBr, cm$^{-1}$): 3245, 1600, 1250

Elemental analysis for C$_{19}$H$_{28}$N$_2$O$_3$ Calculated (%):C68.64; H8.49; N8.43; O14.44 Found (%):C68.53; H8.58; N8.56; O14.33

EXAMPLE 22

7-dimethylamino-3-hexyloxy-4-hydroxy-1-methyl-2(1H)-quinolinone (compound 25)

In accordance with EXAMPLE 3, 6 and 15, using 7-nitro-3-acetoxy-4-hydroxy-1-methyl-2(1H)-quinolinone, hexyl iodide was used as an alkylating agent instead of methyl iodide, the title compound (25) was obtained. (yield=45%)

¹H-NM (d₆-DMSO, δ-TMS) 11.05 (s, 1H), 7.89 (s, 1H), 7.78 (d, 1H, J=7.2 Hz), 7.50 (d, 1H, J=7.2 Hz), 4.23 (t, 2H, J=7.8 Hz), 3.54 (s, 3H), 3.45 (s, 6H), 1.87~1.45 (m, 8H), 0.98 (t, 3H, J=7.5 Hz)

IR (KBr, cm⁻¹) 3245, 1600, 1250

Elemental analysis for $C_{18}H_{26}N_2O_3$ Calculated (%):C67.90; H8.23; N8.80; O15.08 Found (%):C67.83; H8.38; N8.66; O15.13

EXAMPLE 23

7-methylamino-3-hydroxy-4-octyloxy-1-methyl-2(1H)-quinolinone (compound 26)

In accordance with EXAMPLE 2, 3 and 6, using 7-nitro-3-acetoxy-4-hydroxy-1-methyl-2(1H)-quinolinone, octyl iodide was used as an alkylating agent instead of methyl iodide, the title compound (26) was obtained. (yield=58%)

¹H-NMR (d₆-DMSO, δ-TMS) 10.45 (s, 1H), 7.89 (s, 1H), 7.78 (d, 1H, J=7.2 Hz), 7.50 (d, 1H, J=7.2 Hz), 5.76 (m, 1H), 4.13 (t, 2H, J=7.8 Hz), 3.56 (s, 3H), 3.43 (s, 3H), 1.87~1.45 (m, 12H), 0.98 (t, 3H, J=7.5 Hz)

IR (KBr, cm⁻¹): 3245, 1600, 1250

Elemental analysis for $C_{19}H_{28}N_2O_3$ Calculated (%):C68.64; H8.49; N8.43; O14.44 Found (%):C68.83; H8.48; N8.46; O14.23

EXAMPLE 24

7-hexylamino-3-methoxy-4-hydroxy-1-methyl-2(1H)-quinolinone (compound 27)

In accordance with EXAMPLE 3, 6 and 15, using 7-nitro-3-acetoxy-4-hydroxy-1-methyl-2(1H)-quinolinone, hexyl iodide was used as an alkylating agent instead of methyl iodide, the title compound (27) was obtained. (yield=48%)

¹H-NMR (d₆-DMSO, δ-TMS) 11.45 (s, 1H), 7.89 (s, 1H), 7.78 (d, 1H, J=7.2 Hz), 7.50 (d, 1H, J=7.2 Hz), 5.65 (m, 1H), 4.23 (s, 3H), 3.56 (s, 3H), 3.43 (m, 2H), 1.87~1.45 (m, 8H), 0.98 (t, 3H, J=7.5 Hz)

IR (Br, cm⁻¹): 3245, 1600, 1250

Elemental analysis for $C_{17}H_{24}N_2O_3$ Calculated (%):C67.08; H7.95; N9.20; O15.77 Found (%):C67.05; H7.88; N9.36; O15.71

EXAMPLE 25

7-butylamino-3-hydroxy-4-hexyloxy-1-methyl-2(1H)-quinolinone (compound 28)

In accordance with EXAMPLE 2, 3 and 6, using, 7-nitro-3-acetoxy-4-hydroxy-1-methyl-2(1H)-quinolinone, and butyl iodide was used as an alkylating agent instead of methyl iodide, the title compound (28) was obtained. (yield=52%)

¹H-NMR (d₆-DMSO, δ-TMS) 10.45 (s, 1H), 7.89 (s, 1H), 7.78 (d, 1H, J=7.2 Hz), 7.50 (d, 1H, J=7.2 Hz), 5.75 (m, 1H), 4.23 (t, 2H, J=7.6 Hz), 3.56 (s, 3H), 3.43 (m, 2H), 1.87~1.45 (m, 12H), 0.95 (m, 6H)

IR (KBr, cm⁻¹): 3245, 1600, 1250

Elemental analysis for $C_{20}H_{30}N_2O_3$ Calculated (%):C69.33; H8.73; N8.09; O13.85 Found (%):C69.23; H8.88; N8.26; O13.63

EXAMPLE 26

7-methylamino-3-(2-propenyloxy)-4-hydroxy-1-methyl-2(1H)-quinolinone (compound 29)

In accordance with EXAMPLE 15, using 7-nitro-3-acetoxy-4-hydroxy-1-methyl-2(1H)-quinolinone, allyl bromide was used as an alkylating agent instead of methyl iodide, 7-nitro-3-(2-propenyloxy)-4-hydroxy-1-methyl-2(1H)-quinolinone was provided. In the following, the spectrum data was shown.

¹H-NMR (d₆-DMSO, δ-TMS) 11.05 (s, 1H), 8.05 (m, 3H), 5.90 (m, 1H), 5.35~5.20 (m, 2H), 4.57 (d, 2H, J=2.0 Hz), 3.68 (s, 3H)

IR (KBr, cm⁻¹): 3280, 1605, 1550, 1345, 1250

Elemental analysis for $C_{13}H_{12}N_2O_5$ Calculated (%):C56.52; H4.38; N10.14; O28.96 Found (%):C56.43; H4.48; N10.16; O28.93

In accordance with EXAMPLE 3 and 6, using the product prepared above, the title compound (29) was obtained. (yield=49%)

¹H-NMR (d₆-DMSO, δ-TMS) 11.25 (s, 1H), 7.89 (s, 1H), 7.78 (d, 1H, J=7.2 Hz), 7.50 (d, 1H, J=7.2 Hz), 5.92 (m, 1H), 5.75 (m, 1H), 5.25 (m, 2H), 4.58 (d, 2H, J=2.0 Hz), 3.56 (s, 3H), 3.43 (s, 3H)

IR (KBr, cm⁻¹): 3245, 1600, 1250

Elemental analysis for $C_{14}H_{16}N_2O_3$ Calculated (%):C64.60; H6.20; N10.76; O18.44 Found (%):C64.43; H6.48; N10.56;O18.53

EXAMPLE 27

7-methylamino-3-prenyloxy-4-hydroxy-1-methyl-2(1H)-quinolinone (compound 30)

In accordance with EXAMPLE 26, using 7-nitro-3-acetoxy-4-hydroxy-1-methyl-2(1H)-quinolinone, prenyl bromide was used as an alkylating agent instead of allyl bromide, the title compound (30) was obtained. (yield=64%)

hu 1H-NMR (d₆-DMSO, δ-TMS) 11.25 (s, 1H), 7.89 (s, 1H), 7.78 (d, 1H, J=7.2 Hz), 7.50 (d, 1H, J=7.2 Hz), 5.75 (m, 1H), 5.35 (m, 1H), 4.56 (d, 2H, J=2.0 Hz), 3.56 (s, 3H), 3.43 (s, 3H), 1.75 (s, 3H), 1.70 (s, 3H)

IR (KBr, cm⁻¹): 3245, 1680, 1250

Elemental analysis for $C_{16}H_{20}N_2O_3$ Calculated (%):C66.64; H6.99; N9.72; O16.65 Found (%):C66.43; H6.98; N9.87; O16.72

EXAMPLE 28

7-methylamino-3-geranyloxy-4-hydroxy-1-methyl-2(1H)-quinolinone (compound 31)

In accordance with EXAMPLE 26, using 7-nitro-3-acetoxy-4-hydroxy-1-methyl-2(1H)-quinolinone, geranyl bromide was used as an alkylating agent instead of allyl bromide, the title compound (30) was obtained. (yield=58%)

¹H-NMR (d₆-DMSO, δ-TMS) 11.25 (s, 1H), 7.89 (s, 1H), 7.78 (d, 1H, J=7.2 Hz), 7.50 (d, 1H, J=7.2Hz), 5.75 (m, 1H), 5.35 (m, 1H), 5.10 (m, 1H), 4.57 (d, 2H, J=2.8 Hz), 3.53 (s, 3H), 3.43 (s, 3H), 2.10 (m, 4H), 1.75 (s, 3H), 1.68 (s, 3H), 1.60 (s, 3H)

IR (KBr, cm⁻¹): 3245, 1605, 1250

Elemental analysis for $C_{21}H_{28}N_2O_3$ Calculated (%):C70.76; H7.92; N7.86; O13.47 Found (%):C70.73; H7.98; N7.87; O13.42

EXAMPLE 29

7-amino-3-hexyloxy-4-hydroxy-1-ethyl-2(1H)-quinolinone (compound 32)

In accordance with EXAMPLE 15 and 3, using 7-nitro-3-acetoxy-4-hydroxy-1-ethyl-2(1H)-quinolinone, hexyl iodide was used instead of methyl iodide, the title compound (32) was obtained. (yield=54%)

EXAMPLE 30

7-amino-3-hydroxy-4-butyloxy-1-propyl-2(1H)-quinolinone (compound 33)

In accordance with EXAMPLE 2 and 3, using 7-nitro-3-acetoxy-4-hydroxy-1-propyl-2(1H)-quinolinone, butyl iodide was used instead of methyl iodide, the title compound (33) was obtained. (yield=46%)

$^1$H-NM (d$_6$-DMSO, δ-TMS) 10.89 (s, 1H), 7.90 (s, 1H), 7.85 (d, 1H, J=7.2 Hz), 7.50 (d, 1H, J=7.2 Hz), 5.85 (m, 2H), 4.25 (d, 2H, J=7.6 Hz), 3.54 (d, 2H, J=7.8 Hz), 1.98~1.45 (m, 6H), 1.05 (m, 6H)

IR (KBr, cm$^{-1}$): 3245, 1600, 1250

Elemental analysis for C$_{16}$H$_{22}$N$_2$O$_3$ Calculated (%):C66.18; H7.64; N9.65; O16.53 Found (%):C66.08; H7.78; N9.46; O16.68

EXAMPLE 31

7-amino-3-hydroxy-4-decyloxy-1-propyl-2(1H)-quinolinone (compound 34)

In accordance with EXAMPLE 2 and 3, using 7-nitro-3-acetoxy-4-hydroxy-1-propyl-2(1H)-quinolinone, decyl iodide was used instead of methyl iodide, the title compound (34) was obtained. (yield=46%)

$^1$H-NMR (d$_6$-DMSO, δ-TMS) 10.89 (s, 1H), 7.90 (s, 1H), 7.85 (d, 1H, J=7.2 Hz), 7.50 (d, 1H, J=7.2 Hz), 5.85 (m, 2H), 4.25 (d, 2H, J=7.6 Hz), 3.54 (d, 2H, J=7.8 Hz), 2.04~1.23 (m, 18H), 1.05 (m, 6H)

IR (KBr, cm$^1$): 3245, 1600, 1250

Elemental analysis for C$_{22}$H$_{34}$N$_2$O$_3$ Calculated (%):C70.55; H9.15; N7.48; O12.82 Found (%):C70.53; H8.98; N7.46; O13.03

EXAMPLE 32

7-dimethylamino-3-hexyloxy-4-hydroxy-1-butyl-2(1H)-quinolinone (compound 35)

In accordance with EXAMPLE 3, 6 and 15, using 7-nitro-3-acetoxy-4-hydroxy-1-butyl-2(1H)-quinolinone, hexyl iodide was used instead of methyl iodide, the title compound (35) was obtained. (yield=45%)

$^1$H-NMR (d$_6$-DMSO, δ-TMS) 11.05 (s, 1H), 7.89 (s, 1H), 7.78 (d, 1H, J=7.2 Hz), 7.50 (d, 1H, J=7.2 Hz), 4.23 (t, 2H, J=7.8 Hz), 3.54 (m, 2H), 3.45 (s, 6H), 1.97~1.45 (m, 12H), 0.98 (m, 6H)

IR (KBr, cm$^{-1}$): 3245, 1600, 1250

Elemental analysis for C$_{21}$H$_{32}$N$_2$O$_3$ Calculated (%):C69.97; H8.95; N7.77; O13.32 Found (%):C69.93; H8.88; N7.66; O13.53

EXAMPLE 33

7-dimethylamino-3-hydroxy-4-methoxy-1-butyl-2(1H)-quinolinone (compound 36)

In accordance with EXAMPLE 2, 3 and 6,7-nitro-3-acetoxy-4-hydroxy-1-butyl-2(1H)-quinolinone was used instead of 7-nitro-3-acetoxy-4-hydroxy-1-methyl-2(1H)-quinolinone, the title compound (36) was obtained. (yield=47%)

$^1$H-NMR, (d6-DMSO, δ-TMS) 11.05 (s, 1H), 7.89 (s, 1H), 7.78 (d, 1H, J=7.2 Hz), 7.50 (d, 1H, J=7.2 Hz), 4.23 (s, 3H), 3.54 (m, 2H), 3.45 (s, 6H), 1.97~1.45 (m, 4H), 0.98 (d, 3H, J=7.9

IR (KBr, cm$^{-1}$): 3230, 1610, 1250

Elemental analysis for C$_{16}$H$_{22}$N$_2$O$_3$ Calculated (%):C66.18; H7.64; N9.65; O16.53 Found (%):C66.19; H7.78; N9.66; O16.37

EXAMPLE 34

7-methylamino-3-prenyloxy-4-hydroxy-1-butyl-2(1H)-quinolinone (compound 37)

In accordance with EXAMPLE 26, using 7-nitro-3-acetoxy-4-hydroxy-1-butyl-2(1H)-quinolinone, prenyl bromide was used instead of allyl bromide, the title compound (37) was obtained. (yield=57%)

$^1$H-NMR (d$_6$-DMSO, δ-TMS) 11.25 (s, 1H), 7.89 (s, 1H), 7.78 (d, 1H, J=7.2 Hz), 7.50 (d, 1H, J=7.2 Hz), 5.75 (m, 1H), 5.35 (m, 1H), 4.56 (d, 2H, J=2.0 Hz), 3.56 (d, 2H, J=7.9 Hz), 3.43 (s, 3H), 1.78~1.23 (m, 4H), 1.75 (s, 3H), 1.70 (s, 3H), 0.97 (t, 3H, J=7.9 Hz)

IR (KBr, cm$^{-1}$): 3245, 1605, 1250

Elemental analysis for C$_{19}$H$_{26}$N$_2$O$_3$ Calculated (%):C69.06; H7.93; N8.48; O14.53 Found (%):C69.19; H7.98; N8.57; O14.26

EXAMPLE 35

7-methylamino-3-hydroxy-4-prenyloxy-1-butyl-2(1H)-quinolinone (compound 38)

In accordance with EXAMPLE 2, 3 and 6, using 7-nitro-3-acetoxy-4-hydroxy-1-butyl-2(1H)-quinolinone, prenyl bromide was used as an alkylating agent instead of methyl iodide, the title compound (38) was obtained. (yield=47%)

$^1$H-NMR (d$_6$-DMSO, δ-TMS) 10.25 (s, 1H), 7.89 (s, 1H), 7.78 (d, 1H, J=7.2 Hz), 7.50 (d, 1H, J=7.2 Hz), 5,75 (m, 1H), 5.35 (m, 1H,4.56 (d, 2H, J=2.0 Hz), 3.56 (d, 2H, J=7.9Hz), 3.43 (s, 3H), 1.78~1.23 (m, 4H), 1.75 (s, 3H), 1.70 (s, 3H, 0.97 (t, 3H, J=7.9 Hz)

IR (KBr, cm$^{-1}$): 3245, 1620, 1250

Elemental analysis for C$_{19}$H$_{26}$N$_2$O$_3$ Calculated (%):C69.06; H7.93; N8.48; O14.53 Found (%):C69.21; H7.95; N8.57; O14.27

EXAMPLE 36

7-acetylamino-3-octyloxy-4-hydroxy-1-methyl-2(1H)-quinolinone (compound 39)

To a solution of 1.50 g of 7-amino-3-octyloxy-4-hydroxy-1-methyl-2(1H)-quinolinone (4.7 mmol) in 15 ml of pyridine was added 0.48 g of acetic anhydride (4.7 mmol) with cooling on an ice bath, and stirred for 1 hour. The mixture was poured into water and extracted with ethyl acetate. The organic layer was washed with 4N-HCl, and concentrated under reduced pressure. The residue was purified by column chromatography on silica gel (hexane/ethyl acetate=2/1 as an eluent) to give 1.03 g of the title compound (39). (yield=67%)

$^1$H-NMR (d$_6$-DMSO, δ-TMS) 10.28 (s, 1H), 10.23 (s, 1H), 7.85 (s, 1H), 7.80 (d, 1H, J=7.2 Hz), 7.40 (d, 1H, J=7.2 Hz), 3.94 (d, 2H, J=7.6 Hz), 3.52 (s, 3H), 2.10 (s, 3H), 1.71~1.20 (m, 12H), 0.86 (t, 3H, J=7.5 Hz)

---

Page 47 begins:

$^1$H-NMR (d$_6$-DMSO, δ-TMS) 10.89 (s, 1H), 7.90 (s, 1H), 7.85 (d, 1H, J=7.2 Hz), 7.50 (d, 1H, J=7.2 Hz), 5.85 (m, 2H), 4.23 (d, 2H, J=7.6 Hz), 3.54 (d, 2H, J=7.8 Hz), 1.98~1.45 (m, 8H), 1.05 (m, 6H)

IR (KBr, cm$^{-1}$): 3245, 1600, 1250

Elemental analysis for C$_{17}$H$_{24}$N$_2$O$_3$ Calculated (%):C67.08; H7.95; N9.20; O15.77 Found (%):C67.18; H7.88; N9.26; O15.68

IR (KBr, cm$^{-1}$): 3245, 1650, 1600, 1220

Elemental analysis for $C_{20}H_{28}N_2O_4$ Calculated (%):C66.64; H7.83; N7.77; O1, 7.76 Found (%):C66.86; H7.88; N7.96; O1, 7.30

EXAMPLE 37

7-(4-acetoxy-3,5-dimethoxycinnamoylamino)-3-octyloxy-4-hydroxy-1-methyl-2(1H1)-quinolinone (compound 40)

To a solution of 1.50 g of 7-amino-3-octyloxy-4-hydroxy-1-methyl-2(1H)-quinolinone (4.7 mmol) in 15 ml of pyridine was added 1.33 g of 4-acetoxy-3,5-dimethoxycinnamoyl chloride (4.7 mmol) with cooling on an ice bath, and stirred for 1 hour. The mixture was poured into water and extracted with ethyl acetate. The organic layer was washed with 4N-HCl, and concentrated under reduced pressure. The residue was purified by column chromatography on silica gel (dichloromethane/ethyl acetate=2/1 as an eluent) to give 1.70 g of the title compound (40). (yield= 64%)

$^1$H-NMR (d$_6$-DMSO, δ-TMS) 10.50 (s, 1H), 10.21 (s, 1H), 7.92 (s, 1H), 7.85 (d, 1H, J=8.8 Hz), 7.5 (d, 1H, J=15.6 Hz), 7.49 (s, 1H), 6.93 (s, 2H), 6.75 (d, 1H, J=15.6 Hz), 3.92 (t, 2H, J=6.8 Hz), 3.83 (s, 6H), 3.54 (s, 3H), 2.25 (s, 3H), 1.68 (m, 2H), 1.25 (m, 10H), 0.86 (t, 3H, J=6.8 Hz)

IR (KBr,cm$^{-1}$):3550,2940, 1725, 1600, 1515, 1250, 1100

Elemental analysis for $C_{31}H_{38}N_2O_8$ Calculated (%):C65.71; H6.76; N4.94; O22.59 Found (%):C65.86; H6.68; N4.96; O22.50

EXAMPLE 38

7-(3,5-dimethoxy-4-hydroxycinnamoylamino)-3-octyloxy-4-hydroxy-1-methyl-2(1H)-quinolinone (compound 41)

To a mixture of 1.20 g of 7-(4-acetoxy-3,5-dimethoxylcinnamoylamino)-3-octyloxy- 4-hydroxy-1-methyl-2(1H)-quinolinone (2.11 mmol) in 15 ml of methanol was added 0.46 g of sodium methoxide (8.4 mmol) with cooling on an ice bath, and stirred for 1 hour. After addition of Amberlyst 1.8 g, the mixture was stirred at room temperature for 1 hour, filtered and the filtrate was concentrated under reduced pressure. The residue was crystallized from and hexane to yield 0.79 g of the title compound (41). (yield=71%)

$^1$H-NMR (d$_6$-DMSO, δ-TMS) 10.39 (s, 1H), 10.29 (s, 1H), 8.92 (s, 1H), 7.99 (s, 1H), 7.85 (d, 1H, J=8.8 Hz), 7.53 (d, 1H, J=15.6 Hz), 7.49 (s, 1H), 6.93 (s, 2H), 6.75 (d, 1H, J=15.6 Hz), 3.92 (t, 2H, J=6.8 Hz), 3.82 (s, 6H), 3.54 (s, 3H), 1.68 (m, 2H), 1.25 (m, 10H), 0.86 (t, 3H, J=6.8 Hz)

IR (KBr, cm$^{-1}$): 3550, 2940, 1600, 1515, 1250, 1100

Elemental analysis for $C_{29}H_{36}N_2O_7$ Calculated (%):C66.39; H6.92; N5.34; O21.35 Found (%):C66.45; H7.08; N4.96; O21.51

EXAMPLE 39

7-(4-acetoxy-3,5-dimethoxycinnamoylamino)-3-hexyloxy-4-hydroxy-1-methyl-2(1H)-quinolinone (compound 42)

In accordance with EXAMPLE 37, 7-amino-3-hexyloxy-4-hydroxy-1-methyl-2(1H)-quinolinone was used instead of 7-amino-3-octyloxy-4-hydroxy-1-methyl-2(1H)-quinolinone, the title compound (42) was obtained. (yield=62%)

$^1$H-NMR (d$_6$-DMSO, δ-TMS) 10.50 (s, 1H), 10.21 (s, 1H), 7.92 (s, 1H), 7.85 (d, 1H, J=8.8 Hz), 7.50 (d, 1H, J=15.6 Hz), 7.49 (s, 1H), 6.93 (s, 2H), 6.75 (d, 1H, J=15.6 Hz), 3.92 (t, 2H, J=6.8 Hz), 3.82 (s, 6H), 3.54 (s, 3H), 2.25 (s, 3H), 1.68 (m, 2H), 1.25 (m, 6H), 0.86 (t, 3H, J=6.8 Hz)

IR(KBr, cm$^{-1}$):3550, 2940, 1725, 1600, 1515, 1250, 1100

Elemental analysis for $C_{30}H_{36}N_2O_7$ Calculated (%):C64.67; H6.36; N5.20; O23. 76 Found (%):C64.85; H6.46; N5.12; O23.57

EXAMPLE 40

7-(4-hydroxy-3,5-dimethoxycinnamoylamino)-3-hexyloxy-4-hydroxy-1-methyl-2(1H)-quinolinone (compound 43)

In accordance with EXAMPLE 38, 7-(4-acetoxy-3,5-dimethoxy cinnamoylamino)-3-hexyloxy-4-hydroxy-1-methyl-2(1H)-quinolinone was used instead of 7-(4-acetoxy-3,5-dimethoxycinnamoylamino)-3-octyloxy-4-hydroxy-1-methyl-2(1H)-quinolinone, the title compound (43) was obtained. (yield=74%)

$^1$H-NMR (d$_6$-DMSO, δ-TMS) 10.39 (s, 1H), 10.29 (s, 1H), 8.92 (s, 1H), 7.99 (s, 1H), 7.85 (d, 1H, J=8.8 Hz), 7.53 (d, 1H, J=15.6 Hz), 7.49 (s, 1H), 6.93 (s, 2H), 6.75 (d, 1H, J=15.6 Hz), 3.92 (t, 2H, J=6.8 Hz), 3.82 (s, 6H), 3.54 (s, 3H), 1.68 (m, 2H), 1.25 (m, 6H), 0.86 (t, 3H, J=6.8 Hz)

IR (KBr, cm$^{-1}$):3550, 2940, 1600, 1515, 1250, 1100

Elemental analysis for $C_{27}H_{32}N_2O_7$ Calculated (%):C65.31; H6.50; N5.64; O22.56 Found (%):C65.35; H6.52; N5.59; O22.54

EXAMPLE 41

7-(4-acetoxy-3-methoxycinnamoylamino)-3-octyloxy-4-hydroxy-1-methyl-2(1H)-quinolinone (compound 44)

In accordance with EXAMPLE 37, 4-acetoxy-3-methoxycinnamoyl chloride was used instead of 4-acetoxy-3,5-dimethoxycinnamoyl chloride, the title compound (44) was obtained. (yield=58%)

$^1$H-NMR (d$_6$-DMSO, δ-TMS) 10.50 (s, 1H), 10.18 (s, 1H), 7.92 (s, 1H), 7.85 (d, 1H, J=8.8 Hz), 7.65 (m, 2H), 7.50 (d, 1H, J=15.6 Hz), 7.49 (s, 1H), 6.93 (d, 1H, J=8.8 Hz), 6.75 (d, 1H, J=15.6 Hz), 3.92 (t, 2H, J=6.8 Hz), 3.82 (s, 3H), 3.54 (s, 3H), 2.21 (s, 3H), 1.68 (m, 2H), 1.25 (m, 10H), 0.86 (t, 3H, J=6.8 Hz)

IR (KBr, cm$^{-1}$): 3550, 2940, 1725, 1600, 1515, 1250, 1100

Elemental analysis for $C_{30}H_{36}N_2O_7$ Calculated (%):C67.14; H6.76; N5.22; O20.87 Found (%):C66.96; H6.68; N5.16; O21.20

EXAMPLE 42

7-(4-hydroxy-3-methoxycinnamoylamino)-3-octyloxy-4-hydroxy-1-methyl-2(1H)-quinolinone (compound 45)

In accordance with EXAMPLE 38, 7-(4-acetoxy-3-methoxycinnamoylamino)-3-octyloxy-4-hydroxy-1-methyl-2(1H)-quinolinone was used instead of 7-(4-acetoxy-3,5-dimethoxycinnamoylamino)-3-octyloxy-4-hydroxy-1-methyl-2(1H)-quinolinone, the title compound (45) was obtained. (yield=74%)

$^1$H-NMR (d$_6$-DMSO, δ-TMS) 10.50 (s, 1H), 10.10 (s, 1H), 8.92 (s, 1H), 7.92 (s, 1H), 7.85 (d, 1H, J=8.8 Hz), 7.65 (m, 2H), 7.50 (d, 1H, J=15.6 Hz), 7.49 (s, 1H), 6.93 (d, 1H, J=8.8 Hz), 7.65 J=15.6 Hz), 3.92 (t, 2H, J=6.8 Hz), 3.82 (s, 3H), 3.54 (s, 3H), 1.68 (m, 2H), 1.25 (m, 10H), 0.86 (t, 3H, J=6.8 Hz)

IR (KBr, cm$^{-1}$): 3550, 2940, 1600, 1515, 1250, 1100

Elemental analysis for $C_{28}H_{34}N_2O_6$ Calculated (%):C67.99; H6.93; N5.66; O19.41 Found (%):C67.96; H6.78; N5.46; O19.80

EXAMPLE 43

7-(2-propenylamino)-3-octyloxy-4-hydroxy-1-methyl-2(1H)-quinolinone (compound 46)

In accordance with EXAMPLE 3, 6 and 15, using 7-nitro-3-acetoxy-4-hydroxy-1-methyl-2(1H)-quinolinone, allyl bromide was used as an alkylating agent of amino group, the title compound (46) was obtained. (yield=37%)

$^1$H-NMR (d$_6$-DMSO, δ-TMS) 11.23 (s, 1H), 7.92 (s, 1H), 7.85 (d, 1H, J=7.2 Hz), 7.50 (d, 1H, J=7.2 Hz), 5.92 (m, 1H), 5.75 (m, 1H), 5.25 (m, 2H), 4.58 (d, 2H, J=2.0 Hz), 4.23 (d, 2H, J=7.6 Hz), 3.54 (s, 3H), 1.86~1.45 (m, 12H), 0.97 (t, 3H, J=7.5 Hz)

IR (KBr, cm$^{-1}$): 3245, 1605, 1250

Elemental analysis for $C_{21}H_{30}N_2O_3$ Calculated (%):C70.36; H8.44; N7.82; O13.39 Found (%):C70.39; H8.58; N7.96; O13.07

EXAMPLE 44

7-benzylamino-3-octyloxy-4-hydroxy-1-methyl-2(1H)-quinolinone (compound 47)

In accordance with EXAMPLE 3, 6 and 15, using 7-nitro-3-acetoxy-4-hydroxy-1-methyl-2(1H)-quinolinone, and benzyl chloride was used as an alkylating agent of amino group, the title compound (47) was obtained. (yield=45%)

$^1$H-NMR (d$_6$-DMSO, δ-TMS) 11.20 (s, 1H), 7.92~7.26 (m, 8H), 5.73 (m, 1H), 4.23 (d, 2H, J=7.6 Hz), 3.85 (m, 2H), 3.54 (s, 3H), 1.86~1.45 (m, 12H), 0.97 (t, 3H, J=7.5 Hz)

IR (KBr, cm$^{-1}$): 3235, 1610, 1250

Elemental analysis for $C_{25}H_{32}N_2O_3$ Calculated (%):C73.49; H7.90; N6.86; O11.75 Found (%):C73.39; H8.08; N6.96; O11.57

EXAMPLE 45

7-prenylamino-3-octyloxy-4-hydroxy-1-methyl-2(1H)-quinolinone (compound 48)

In accordance with EXAMPLE 3, 6 and 15, using 7-nitro-3-acetoxy-4-hydroxy-1-methyl-2(1H)-quinolinone, prenyl bromide was used as an alkylating agent of amino group, the title compound (48) was obtained. (yield=54%)

$^1$H-NMR (d$_6$-DMSO, δ-TMS) 11.23 (s, 1H), 7.92 (s, 1H), 7.85 (d, 1H, J=7.2 Hz), 7.50 (d, 1H, J=7.2 Hz), 5.35 (m, 1H), 4.23 (d, 2H, J=7.6 Hz), 3.85 (m, 3H), 3.54 (s, 3H), 1.86~1.45 (m, 12H), 1.75 (d, 6H, J=15 Hz), 0.97 (t, 3H, J=7.5 Hz)

IR (KBr, cm$^{-1}$): 3235, 1600, 1230

Elemental analysis for $C_{23}H_{34}N_2O_3$ Calculated (%):C71.47; H8.87; N7.25; O12.42 Found (%):C71.39; H8.78; N7.16; O12.67

EXAMPLE 46

7-benzoylamino-3-octyloxy-4-hydroxy-1-methyl-2(1H1)-quinolinone (compound 49)

In accordance with EXAMPLE 3, 6 and 15, using 7-nitro-3-acetoxy-4-hydroxy-1-methyl- 2(1H)-quinolinone, benzoyl chloride was used as an acylating agent of amino group, the title compound (49) was obtained. (yield=68%)

$^1$H-NMR (d$_6$-DMSO, δ-TMS) 11.20 (s, 1H), 9.85 (s, 1H), 7.83~7.26 (m, 8H), 4.23 (d, 2H, J=7.6 Hz), 3.54 (s, 3H), 1.86~1.45 (m, 12H), 0.95 (t, 3H, J=7.5 Hz)

IR (KBr, cm$^{-1}$): 3235, 1725, 1665, 1250

Elemental analysis for $C_{25}H_{30}N_2O_4$ Calculated (%):C71.06; H7.16; N6.63; O15.15 Found (%):C71.13; H7.08; N6.76; O15.03

EXAMPLE 47

7-amino-3-methoxy-4-benzoyloxy-1-methyl-2(1H)-quinolinone (compound 50).

To a solution of 1.00 g of 7-nitro-3-methoxy-4-hydroxy-1-methyl-2(1H)-quinolinone (4.00 mmol) in 7 ml of pyridine was added 0.675 g of benzoyl chloride (4.80 mmol) and stirred at room temperature for 1 hour. The mixture was poured into 45 ml of 2N-HCl and extracted with 25 ml of ethyl acetate. The organic layer was washed with 20 ml of water, dried over magnesium sulfate and concentrated under reduced pressure. The resulting 7-nitro-3-methoxy-4-benzoyloxy-1-methyl-2(1H)-quinolinone was reduced to prepare 0.70 g of the title compound (50) in accordance with EXAMPLE 3. (yield=56%)

$^1$H-NMR (d$_6$-DMSO, δ-TMS) 7.90 (s, 1H), 7.85 (d, 1H, J=7.2 Hz), 7.65~7.20 (m, 6H), 5.85 (m, 2H), 4.08 (s, 3H), 3.54 (s, 3H)

IR (KBr, cm$^{-1}$): 3245, 1725, 1600, 1250

Elemental analysis for $C_{17}H_{16}N_2O_4$ Calculated (%):C65.37; H5.16; N8.97; O20.49 Found (%):C65.23; H5.15; N8.78; O20.84

EXAMPLE 48

7-amino-4-butoxy-3-hexyloxy-1-methyl-2(1H)-quinolinone (compound 51)

In accordance with EXAMPLE 2, using 7-nitro-3-hexyloxy-4-hydroxy-1-methyl-2(1H)-quinolinone, hexyl iodide was used instead of methyl iodide, 7-nitro-4-butoxy-3-hexyloxy- 1-methyl-2(1H)-quinolinone was provided. Then in accordance with EXAMPLE 3, the title compound (5 1) was obtained by reduction reaction of nitro group. (yield=57%)

$^1$H-NMR (d$_6$-DMSO, δ-TMS) 7.90 (s, 1H), 7.85 (d, 1H, J=7.2 Hz), 7.50 (d, 1H, J=7.2 Hz), 5.85 (m, 2H), 4.25 (m, 4H), 3.54 (s, 3H), 1.98~1.45 (m, 12H), 1.05 (m, 6H)

IR (KBr, cm$^{-1}$): 3200, 1590, 1220, 1100

Elemental analysis for $C_{20}H_{30}N_2O_3$ Calculated (%):C69.33; H8.73; N8.09; O13.85 Found (%):C69.18; H8.58; N8.06; O14.18

Test Example 1

Acute toxicity test in mice

We performed this test in order to confirm the low toxicity of the compounds of the present invention, aminoquinolinone derivatives. In the following, the method of the acute toxicity test will be explained.

Method: Each of aminoquinolinone derivatives (compound No. 6, 8~10, 14~17, 19~51) were forcibly administered orally at the doses of 1000 and 2000 mg/kg to male ICR mice (body weight is 20~25 g, 5 mice per one(1) group), using an esophageal sound. After the administration, the animals were kept in cages for 7 days, to observed general symptoms and to count dead animals. Lethal dose (LD50: mg/kg) was extrapolated from the mortality at 7th day after administration.

In result, the LD50 of all compounds were over 1000 mg/kg, and therefore it was clearly shown that the compounds of the present invention, Aminoquinolinone derivatives, have extremely low toxicity.

Test Example 2

Effect on homologous passive cutaneous anaphylaxis (PCA) reaction in rats

We performed this pharmacological test by PCA reaction which was well known screening test for anti-allergic agents in order to demonstrate that the compounds of the present invention, aminoquinolinone derivatives, possess anti-allergic activity. This experimental animal model is caused by immediate type allergic reaction, namely, antigen-antibody reaction. In the following, the method of this pharmacological test will be explained.

Method: Male wistar rats (9 weeks old) were intradermally administered 0.05 ml of anti-serum against dinitrophenylated ascaris (DNP-As) into two sites on the shaved dorsal skin. 48 hours later, aminoquinolinone derivatives (test compounds) suspended in 0.5% methylcellulose (MC) were given orally at a dose of 100 mg/kg to the animals. 1 hour after administration of Test compounds, the animals were induced anaphylaxis by injection of saline (1 ml) dissolving 1 mg of trinitrophenylated ascaris (TNP-As) and 5 mg of Evans Blue into the tail vein of the animals. 30 minutes after induction of anaphylaxis, animals were anesthetized by ether and killed by bleeding, and were flayed dorsal skin. The leakage of dye was assessed by measuring the diameter (mean of shortest and longest diameter) of the blue spot on the inside surface of dorsal skin. As vehicle control group, only 0.5% MC solution was administered orally, and as positive control group, Tranilast suspended in 0.5% MC were administered orally at a dose of 200 mg/kg to the animals with the same method as the test compounds groups, The inhibition (%) of PCA reaction was calculated according to equation 1 and the result was shown in Table 1. Each experimental group consisted of 5 rats.

In the conditions of this experiment, it was considered that the compound, which inhibited PCA reaction by over forty (40) percent against that in vehicle control group, was evidently effective for immediate type allergy.

$$\text{Inhibition } (\%) = (A-B)/A \times 100 \qquad \text{(Equation 1)}$$

In equation 1
- A: leakage of dye in vehicle control group
- B: leakage of dye in test compound group or positive control group

TABLE 1

| compound No. | Inhibition (%) | compound No. | Inhibition (%) |
|---|---|---|---|
| compound 6 | 46 | compound 30 | 44 |
| compound 8 | 48 | compound 31 | 46 |
| compound 9 | 45 | compound 32 | 44 |
| compound 10 | 42 | compound 33 | 40 |
| compound 14 | 44 | compound 34 | 40 |
| compound 15 | 41 | compound 35 | 45 |
| compound 16 | 42 | compound 36 | 41 |
| compound 17 | 45 | compound 37 | 42 |
| compound 19 | 44 | compound 38 | 40 |
| compound 20 | 41 | compound 39 | 50 |
| compound 21 | 60 | compound 41 | 53 |
| compound 22 | 57 | compound 43 | 49 |
| compound 23 | 44 | compound 44 | 50 |
| compound 24 | 46 | compound 45 | 41 |
| compound 25 | 47 | compound 46 | 46 |
| compound 26 | 41 | compound 47 | 40 |
| compound 27 | 45 | compound 48 | 50 |
| compound 28 | 42 | compound 49 | 46 |
| compound 29 | 42 | Tranilast | 54 |

As shown in Table 1, the inhibition (%) of aminoquinolinone derivatives was forty to sixty percent, it was demonstrated that aminoquinolinone derivatives have equivalent anti-allergic activity to Tranilast. The results of these examples clearly showed that the compounds of the present invention, aminoquinolinone derivatives, were useful anti-allergic agent for immediate type asthma, hay fever and atopic dermatitis etc.

Test Examples 3

Effect on contact dermatitis induced by picryl chloride in mice

We performed this pharmacological test by experimental contact dermatitis model which is well known in order to demonstrate that the compounds of the present invention, aminoquinolinone derivatives, inhibit the delayed type hypersensitization. This experimental animal model which is typical delayed type hypersensitization model, was mainly caused by cellular immune response (Immunology, Vol. 15, P. 405~416, 1968). The delayed type hypersensitization is inhibited by steroid, but can not be effected by known anti-allergic agents. In the following, the method of the pharmacological test will be explained.

Method: Mice, shaved their abdominal skin on previous day, were immunized by applying 0.1 ml of acetone containing 7 mg of picryl chloride to the skin of the abdomen. 7 days after immunization, the thickness of the ear was measured with a dial thickness gauge, then mice were challenged by painting 5 ml of 1% picryl chloride olive oil solution to each side skin of left ear. 24 hours after challenge, the thickness of the left ear was measured again. The compounds of the present invention (test compounds) suspended in 0.5% MC were forcibly administered orally at a dose of 20 mg/kg 12 hours after challenge. As vehicle control group, only 0.5% MC solution was administered orally, and as positive control group, Prednisolone, steroid hormone, was administered orally at a dose of 10 mg/kg and as negative control group, Tranilast was administered orally at a dose of 200 mg/kg. The inhibition (%) against the increase of thickness in vehicle control group was calculated according to equation 2 and 3, the result was shown in table 2. In the conditions of this experiment, it was considered that the compound, which inhibited swelling of the ear by over thirty (30) percent against that in vehicle control group, was evidently effective for delayed type hypersensitization.

$$\text{Increase } (\%) = (A-B)/B \times 100 \qquad \text{(Equation 2)}$$

In equation 2
- A: thickness of the ear at 24 hours after challenge
- B: thickness of the ear before challenge $$\text{Inhibition } (\%) = (C-D)/C \times 100 \qquad \text{(Equation 3)}$$

In equation 3
- C: The increase (%) in vehicle control group
- D: The increase (%) in test compounds group, positive control group

TABLE 2

| compound No. | Inhibition (%) | compound No. | Inhibition (%) |
|---|---|---|---|
| compound 6 | 43 | compound 31 | 45 |
| compound 8 | 41 | compound 32 | 48 |
| compound 9 | 43 | compound 33 | 40 |
| compound 10 | 40 | compound 34 | 37 |
| compound 14 | 38 | compound 35 | 46 |

TABLE 2-continued

| compound No. | Inhibition (%) | compound No. | Inhibition (%) |
|---|---|---|---|
| compound 15 | 40 | compound 36 | 40 |
| compound 16 | 36 | compound 37 | 45 |
| compound 17 | 43 | compound 38 | 37 |
| compound 19 | 45 | compound 39 | 48 |
| compound 20 | 43 | compound 41 | 50 |
| compound 21 | 51 | compound 43 | 53 |
| compound 22 | 55 | compound 44 | 53 |
| compound 23 | 41 | compound 45 | 44 |
| compound 24 | 44 | compound 46 | 55 |
| compound 25 | 48 | compound 47 | 48 |
| compound 26 | 39 | compound 48 | 53 |
| compound 27 | 46 | compound 49 | 43 |
| compound 28 | 37 | Prednisolone | 53 |
| compound 29 | 48 | Tranilast | 6 |
| compound 30 | 52 | | |

It was observed that test compounds effectively inhibit the swelling of the ear by 40 to 55% against that in vehicle control group. Many of the compounds of aminoquinolinone derivatives were equivalent to Prednisolone (inhibition: 53%). In contrast, Tranilast, used widely for allergic disease, did not inhibit delayed type hypersensitization. These results clearly show that the compounds of the present invention, aminoquinolinone derivatives, have exceedingly inhibitory activity against delayed type hypersensitization and are greatly useful anti-allergic agent for serious allergic disease for example delayed type asthma etc.

Test Example 4

Effect on experimental immediate and delayed type asthma model in guinea pigs

The asthma is typical allergic disease and we carried out this pharmacological test by experimental asthmatic model in guinea pigs in order to confirm that the compounds of the present invention, compound 21, 41 and 46, suppress immediate and delayed type asthmatic response. In the following, the method of the pharmacological test will be explained.

Method: Male hartley guinea pigs were sensitized by exposured aerosolized ovalbumine (OVA) (1% in saline) for 10 minutes per a day at eight times. The aerosol was generated by an ultrasonic nebulizer (NE-U12, Omuron inc.). One week after final sensitization, the animals were challenged with inhalation of OVA (2% in saline) for 5 minutes. The animals were pretreated with metyrapone (10 mg/kg, i.v.) at 1 and 4 hours before the challenge, and pyrilamine (10 mg/kg, i.p.) at 30 minutes before the challenge. airway resistance in the conscious animals were measured for 1 minute with PULMOS-1(made in Medical Interface Project Station Inc.) at 1 minute, 2, 4, 5, 6, 7, 8 and 23 to 24 hours after the challenge. Compound 21, 41 and 46 (test compound) suspended in 0.5% methylcellulose (MC) solution were given orally at doses of 5, 10 and 20 mg/kg 1 hour before and 3 hours after the challenge. As a positive control group, Prednisolone was given orally at a dose of 10 mg/kg 2 hours and 16 hours before the challenge. As vehicle control group, only 0.5% MC solution was given orally.

The evaluation of the effect of the compounds on immediate and delayed type asthmatic response was undertaken with percentage of change in airway resistance 1 minute after the challenge and the area under the response curve for percentage of change in airway resistance between 4 and 8 hours after the challenge, respectively. The inhibition (%) of the compounds for immediate and delayed type asthmatic response was calculated according to equation 4 and the result was shown in table 3. Each experimental group consisted of 8 guinea pigs.

$$\text{Inhibition } (\%) = (A-B)/A \times 100 \qquad \text{(equation 4)}$$

In equation 4:

A: percentage of change in airway resistance in vehicle control group

B: percentage of change in airway resistance in test compound group or positive control group

TABLE 3

| | inhibition (%) | | | |
|---|---|---|---|---|
| (mg/kg) | compound 21 | compound 41 | compound 46 | Prednisolone |
| | immediate type asthma | | | |
| 5 | 20 | 26 | 30 | — |
| 10 | 30 | 31 | 28 | 35 |
| 20 | 31 | 43 | 33 | — |
| | delayed type asthma | | | |
| 5 | 23 | 39 | 32 | — |
| 10 | 39 | 54 | 44 | 51 |
| 20 | 48 | 84 | 53 | — |

As shown in table 3, aminoquinolinone derivatives were equivalent or superior anti-asthmatic activity to Prednisolone. Therefore it is confirmed that aminoquinolinone derivatives have exceedingly high activity to inhibit against the immediate and delayed type asthma.

Formulation Example 1

| (5% powders) | |
|---|---|
| the compound of the present invention | 50 mg |
| lactose | 950 mg |
| | 1000 mg |

In the following, the procedure for powders of compound 6, 7~10 and 14~17 will be shown. Crystals of the compound of the present invention were pulverized in a mortar and thoroughly mixed with lactose. Secondly the mixture was pulverized with a pestle and 5% powders of compound 6, 7~10 and 14~17 were obtained.

Formulation Example 2

| (10% powders) | |
|---|---|
| the compound of the present invention | 100 mg |
| lactose | 900 mg |
| | 1000 mg |

In the following, the procedure for powders of compound 19~30 will be shown. The procedure of FORMULATION EXAMPLE 1 was repeated to obtain 10% powders of compound 19~30.

Formulation Example 3

| (10% granules) | |
| --- | --- |
| the compound of the present invention | 300 mg |
| lactose | 2000 mg |
| starch | 670 mg |
| gelatin | 30 mg |
| | 3000 mg |

In the following, the procedure for granules of compound 31~39 will be shown. The compound of the present invention was mixed with the equivalent amount of starch and pulverized in a mortar. This was further mixed with lactose and the remaining portion of starch. Separately from this, 30 mg of gelatin was mixed with 1 ml of purified water, solubilized by heating, cooled and then, with stirring, mixed with 1 ml of ethanol to prepare a gelatin solution. Thereafter, the mixture prepared above was mixed with the gelatin solution, and the resulting mixture was kneaded, granulated and then dried to obtain granules of compound 31~39.

Formulation Example 4

| (5 mg tablets) | |
| --- | --- |
| the compound of the present invention | 5 mg |
| lactose | 62 mg |
| starch | 30 mg |
| talc | 2 mg |
| magnesium stearate | 1 mg |
| | 100 mg/tablet |

In the following, the procedure for tablets of compound 40~51 will be shown. A 20 times larger portion of the above composition was used to prepare tablets each of which containing 5 mg of the active ingredient. That is, 100 mg of the compound of the present invention in a crystal form was pulverized in a mortar and mixed with lactose and starch. The thus prepared formulation was mixed with 10% starch paste, and the mixture was kneaded and then subjected to granulation. After drying, the resulting granules were mixed with talc and magnesium stearate and subjected to tablet making in usual way. With the above procedure, tablets of compound 40~51 were prepared.

Formulation Example 5

| (20 mg tablets) | |
| --- | --- |
| the compound of the present invention | 20 mg |
| 6% hydroxypropylcellulose/lactose | 75 mg |
| stearate/talc | 2 mg |
| potato starch | 3 mg |
| | 100 mg/tablet |

In the following, the procedure for tablets of compound 40~43 will be shown. A 10 times larger portion of the above composition was used to prepare tablets each of which containing 20 mg of the active ingredient. That is, 6 g of hydroxypropylcellulose was dissolved in an appropriate volume of ethanol and mixed with 94 g of lactose, followed by kneading. After drying to a degree, the mixture was passed through a No. 60 mesh, and the thus graded granules were used as 6% hydroxypropylcellulose/lactose. Separately from this, magnesium stearate and talc were mixed at a ratio of 1:4 and used as stearate/talc. Thereafter, the compound of the present invention, 6% hydroxypropylcellulose/lactose, stearate/talc and above procedure, tablets of compound 40~43 were prepared.

Formulation Example 6

| (25 mg tablets) | |
| --- | --- |
| the compound of the present invention | 25 mg |
| lactose | 122 mg |
| carboxymethylstarch | 50 mg |
| talc | 2 mg |
| magnesium stearate | 1 mg |
| | 200 mg/tablet |

In the following, the procedure for tablets of compound 21, 22 and 30~32 will be shown. A 10 times larger portion of the above composition was used to prepare tablets each of which containing 25 mg of the active ingredient. That is, 250 mg of the compound of the present invention in a crystal form was pulverized in a mortar and thoroughly mixed with lactose. An appropriate volume of purified water was added to carboxymethylstarch which was subsequently added to the above mixture, and the resulting mixture was kneaded and then subjected to granulation. After drying, the thus prepared granules were mixed with talc and magnesium stearate and subjected to tablet making in usual way. With the above procedure, tablets of compound 21, 22 and 30~32 were prepared.

Formulation Example 7

| (10 mg capsules) | |
| --- | --- |
| the compound of the present invention | 300 mg |
| lactose | 2000 mg |
| starch | 670 mg |
| gelatin | 30 mg |
| | 3000 mg |

In the following, the procedure for tablets of compound 31~39 will be shown. Granules were prepared in accordance with the procedure described in Formulation EXAMPLE 3 and packed in capsules in 100 mg portions. With the above procedure, capsules of compound 31~39 were prepared.

Formulation Example 8

| (0.5% ointment) | |
| --- | --- |
| the compound of the present invention | 5 mg |
| liquid paraffin | 80 mg |
| petrolatum album | 915 mg |
| | 1000 mg |

In the following, the procedure for tablets of compound 21, 30 and 41~44 will be shown. A 10 times larger portion of the above composition was used to prepare ointment each of which containing 5% of the active ingredient. This is, the compound of the present invention and a little liquid paraffin were sufficiently mixed and pulverized in a mortar, and used as dispersive solution. Separately from this, petrolatum album was mixed with liquid paraffin by heating to prepare a bases. The above dispersive solution was by degrees added to the bases, and thoroughly kneaded to homogenize. With the above procedure, ointment of compound 21, 30 and 41~44 were prepared.

Thus, it is apparent that there has been provided, in accordance with the present invention, a novel nitroquinolinone derivative, an aminoquinolinone derivative from a nitroquinolinone and its physiologically acceptable salt. Also provided aminoquinolinone derivative and its physiologically acceptable salt are excellent anti-allergic agents which have low toxicity and are useful for the treatment or prevention of immediate type and delayed type allergic diseases, particularly an excellent anti-allergic agent which is highly effective on delayed type allergy that cannot be treated effectively with the prior art anti-allergic agents.

While the invention has been described in detail and with reference to specific embodiments thereof, it will be apparent to one skilled in the art that various changes and modifications can be made therein without departing from the spirit and scope thereof.

What is claimed is:

1. A 7-aminoquinolinone derivative expressed by the following general formula (I):

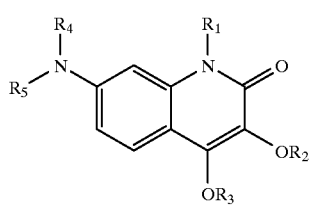

(I)

wherein

R$_1$ is a hydrogen atom or a straight-chain or branched-chain alkyl group having 1–10 carbon atoms;

R$_2$ and R$_3$ are mutually different groups, each of which is selected from the group consisting of a hydrogen atom, an alkanoyl group having 1–4 carbon atoms, an optionally substituted benzoyl group, a straight-chain or branched-chain alkyl group having 1–10 carbon atoms, and a straight-chain or branched-chain alkenyl group having 2–10 carbon atoms; and R$_4$ and R$_5$ are mutually different or identical groups, each of which is selected from the group consisting of a hydrogen atom, an alkanoyl group, a benzoyl group, a cinnamoyl group, a straight-chain or branched-chain alkyl group having 1–10 carbon atoms, a straight-chain or branched-chain alkenyl group having 2–10 carbon atoms, and an aralkyl group; or a physiologically acceptable salt thereof.

2. A 7-aminoquinolinone derivative in accordance with claim 1, wherein R$_2$ is a hydrogen atom; and R$_3$ is a straight-chain or branched-chain alkyl group having 1–10 carbon atoms, or a straight-chain or branched-chain alkenyl group having 2–10 carbon atoms; or a physiologically acceptable salt thereof.

3. A 7-aminoquinolinone derivative in accordance with claim 1, wherein R$_2$ is an alkanoyl group or a benzoyl group; and R$_3$ is a hydrogen atom; or a physiologically acceptable salt thereof.

4. A 7-aminoquinolinone derivative in accordance with claim 1, wherein R$_2$ is an alkanoyl group or an optionally substituted benzoyl group; and R$_3$ is a straight-chain or branched-chain alkyl group having 1–10 carbon atoms, or a straight-chain or branched-chain alkenyl group having 2–10 carbon atoms; or a physiologically acceptable salt thereof.

5. A 7-aminoquinolinone derivative in accordance with claim 1, wherein R$_2$ is a straight-chain or branched-chain alkyl group having 1–10 carbon atoms, or a straight-chain or branched-chain alkenyl group having 2–10 carbon atoms; and R$_3$ is a hydrogen atom; or a physiologically acceptable salt thereof.

6. A 7-aminoquinolinone derivative in accordance with claim 1, wherein R$_2$ is a straight-chain or branched-chain alkyl group having 1–10 carbon atoms, or a straight-chain or branched-chain alkenyl group having 2–10 carbon atoms; and R$_3$ is an alkanoyl group or a benzoyl group; or a physiologically acceptable salt thereof.

7. A 7-aminoquinolinone derivative in accordance with claim 1, wherein R$_2$ and R$_3$ are mutually different straight-chain or branched-chain alkyl groups having 1–10 carbon atoms, or straight-chain or branched-chain alkenyl groups having 2–10 carbon atoms; or a physiologically acceptable salt thereof.

8. A 7-aminoquinolinone derivative in accordance with any one of claim 2 through 7, wherein R$_4$ is a hydrogen atom; and R$_5$ is selected from the group consisting of a hydrogen atom, an alkanoyl group, a benzoyl group, a cinnamoyl group, a straight-chain or branched-chain alkyl group having 1–10 carbon atoms, a straight-chain or branched-chain alkenyl group having 2–10 carbon atoms, and an aralkyl group; or a physiologically acceptable salt thereof.

9. A 7-aminoquinolinone derivative in accordance with claim 8, wherein R$_5$ is an alkanoyl group or a benzoyl group; or a physiologically acceptable salt thereof.

10. A 7-aminoquinolinone derivative in accordance with claim 9 wherein R$_5$ is a cinnamoyl group which optionally has substituent groups; or a physiologically acceptable salt thereof.

11. A 7-aminoquinolinone derivative in accordance with claim 10, wherein R$_5$ is a 4-hydroxy-3-methoxycinnamoyl group, or a 3,5-dimethoxy-4-hydroxycinnamoyl group; or a physiologically acceptable salt thereof.

12. An anti-allergic agent comprising a 7-aminoquinolinone derivative or physiologically acceptable salt thereof in accordance with any one of claims 1 or 2 through 7 and a pharmaceutically acceptable carrier.

13. An anti-allergic agent comprising a 7-aminoquinolinone derivative or physiologically acceptable salt thereof in accordance with claim 8, and a pharmaceutically acceptable carrier.

14. An anti-allergic agent comprising a 7-aminoquinolinone derivative or physiologically acceptable salt thereof in accordance with claim 9 and a pharmaceutically acceptable carrier.

15. An anti-allergic agent comprising a 7-aminoquinolinone derivative or physiologically acceptable salt thereof in accordance with claim 12 and a pharmaceutically acceptable carrier.

16. An anti-allergic agent comprising a 7-aminoquinolinone derivative or physiologically acceptable salt thereof in accordance with claim 11 and a pharmaceutically acceptable carrier.

17. A 7-aminoquinolinone derivative expressed by the following general formula I:

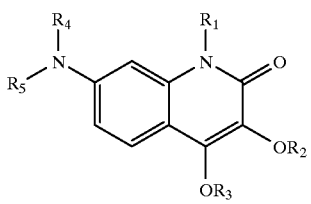

(I)

wherein
- $R_1$ is a hydrogen atom or a straight-chain or branched-chain alkyl group having 1–10 carbon atoms;
- $R_2$ and $R_3$ are hydrogen atoms; and
- $R_4$ and $R_5$ are mutually different or identical groups, $R_4$ being selected from the group consisting of a hydrogen atom, an alkanoyl group, a benzoyl group, a cinnamoyl group, a straight-chain or branched-chain alkyl group having 1–10 carbon atoms, a straight-chain or branched-chain alkenyl group having 2–10 carbon atoms, and an aralkyl group; and $R_5$ being a cinnamoyl group which may have a substituent group; or a physiologically acceptable salt thereof.

18. A 7-aminoquinolinone derivative expressed by the following formula I:

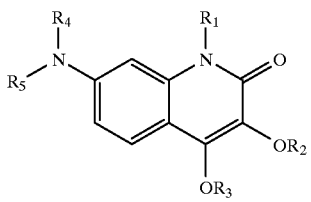

(I)

wherein
- $R_1$ is a hydrogen atom or a straight-chain or branched-chain alkyl group having 1–10 carbon atoms;
- $R_2$ and $R_3$ are identical groups, each being selected from the group consisting of a straight-chain or branched-chain alkyl group having 1–10 carbon atoms, and a straight-chain branched-chain alkenyl group having 2–10 carbon atoms; and
- $R_4$ and $R_5$ are mutually different or identical groups, $R_4$ being selected from the group consisting of a hydrogen atom, an alkanoyl group, a benzoyl group, a cinnamoyl group, a straight-chain or branched-chain alkyl group having 1–10 carbon atoms, a straight-chain or branched-chain alkenyl group having 2–10 carbon atoms, and an aralkyl group; and $R_5$ being a cinnamoyl group which may have a substituent group; or a physiologically acceptable salt thereof.

19. A 7-aminoquinolinone derivative in accordance with claim 17, wherein $R_5$ is a 4-hydroxy-3-methoxycinnamoyl group or a 3,5-dimethoxy-4-hydroxycinnamoyl group; or a physiologically acceptable salt thereof.

20. A 7-aminoquinolinone derivative in accordance with claim 18, wherein $R_5$ is a 4-hydroxy-3-methoxycinnamoyl group or a 3,5-dimethoxy-4-hydroxycinnamoyl group; or a physiologically acceptable salt thereof.

21. An anti-allergic agent comprising a 7-aminoquinolinone derivative or physiologically acceptable salt thereof in accordance with any one of claims 17 through 20, and a pharmaceutically acceptable carrier.

22. A 7-aminoquinolinone derivative expressed by the following wherein general formula (II):

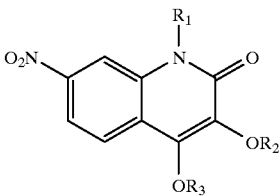

(II)

- $R_1$ is hydrogen atom or a straight-chain or branched-chain alkyl group having 1–10 carbon atoms; and
- $R_2$ and $R_3$ are mutually different groups, each of which is selected from the group consisting of a hydrogen atom, an alkanoyl group, a benzoyl group, a straight-chain or branched-chain alkyl group having 1–10 carbon atoms, and a straight-chain or branched-chain alkenyl group having 2–10 carbon atoms.

23. A 7-nitroquinolinone derivative in accordance with claim 22, wherein $R_2$ and $R_3$ each is a hydrogen atom, a straight-chain or branched-chain alkyl group having 1–10 carbon atoms, or a straight-chain or branched-chain alkenyl group having 2–10 carbon atoms.

24. A 7-nitroquinolinone derivative in accordance with any one of claims 22 through 23, wherein $R_1$ is a hydrogen atom or a straight-chain or branched-chain alkyl group having 1–10 carbon atoms; $R_2$ and $R_3$ each is a hydrogen atom, a straight-chain or branched-chain alkyl group having 1–10 carbon atoms, or a straight-chain or branched-chain alkenyl group having 2–10 carbon atoms.

25. A 7-nitroquinolinone derivative in accordance with claim 24, wherein $R_2$ is an alkyl group having 1–10 carbon atoms, or a straight-chain or branched-chain alkenyl group having 2–10 carbon atoms; and $R_3$ is a hydrogen atom.

26. A 7nitroquinolinone derivative in accordance with claim 22, wherein $R_2$ is an alkanoyl group or a benzoyl group; and $R_3$ is a hydrogen atom, a straight-chain or branched-chain alkyl group having 1–10 carbon atoms, or a straight-chain or branched-chain alkenyl group having 2–10 carbon atoms.

27. A method of treating an allergic disease of mammals, the method comprising administering to a mammal in need of treatment thereof an effective anti-allergic amount of 7-aminoquinolinone derivative or physiologically acceptable salt thereof as claimed in any one of claims 1 through 7.

28. A method of treating an allergic disease of mammals, the method comprising administering to a mammal in need of treatment thereof an effective anti-allergic amount of 7-aminoquinolinone derivative or physiologically acceptable salt thereof as claimed in 8.

29. A method of treating an allergic disease of mammals, the method comprising administering to a mammal in need of treatment thereof an effective anti-allergic amount of 7-aminoquinolinone derivative or physiologically acceptable salt thereof as claimed in claim 9.

30. A method of treating an allergic disease of mammals, the method comprising administering to a mammal in need of treatment thereof an effective anti-allergic amount of 7-aminoquinolinone derivative or physiologically acceptable salt thereof as claimed in claim 10.

31. A method of treating an allergic disease of mammals, the method comprising administering to a mammal in need of treatment thereof an effective anti-allergic amount of 7-aminoquinolinone derivative or physiologically acceptable salt thereof as claimed in claim 11.

32. A method of treating an allergic disease of mammals, the method comprising administering to a mammal in need of treatment thereof an effective anti-allergic amount of 7-aminoquinolinone derivative or physiologically acceptable salt thereof as claimed in any one of claims 17 through 20.

33. A method of using the 7-nitroquinolinone derivative according to claim 22 to make a 7-aminoquinolinone derivative represented by formula (I) or a physiologically acceptable salt thereof,

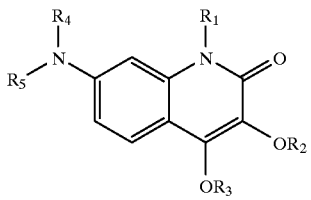
(I)

wherein
- $R_1$ is a hydrogen atom or a straight-chain or branched-chain alkyl group having 1–10 carbon atoms;
- $R_2$ and $R_3$ are mutually different groups, each of which is selected from the group consisting of a hydrogen atom, an alkanoyl group, a benzoyl group, a straight-chain or branched-chain alkyl group having 1–10 carbon atoms, and a straight-chain or branched-chain alkenyl group having 2–10 carbon atoms; and
- $R_4$ and $R_5$ are mutually different or identical groups, each of which is selected from the group consisting of a hydrogen atom, an alkanoyl group, a benzoyl group, a cinnamoyl group, a straight-chain or branched-chain alkyl group having 1–10 carbon atoms, a straight-chain or branched-chain alkenyl group having 2–10 carbon atoms, and an aralkyl group;

the method comprising the stop of using the 7-nitroquinolinone derivative as an intermediate.

34. A method of using the 7-nitroquinolinone derivative according to claim 23 to make a 7-aminoquinolinone derivative represented by formula (I) or a physiologically acceptable salt thereof,

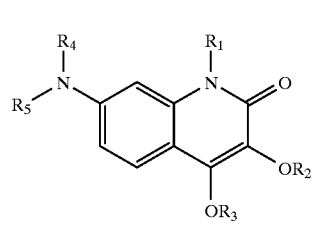
(I)

wherein
- $R_1$ is a hydrogen atom or a straight-chain or branched-chain alkyl group having 1–10 carbon atoms;
- $R_2$ and $R_3$ are mutually different groups, each of which is selected from the group consisting of a hydrogen atom, a straight-chain or branched-chain alkyl group having 1–10 carbon atoms, and a straight-chain or branched-chain alkenyl group having 2–10 carbon atoms; and
- $R_4$ and $R_5$ are mutually different or identical groups, each of which is selected from the group consisting of a hydrogen atom, an alkanoyl group, a benzoyl group, a cinnamoyl group, a straight-chain or branched-chain alkyl group having 1–10 carbon atoms, a straight-chain or branched-chain alkenyl group having 2–10 carbon atoms, and an aralkyl group;

the method comprising the step of using the 7-nitroquinolinone derivative as an intermediate.

* * * * *